United States Patent
Penning et al.

(10) Patent No.: US 9,271,961 B2
(45) Date of Patent: Mar. 1, 2016

(54) BIFUNCTIONAL AKR1C3 INHIBITORS/ANDROGEN RECEPTOR MODULATORS AND METHODS OF USE THEREOF

(71) Applicant: THE TRUSTEES OF THE UNIVERSITY OF PENNSYLVANIA, Philadelphia, PA (US)

(72) Inventors: Trevor M. Penning, Springfield, PA (US); Adegoke O. Adeniji, Drexel Hill, PA (US); Michael C. Burns, Philadelphia, PA (US); Jeffrey Winkler, Wynnewood, PA (US); Barry Twenter, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/050,937

(22) Filed: Oct. 10, 2013

(65) Prior Publication Data

US 2014/0107085 A1 Apr. 17, 2014

Related U.S. Application Data

(63) Continuation-in-part of application No. PCT/US2012/033199, filed on Apr. 12, 2012.

(60) Provisional application No. 61/475,091, filed on Apr. 13, 2011.

(51) Int. Cl.
| | |
|---|---|
| *A61K 31/196* | (2006.01) |
| *C07C 229/60* | (2006.01) |
| *A61P 35/00* | (2006.01) |
| *A61K 31/405* | (2006.01) |
| *A61K 31/195* | (2006.01) |
| *A61K 31/205* | (2006.01) |
| *A61K 45/06* | (2006.01) |
| *C07C 229/58* | (2006.01) |

(52) U.S. Cl.
CPC .......... *A61K 31/405* (2013.01); *A61K 31/195* (2013.01); *A61K 31/196* (2013.01); *A61K 31/205* (2013.01); *A61K 45/06* (2013.01); *C07C 229/58* (2013.01); *C07C 229/60* (2013.01)

(58) Field of Classification Search
CPC ... C07C 229/58; C07C 229/60; A61K 31/196
USPC .......... 514/567; 562/458, 454, 456, 457, 435
See application file for complete search history.

(56) References Cited

U.S. PATENT DOCUMENTS

2006/0235035 A1 10/2006 Hogberg et al.
2007/0129433 A1 6/2007 Lardy et al.

FOREIGN PATENT DOCUMENTS

FR 2862964 B1 12/2006

OTHER PUBLICATIONS

Definition of prevent, Princeton University "About WordNet." WordNet. Princeton University. 2010. <http://wordnet.princeton.edu>, accessed Sep. 18, 2012.*
Flanders Prostate 1984, 5 (6), 621-629.*
Dunning et al. Cancer Epidemiology, Biomarkers and Prevention 1999, 8, 843-854.*
Day et al. Endocrine-Related Cancer 2008, 15, 665-692.*
Loriot et al. Invest. New Drugs 2014, published on-line Apr. 27, 2014, pp. 1-10.*
Khanim et al. British Journal of Cancer 2014, 110, 1506-1516.*
Yin et al. Frontiers in Oncology 2014, vol. 4, article 159, 1-12.*
Lovering et al. Cancer Research 2004, 64, 1802-1810.*
Medivation Press Release Nov. 6, 2007, http://www.medicalnewstoday.com/releases/87762.php, accessed Jul. 23, 2015.*
Adeniji, et al., "Discovery of substituted 3-(phenylamino)benzoic acids as potent and selective inhibitors of type 5 17β-hydroxysteroid dehydrogenase (AKR1C3)," Bioorganic & Medicinal Chemistry Letters, 2011, 21: 1464-1468.
Burczynski, et al., "Expression and Characterization of Four Recombinant Human Dihydrodiol Dehydrogenase Isoforms: Oxidation of trans-7,8-Dihrdroxy-7,8-dihydrobenzo[a]pyrene to Activated o-Quinone Metabolite Benzo[a] pyrene-7,8-dione", Biochemistry, 1998, 37: 6781-6790.
Byrns, et al., "Type 5 17β-hydroxysteroid dehydrogenase/prostaglandin F synthase (AKR1C3): Role in breast cancer and inhibition by non-steroidal anti-inflammatory drug analogs," Chem Biol Interact., Mar. 16, 2009, 178(1-3): 221-227 (Abstract).
International Search Report and Written Opinion for PCT/US2012/033199 dated Sep. 21, 2012.

* cited by examiner

*Primary Examiner* — Shengjun Wang
*Assistant Examiner* — Irina Neagu
(74) *Attorney, Agent, or Firm* — Saul Ewing LLP; Kathryn Doyle; Domingos J. Silva

(57) ABSTRACT

The invention includes compositions comprising selective AKR1C3 inhibitors. The invention also includes compositions comprising bifunctional AKR1C3 inhibitors and selective androgen receptor modulators. The invention further includes methods of treatment using the compositions of the invention.

12 Claims, 42 Drawing Sheets

Fig. 2
STEROID HORMONES
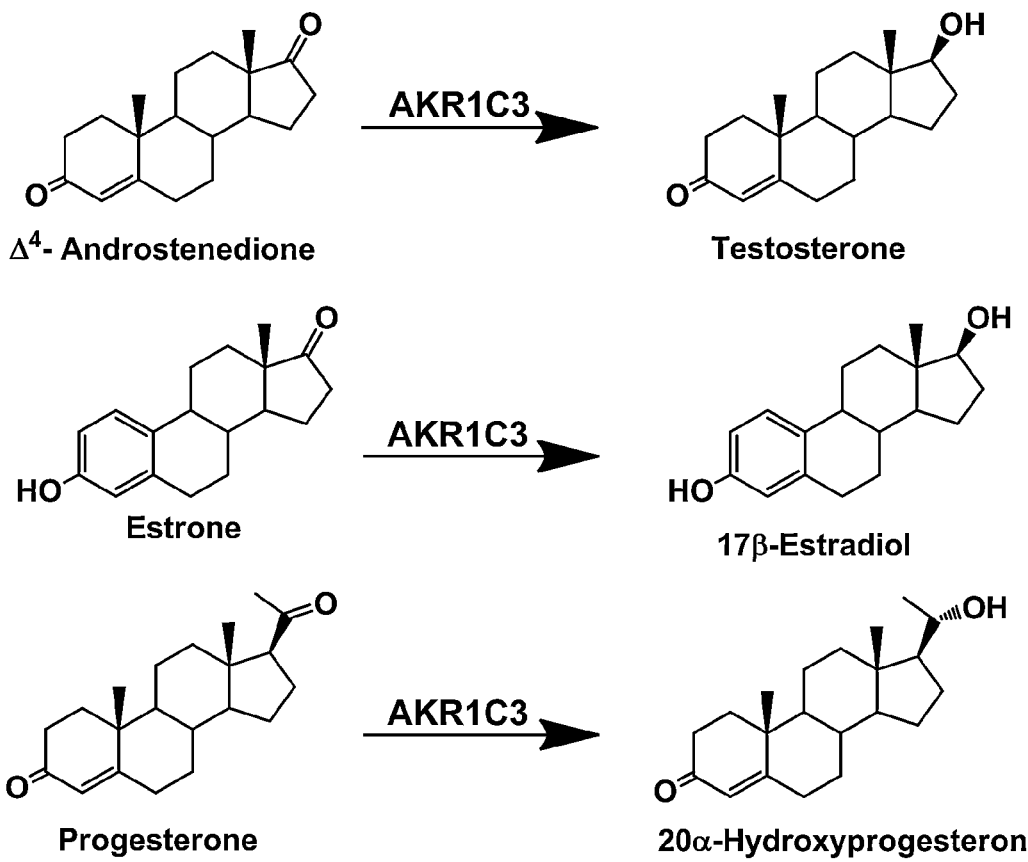
PROSTAGLANDINS
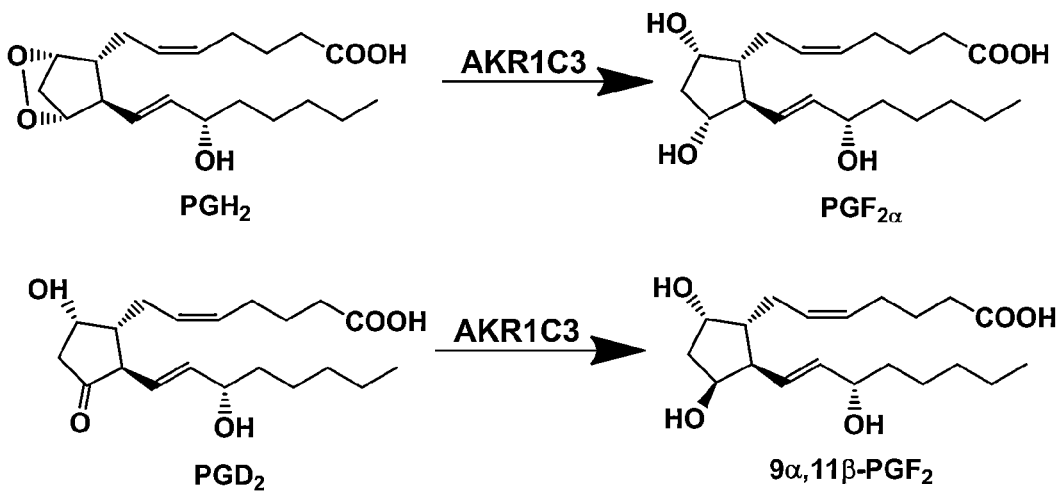

Fig. 4

Indomethacin [32]
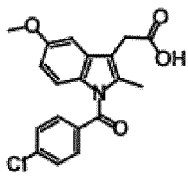
1C3 $K_I$ = 8.2 μM
1C2 $K_I$ > 100 μM
1C1 $K_I$ > 100 μM CBM [32]
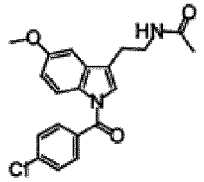
1C3 $K_I$ = 6.0 μM
1C2 $K_I$ > 100 μM
1C1 $K_I$ > 100 μM Flufenamic acid [43]
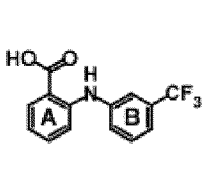
1C3 $IC_{50}$ = 1.65 μM
1C2 $IC_{50}$ = 0.63 μM
1C1 $IC_{50}$ = 0.98 μM 4-Carboxy-2',4'-dinitro-diphenylamine [42]
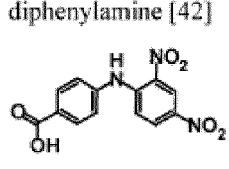
1C3 $K_I$ = 0.38 μM
1C2 $K_I$ = 1.32 μM
1C1 $K_I$ = 2.66 μM MPA [45]
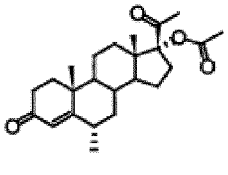
1C3 $IC_{50}$ = 0.28 μM
1C2 $IC_{50}$ = 1.6 μM
1C1 $IC_{50}$ = 0.7 μM EM1404 [48]
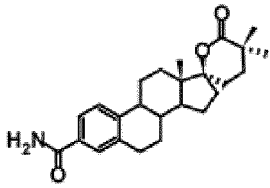
1C3 $K_I$ = 0.0069 μM
1C2 ND
1C1 ND 2'-Hydroxyflavone [50]
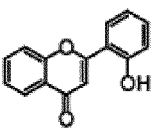
1C3 $IC_{50}$ = 0.30 μM
1C2 $IC_{50}$ = 47.1 μM
1C1 $IC_{50}$ = 6.2 μM α-Methylcinnamic acid [51]
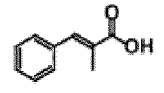
1C3 $IC_{50}$ = 6.4 μM
1C2 ND
1C1 ND Bimatoprost [8]
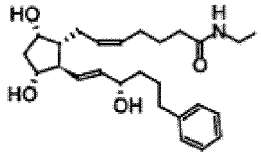
1C3 $IC_{50}$ = 5 μM
1C2 ND
1C1 ND Jasmonic acid [52]
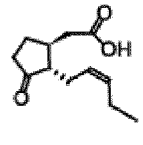
1C3 $K_I$ = 21 μM
1C2 $K_I$ = 15 μM
1C1 $K_I$ = 106 μM Cloxazolam [45]
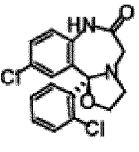
1C3 $K_I$ = 1.5 μM
1C2 $K_I$ > 10 μM
1C1 $K_I$ > 10 μM Diazepam [45]
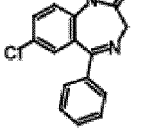
1C3 $IC_{50}$ = 84 μM
1C2 $IC_{50}$ = 2.4 μM
1C1 $IC_{50}$ = 5.6 μM

Fig. 8A

Compound structure and inhibitory potency on AKR1C2 and AKR1C3

| | Compounds | AKR1C3 IC$_{50}$ (μM) | AKR1C2 IC$_{50}$ (μM) | Ratio IC$_{50}$ values AKR1C2:AKR1C3 |
|---|---|---|---|---|
| 1 | Flufenamic acid (HO$_2$C-C$_6$H$_4$-NH-C$_6$H$_4$-CF$_3$) | 0.051 | 0.37 | 7.3 |
| 2 | HO$_2$C-C$_6$H$_4$-NH-C$_6$H$_5$ | 1.5 | 0.44 | 0.29 |
| 3 | HO$_2$C-C$_6$H$_4$-NH-C$_6$H$_5$ | 0.94 | 13 | 14 |
| 4 | HO$_2$C-C$_6$H$_4$-NH-C$_6$H$_5$ | 2.8 | 3.0 | 1.1 |
| 5 | HO$_2$C-C$_6$H$_4$-NH-C$_6$H$_4$-NO$_2$ | 0.036 | 3.4 | 94 |
| 6 | HO$_2$C-C$_6$H$_4$-NH-C$_6$H$_4$-COCH$_3$ | 0.054 | 19 | 360 |

Fig. 8B

Compound structure and inhibitory potency on AKR1C2 and AKR1C3

| Compounds | | AKR1C3 IC$_{50}$ (µM) | AKR1C2 IC$_{50}$ (µM) | Ratio IC$_{50}$ values AKR1C2:AKR1C3 |
|---|---|---|---|---|
| 7 | HO$_2$C-C$_6$H$_4$-NH-C$_6$H$_4$-CF$_3$ | 0.062 | 15 | 250 |
| 8 | HO$_2$C-C$_6$H$_4$-NH-C$_6$H$_4$-Cl | 0.13 | 19 | 150 |
| 9 | HO$_2$C-C$_6$H$_4$-NH-C$_6$H$_4$-Br | 0.12 | 18 | 150 |
| 10 | HO$_2$C-C$_6$H$_4$-NH-C$_6$H$_4$-C(CH$_3$)$_3$ | 0.28 | 31 | 110 |
| 11 | HO$_2$C-C$_6$H$_4$-NH-C$_6$H$_4$-OCH$_3$ | 0.49 | 11 | 23 |
| 12 | HO$_2$C-C$_6$H$_4$-NH-C$_6$H$_4$-CH$_3$ | 0.70 | 56 | 80 |

Fig. 17

| AGENT | RATIONALE |
|---|---|
| Abiraterone | CYP17 inhibitor; targeting intracrine androgen production |
| TOK-001 | CYP17 inhibitor with concomitant inhibition of AR expression |
| SAHA | inhibition of AR expression |
| BMS17HSD | 17HSD inhibition; targeting intracrine androgen production |
| Indomethacin | AKR1C3 inhibition; targeting intracrine androgen production |
| Desatinib | Src-pathway appears to be highly active in CRPC; possible resistance/survival mechanism |
| Selegiline | MAOA inhibition alters AR activity via histone modification |
| MDV3100 | inhibition of AR activity |
| Seliciclib | Cdk1 inhibitor (Cdk1 stabilizes AR in CRPC) |

Fig. 18

| aldo-keto reductase | reduction reaction | | nuclear receptor |
|---|---|---|---|
| | | | *steroid receptors* |
| AKR1C1 | progesterone | → 20α-OH-progesterone | PR* |
| AKR1C1 | 5a-DHT | → 3β-androstanediol | ERβ |
| AKR1C2 | 5a-DHT | → 3α-androstanediol | AR* |
| AKR1C3 | adione | → testosterone | AR |
| AKR1C3 | estrone | → 17b-estradiol | ERα |
| AKR1C3 | progesterone | → 20α-OH progesterone | PR |
| AKR1C3 | DOC | → 20α-DOC | MR* |
| | | | *orphan receptors* |
| AKR1A1 | BP-7,8-diol | → BP-7,8-dione | AhR* |
| AKR1B10 | retinal | → retinol | RXR |
| AKR1C3 | PGD2 | → 11β-PGF2 | PPARγ |
| AKR1D1 | progesterone | → 5β-pregnane-3,20-dione | hPXR, hCAR |

*NR modulated by AKR isoform in *trans*-activation assays

Fig. 30

| Compds (R) [structure: CO₂H-phenyl-NH-phenyl-R] | IC$_{50}$ Values (µM) | | | | | |
|---|---|---|---|---|---|---|
| | 1C3 | 1C1 | 1C2 | 1C4 | 1B1 | 1B10 |
| Compound 5 (*p*-NO$_2$) | 0.03 | 6.74 (204) | 3.38 (101) | 32.7 (988) | > 50 | 46.0 |
| Compound 6 (*p*-Ac) | 0.05 | 15.6 (292) | 19.5 (364) | 25.7 (477) | 38.6 | 37.1 |
| Compound 7 (*p*-CF$_3$) | 0.06 | 22.7 (368) | 15.4 (249) | 62.7 (1015) | > 50 | > 50 |
| Compound 8 (*p*-Cl) | 0.14 | 30.2 (222) | 19.1 (140) | 48.7 (357) | ND | ND |
| Compound 9 (*p*-Br) | 0.13 | 31.3 (250) | 18.1 (145) | 91.4 (728) | > 50 | > 50 |
| Compound 10 (*p*-*t*-Bu) | 0.28 | 35.6 (126) | 31.1 (110) | 39.1 (139) | > 50 | 15 |
| BMT 3-224 (R : *o*-CO$_2$H, *p*-Ac) | 0.04 | 30.5 (787) | 6.41 (165) | 28.7 (739) | 27.7 | 16.2 |
| BMT 5-119 (R: *o*-NO$_2$, *p*-CF$_3$) | 0.03 | 4.23 (132) | 4.35 (136) | 5.50 (172) | 50 | ND |
| BMT 4-90 (R: *o*-NO$_2$, *p*-OMe) | 0.04 | 6.32 (173) | 5.56 (139) | 20.4 (560) | 42.7 | 39.3 |
| Compound 13 | 0.08 | 11.0 (138) | 11.7 (156) | 8.17 (102) | ND | >30 |

Fig. 31

| Cmpds (R) CO₂H-phenyl-NH-phenyl-R | COX-1 IC$_{50}$ (μM) | COX-2 IC$_{50}$ (μM) |
|---|---|---|
| FLU | 2.23 | 0.016 |
| Compound 5 (p-NO$_2$) | 30.76 | 0.74 |
| Compound 6 (p-Ac) | >100 | >100 |
| Compound 7 (p-CF$_3$) | >100 | >100 |
| Compound 8 (p-Cl) | >100 | ND |
| Compound 9 (p-Br) | >100 | >100 |
| Compound 10 (p-t-Bu) | >100 | >100 |
| BMT 3-224 (R : o-CO$_2$H, p-Ac) | >100 | >100 |
| BMT 5-119 (R: o-NO$_2$, p-CF$_3$) | >100 | >100 |
| BMT 4-90 (R: o-NO$_2$, p-OMe) | >100 | >100 |
| Compound 13 | >100 | >100 |

Compound 13

Double-decker AKR1C3 structure

Fig. 38

Data Collection and Refinement Statistics

| Structure | AKR1C3.NADP+.7 (PDB ID: 4DBU) | AKR1C3_NADP+.13 (PDB ID: 4DBS) |
|---|---|---|
| Data collection | | |
| Resolution range (Å) | 50.0–2.53 | 50.0–1.85 |
| Cell parameters (Å, °) | 47.27 x 49.14 x 84.73 | 47.17 x 49.00 x 83.56 |
| | $\alpha = 71.90$, $\beta = 81.58$, $\chi = 70.26$ | $\alpha = 74.42$, $\beta = 87.37$, $\chi = 70.18$ |
| Unique reflections measured b | 22,331 (2242)[b] | 56,673 (5206)[b] |
| $R_{merge}$[a] | 0.093 (0.32)[b] | 0.084 (0.38)[b] |
| $I/\sigma (I)$ | 9.3 (2.8)[b] | 16.7 (3.1)[b] |
| Completeness (%) | 98.6 (97.9)[b] | 98.6 (90.3)[b] |
| Refinement statistics | | |
| Reflections used in refinement/test set | 21,058/1027 | 53,065/2676 |
| $R/R_{free}$[c] | 0.230/0.293 | 0.181/0.222 |
| Protein atoms [d] | 5079 | 5079 |
| Water molecules [d] | 163 | 442 |
| NADP+ molecules [d] | 2 | 2 |
| Inhibitor molecules [d] | 2 | 4 |
| r.m.s. deviations | | |
| Bond lengths (Å) | 0.003 | 0.006 |
| Bond angles (°) | 0.62 | 0.98 |
| Overall B-factor (Å$^2$) | 29 | 33 |
| Cofactor B-factor (Å$^2$) | 21 | 26 |
| Inhibitor B-factor (Å$^2$) | 30 | 35 |
| Ramachandran statistics [e] | | |
| Allowed (%) | 87.6 | 91.3 |
| Additionally allowed (%) | 11.7 | 8.3 |
| Generously allowed (%) | 0.4 | 0.2 |
| Disallowed (%) | 0.4 | 0.2 |

[a] $R_{merge} = \Sigma|I - <I>| / \Sigma I$, where $I$ is the observed intensity and $<I>$ is the average intensity calculated for replicate data.

[b] The number in parentheses refers to the outer 0.1-Å shell of data.

[c] Crystallographic R-factor, $R = \Sigma(|F_o| - |F_c|) / \Sigma|F_o|$ for reflections contained in the working set. Free R-factor, $R_{free} = \Sigma (|F_o| - |F_c|) / \Sigma |F_o|$ for reflections contained in the test set excluded from refinement. $|F_o|$ and $|F_c|$ are the observed and calculated structure factor amplitudes, respectively.

[d] Per asymmetric unit.

[e] Ramachandran statistics were calculated with PROCHECK.

SEQUENCE LISTING

```
<160> NUMBER OF SEQ ID NOS: 6

<210> SEQ ID NO 1
<211> LENGTH: 323
<212> TYPE: PRT
<213> ORGANISM: Homo sapiens

<400> SEQUENCE: 1

Met Asp Ser Lys Tyr Gln Cys Val Lys Leu Asn Asp Gly His Phe Met
1               5                   10                  15

Pro Val Leu Gly Phe Gly Thr Tyr Ala Pro Ala Glu Val Pro Lys Ser
            20                  25                  30

Lys Ala Leu Glu Ala Thr Lys Leu Ala Ile Glu Ala Gly Phe Arg His
        35                  40                  45

Ile Asp Ser Ala His Leu Tyr Asn Asn Glu Glu Gln Val Gly Leu Ala
    50                  55                  60

Ile Arg Ser Lys Ile Ala Asp Gly Ser Val Lys Arg Glu Asp Ile Phe
65                  70                  75                  80

Tyr Thr Ser Lys Leu Trp Cys Asn Ser His Arg Pro Glu Leu Val Arg
                85                  90                  95

Pro Ala Leu Glu Arg Ser Leu Lys Asn Leu Gln Leu Asp Tyr Val Asp
            100                 105                 110

Leu Tyr Leu Ile His Phe Pro Val Ser Val Lys Pro Gly Glu Glu Val
        115                 120                 125

Ile Pro Lys Asp Glu Asn Gly Lys Ile Leu Phe Asp Thr Val Asp Leu
    130                 135                 140

Cys Ala Thr Trp Glu Ala Val Glu Lys Cys Lys Asp Ala Gly Leu Ala
145                 150                 155                 160

Lys Ser Ile Gly Val Ser Asn Phe Asn Arg Arg Gln Leu Glu Met Ile
                165                 170                 175

Leu Asn Lys Pro Gly Leu Lys Tyr Lys Pro Val Cys Asn Gln Val Glu
            180                 185                 190

Cys His Pro Tyr Phe Asn Gln Arg Lys Leu Leu Asp Phe Cys Lys Ser
        195                 200                 205
```

```
Lys Asp Ile Val Leu Val Ala Tyr Ser Ala Leu Gly Ser His Arg Glu
    210                 215                 220

Glu Pro Trp Val Asp Pro Asn Ser Pro Val Leu Leu Glu Asp Pro Val
225                 230                 235                 240

Leu Cys Ala Leu Ala Lys Lys His Lys Arg Thr Pro Ala Leu Ile Ala
                245                 250                 255

Leu Arg Tyr Gln Leu Gln Arg Gly Val Val Leu Ala Lys Ser Tyr
                260                 265                 270

Asn Glu Gln Arg Ile Arg Gln Asn Val Gln Val Phe Glu Phe Gln Leu
                275                 280                 285

Thr Ser Glu Glu Met Lys Ala Ile Asp Gly Leu Asn Arg Asn Val Arg
290                 295                 300

Tyr Leu Thr Leu Asp Ile Phe Ala Gly Pro Pro Asn Tyr Pro Phe Ser
305                 310                 315                 320

Asp Glu Tyr

<210> SEQ ID NO 2
<211> LENGTH: 323
<212> TYPE: PRT
<213> ORGANISM: Homo sapiens

<400> SEQUENCE: 2

Met Asp Ser Lys Tyr Gln Cys Val Lys Leu Asn Asp Gly His Phe Met
1               5                   10                  15

Pro Val Leu Gly Phe Gly Thr Tyr Ala Pro Ala Glu Val Pro Lys Ser
                20                  25                  30

Lys Ala Leu Glu Ala Val Lys Leu Ala Ile Glu Ala Gly Phe His His
            35                  40                  45

Ile Asp Ser Ala His Val Tyr Asn Asn Glu Glu Gln Val Gly Leu Ala
50                  55                  60

Ile Arg Ser Lys Ile Ala Asp Gly Ser Val Lys Arg Glu Asp Ile Phe
65                  70                  75                  80

Tyr Thr Ser Lys Leu Trp Ser Asn Ser His Arg Pro Glu Leu Val Arg
                85                  90                  95

Pro Ala Leu Glu Arg Ser Leu Lys Asn Leu Gln Leu Asp Tyr Val Asp
            100                 105                 110

Leu Tyr Leu Ile His Phe Pro Val Ser Val Lys Pro Gly Glu Glu Val
        115                 120                 125

Ile Pro Lys Asp Glu Asn Gly Lys Ile Leu Phe Asp Thr Val Asp Leu
    130                 135                 140

Cys Ala Thr Trp Glu Ala Met Glu Lys Cys Lys Asp Ala Gly Leu Ala
145                 150                 155                 160

Lys Ser Ile Gly Val Ser Asn Phe Asn His Arg Leu Leu Glu Met Ile
                165                 170                 175

Leu Asn Lys Pro Gly Leu Lys Tyr Lys Pro Val Cys Asn Gln Val Glu
            180                 185                 190

Cys His Pro Tyr Phe Asn Gln Arg Lys Leu Leu Asp Phe Cys Lys Ser
        195                 200                 205

Lys Asp Ile Val Leu Val Ala Tyr Ser Ala Leu Gly Ser His Arg Glu
    210                 215                 220

Glu Pro Trp Val Asp Pro Asn Ser Pro Val Leu Leu Glu Asp Pro Val
225                 230                 235                 240

Leu Cys Ala Leu Ala Lys Lys His Lys Arg Thr Pro Ala Leu Ile Ala
                245                 250                 255
```

```
Leu Arg Tyr Gln Leu Gln Arg Gly Val Val Leu Ala Lys Ser Tyr
            260                 265                 270

Asn Glu Gln Arg Ile Arg Gln Asn Val Gln Val Phe Glu Phe Gln Leu
        275                 280                 285

Thr Ser Glu Glu Met Lys Ala Ile Asp Gly Leu Asn Arg Asn Val Arg
    290                 295                 300

Tyr Leu Thr Leu Asp Ile Phe Ala Gly Pro Pro Asn Tyr Pro Phe Ser
305                 310                 315                 320

Asp Glu Tyr

<210> SEQ ID NO 3
<211> LENGTH: 323
<212> TYPE: PRT
<213> ORGANISM: Homo sapiens

<400> SEQUENCE: 3

Met Asp Ser Lys His Gln Cys Val Lys Leu Asn Asp Gly His Phe Met
1               5                   10                  15

Pro Val Leu Gly Phe Gly Thr Tyr Ala Pro Pro Glu Val Pro Arg Ser
            20                  25                  30

Lys Ala Leu Glu Val Thr Lys Leu Ala Ile Glu Ala Gly Phe Arg His
        35                  40                  45

Ile Asp Ser Ala His Leu Tyr Asn Asn Glu Glu Gln Val Gly Leu Ala
    50                  55                  60

Ile Arg Ser Lys Ile Ala Asp Gly Ser Val Lys Arg Glu Asp Ile Phe
65                  70                  75                  80

Tyr Thr Ser Lys Leu Trp Ser Thr Phe His Arg Pro Glu Leu Val Arg
                85                  90                  95

Pro Ala Leu Glu Asn Ser Leu Lys Lys Ala Gln Leu Asp Tyr Val Asp
            100                 105                 110

Leu Tyr Leu Ile His Ser Pro Met Ser Leu Lys Pro Gly Glu Glu Leu
        115                 120                 125

Ser Pro Thr Asp Glu Asn Gly Lys Val Ile Phe Asp Ile Val Asp Leu
    130                 135                 140

Cys Thr Thr Trp Glu Ala Met Glu Lys Cys Lys Asp Ala Gly Leu Ala
145                 150                 155                 160

Lys Ser Ile Gly Val Ser Asn Phe Asn Arg Arg Gln Leu Glu Met Ile
                165                 170                 175

Leu Asn Lys Pro Gly Leu Lys Tyr Lys Pro Val Cys Asn Gln Val Glu
            180                 185                 190

Cys His Pro Tyr Phe Asn Arg Ser Lys Leu Leu Asp Phe Cys Lys Ser
        195                 200                 205

Lys Asp Ile Val Leu Val Ala Tyr Ser Ala Leu Gly Ser Gln Arg Asp
    210                 215                 220

Lys Arg Trp Val Asp Pro Asn Ser Pro Val Leu Leu Glu Asp Pro Val
225                 230                 235                 240

Leu Cys Ala Leu Ala Lys Lys His Lys Arg Thr Pro Ala Leu Ile Ala
                245                 250                 255

Leu Arg Tyr Gln Leu Gln Arg Gly Val Val Leu Ala Lys Ser Tyr
            260                 265                 270

Asn Glu Gln Arg Ile Arg Gln Asn Val Gln Val Phe Glu Phe Gln Leu
        275                 280                 285

Thr Ala Glu Asp Met Lys Ala Ile Asp Gly Leu Asp Arg Asn Leu His
    290                 295                 300
```

```
Tyr Phe Asn Ser Asp Ser Phe Ala Ser His Pro Asn Tyr Pro Tyr Ser
305                 310                 315                 320

Asp Glu Tyr
```

<210> SEQ ID NO 4
<211> LENGTH: 323
<212> TYPE: PRT
<213> ORGANISM: Homo sapiens

<400> SEQUENCE: 4

```
Met Asp Pro Lys Tyr Gln Arg Val Glu Leu Asn Asp Gly His Phe Met
1               5                   10                  15

Pro Val Leu Gly Phe Gly Thr Tyr Ala Pro Glu Val Pro Arg Asn
            20                  25                  30

Arg Ala Val Glu Val Thr Lys Leu Ala Ile Glu Ala Gly Phe Arg His
            35                  40                  45

Ile Asp Ser Ala Tyr Leu Tyr Asn Asn Glu Glu Gln Val Gly Leu Ala
50                  55                  60

Ile Arg Ser Lys Ile Ala Asp Gly Ser Val Lys Arg Glu Asp Ile Phe
65                  70                  75                  80

Tyr Thr Ser Lys Leu Trp Cys Thr Phe Phe Gln Pro Gln Met Val Gln
                85                  90                  95

Pro Ala Leu Glu Ser Ser Leu Lys Lys Leu Gln Leu Asp Tyr Val Asp
            100                 105                 110

Leu Tyr Leu Leu His Phe Pro Met Ala Leu Lys Pro Gly Glu Thr Pro
        115                 120                 125

Leu Pro Lys Asp Glu Asn Gly Lys Val Ile Phe Asp Thr Val Asp Leu
130                 135                 140

Ser Ala Thr Trp Glu Val Met Glu Lys Cys Lys Asp Ala Gly Leu Ala
145                 150                 155                 160

Lys Ser Ile Gly Val Ser Asn Phe Asn Cys Arg Gln Leu Glu Met Ile
                165                 170                 175

Leu Asn Lys Pro Gly Leu Lys Tyr Lys Pro Val Cys Asn Gln Val Glu
            180                 185                 190

Cys His Pro Tyr Leu Asn Gln Ser Lys Leu Leu Asp Phe Cys Lys Ser
        195                 200                 205

Lys Asp Ile Val Leu Val Ala His Ser Ala Leu Gly Thr Gln Arg His
210                 215                 220

Lys Leu Trp Val Asp Pro Asn Ser Pro Val Leu Leu Glu Asp Pro Val
225                 230                 235                 240

Leu Cys Ala Leu Ala Lys Lys His Lys Arg Thr Pro Ala Leu Ile Ala
                245                 250                 255

Leu Arg Tyr Gln Leu Gln Arg Gly Val Val Val Leu Ala Lys Ser Tyr
            260                 265                 270

Asn Glu Gln Arg Ile Arg Glu Asn Ile Gln Val Phe Glu Phe Gln Leu
        275                 280                 285

Thr Ser Glu Asp Met Lys Val Leu Asp Gly Leu Asn Arg Asn Tyr Arg
290                 295                 300

Tyr Val Val Met Asp Phe Leu Met Asp His Pro Asp Tyr Pro Phe Ser
305                 310                 315                 320

Asp Glu Tyr
```

<210> SEQ ID NO 5
<211> LENGTH: 316
<212> TYPE: PRT

<213> ORGANISM: Homo sapiens

<400> SEQUENCE: 5

```
Met Ala Thr Phe Val Glu Leu Ser Thr Lys Ala Lys Met Pro Ile Val
1               5                   10                  15
Gly Leu Gly Thr Trp Lys Ser Pro Leu Gly Lys Val Lys Glu Ala Val
            20                  25                  30
Lys Val Ala Ile Asp Ala Gly Tyr Arg His Ile Asp Cys Ala Tyr Val
        35                  40                  45
Tyr Gln Asn Glu His Glu Val Gly Glu Ala Ile Gln Glu Lys Ile Gln
    50                  55                  60
Glu Lys Ala Val Lys Arg Glu Asp Leu Phe Ile Val Ser Lys Leu Trp
65                  70                  75                  80
Pro Thr Phe Phe Glu Arg Pro Leu Val Arg Lys Ala Phe Glu Lys Thr
                85                  90                  95
Leu Lys Asp Leu Lys Leu Ser Tyr Leu Asp Val Tyr Leu Ile His Trp
            100                 105                 110
Pro Gln Gly Phe Lys Ser Gly Asp Asp Leu Phe Pro Lys Asp Asp Lys
        115                 120                 125
Gly Asn Ala Ile Gly Gly Lys Ala Thr Phe Leu Asp Ala Trp Glu Ala
    130                 135                 140
Met Glu Glu Leu Val Asp Glu Gly Leu Val Lys Ala Leu Gly Val Ser
145                 150                 155                 160
Asn Phe Ser His Phe Gln Ile Glu Lys Leu Leu Asn Lys Pro Gly Leu
                165                 170                 175
Lys Tyr Lys Pro Val Thr Asn Gln Val Glu Cys His Pro Tyr Leu Thr
            180                 185                 190
Gln Glu Lys Leu Ile Gln Tyr Cys His Ser Lys Gly Ile Thr Val Thr
        195                 200                 205
Ala Tyr Ser Pro Leu Gly Ser Pro Asp Arg Pro Trp Ala Lys Pro Glu
    210                 215                 220
Asp Pro Ser Leu Leu Glu Asp Pro Lys Ile Lys Glu Ile Ala Ala Lys
225                 230                 235                 240
His Lys Lys Thr Ala Ala Gln Val Leu Ile Arg Phe His Ile Gln Arg
                245                 250                 255
Asn Val Ile Val Ile Pro Lys Ser Val Thr Pro Ala Arg Ile Val Glu
            260                 265                 270
Asn Ile Gln Val Phe Asp Phe Lys Leu Ser Asp Glu Glu Met Ala Thr
        275                 280                 285
Ile Leu Ser Phe Asn Arg Asn Trp Arg Ala Cys Asn Val Leu Gln Ser
    290                 295                 300
Ser His Leu Glu Asp Tyr Pro Phe Asp Ala Glu Tyr
305                 310                 315
```

<210> SEQ ID NO 6
<211> LENGTH: 9
<212> TYPE: PRT
<213> ORGANISM: Artificial Sequence
<220> FEATURE:
<223> OTHER INFORMATION: chemically synthesized - leuprolide
<220> FEATURE:
<221> NAME/KEY: MOD_RES
<222> LOCATION: (1)..(1)
<223> OTHER INFORMATION: L-Pyroglutamyl
<220> FEATURE:
<221> NAME/KEY: MOD_RES
<222> LOCATION: (6)..(6)
<223> OTHER INFORMATION: D-leucine

```
<220> FEATURE:
<221> NAME/KEY: MOD_RES
<222> LOCATION: (9)..(9)
<223> OTHER INFORMATION: N-ethyl-prolinamide

<400> SEQUENCE: 6

Xaa His Trp Ser Tyr Xaa Leu Arg Xaa
1               5
```

BIFUNCTIONAL AKR1C3 INHIBITORS/ANDROGEN RECEPTOR MODULATORS AND METHODS OF USE THEREOF

CROSS-REFERENCE TO RELATED APPLICATIONS

The present application is a continuation-in-part application filed under 35 U.S.C. §111(a) claiming benefit to International Patent Application No. PCT/US2012/033199, filed on Apr. 12, 2012, which is entitled to priority under 35 U.S.C. §119(e) to U.S. Provisional Application No. 61/475,091, filed Apr. 13, 2011, each of which application is hereby incorporated herein by reference in its entirety.

REFERENCE TO GOVERNMENT GRANT

This invention was made with government support under grant No. 1R01-CA90744 awarded by National Institutes of Health. The Government has certain rights in the invention.

BACKGROUND OF THE INVENTION

Hormone-dependent malignancies of the prostate and breast are leading causes of cancer incidence and death in the Western world. For example, prostate cancer (PC) is the second most common cancer in American men and is responsible for about 11% of all cancer related deaths (Jemal et al., 2010, Cancer J. Clin. 60:277; Altekruse et al., Eds., SEER Cancer Statistics Review, 1975-2007; National Cancer Institute: Bethesda, Md., 2010). Since the pioneering studies of Charles Huggins, hormonal ablative therapy of these diseases has become standard practice (Huggins & Hodges, 1941, Cancer Res. 1:293-397; Huggins, 1954, J. Natl. Cancer Inst. 15:1-25; Huggins & Yang, 1962, Science 137:257-62; Huggins, 1965, Cancer Res. 25:1163-67). Modern approaches include targeting steroid receptors in these tissues with androgen receptor antagonists (i.e., flutamide, also known as 2-methyl-N-[4-nitro-3-(trifluoromethyl)phenyl]-propanamide; Trachtenberg et al., 2002, Can. J. Urol. 3:240-45) or estrogen receptor antagonists (i.e., tamoxifen, also known as (Z)-2-[4-(1,2-diphenyl-but-1-enyl)phenoxy]-N,N-dimethyl-ethanamine; MacGregor & Jordan, 1998, Pharmacol. Rev. 50:1551-96). With the realization that agents that antagonize androgen and estrogen receptors in one tissue may act as agonists in another tissue, the accepted term for these agents are selective androgen receptor modulators (SARMs) and selective estrogen receptor modulators (SERMs), respectively. SARMs that target prostate cancer need only act as an androgen receptor antagonist in the prostate.

Prostate cancer is initially dependent on testicular androgens and is thus responsive to androgen ablation with surgical or chemical castration. The drug of choice for chemical castration is the luteinizing hormone-releasing hormone (LHRH) agonist leuprolide (p-Pro-His-Trp-Ser-Tyr-D-Leu-Leu-Arg-Pro-NHEt (SEQ ID NO:6); Leupron). Leuprolide inhibits the release of LH from the anterior pituitary and prevents Leydig cell testosterone biosynthesis. Supplementation of castration with blockade of androgen action in the prostate is common and may be achieved with an AR antagonist (bicalutamide, also known as N-[4-cyano-3-(trifluoromethyl)phenyl]-3-[(4-fluorophenyl)sulfonyl]-2-hydroxy-2-methylpropanamide) or by inhibition of type 1 5α-reductase (SRD5A 1) and type 2 5α-reductase (SRD5A2) with dutasteride ((5α,17β)-N-{2,5 bis(trifluoromethyl)phenyl}-3-oxo-4-azaandrost-1-ene-17-carboxamide). Bicalutamide is a relatively weak ligand for the AR and in castrate resistant prostate cancer (CRPC) this compound can even act as a weak agonist leading to the desire for better agents (Tran et al., 2009, Science 324:787-90).

In prostate cancer the therapeutic benefit of androgen deprivation therapy (ADT) is temporary and is often followed by recurrence of a more aggressive metastatic disease—CRPC. CRPC is characterized by elevated intratumoral androgen biosynthesis, increased androgen receptor (AR) signaling and expression of pro-survival genes despite castrate level circulating androgen concentrations (Knudsen & Scher, 2009, Clin. Cancer Res. 15:4792; Knudsen & Penning, 2010, Trends Endocrinol. Metab. 21:315; Locke et al., 2008, Cancer Res. 68:6407). The source of intratumoral androgens is likely dehydroepiandrosterone (DHEA) and/or 4-androstene-3,17-dione ($\Delta^4$-AD) from the adrenal, which is subsequently metabolized to testosterone and 5α-dihydrotestosterone (5α-DHT). The conversion of testosterone to 5α-DHT is catalyzed by 5α-reductase isoforms. While the use of 5α-reductase inhibitors in the treatment of CRPC is still under clinical investigation, chemoprevention trials of prostate cancer with both finasteride (a selective 5α-reductase type 2 inhibitor) and dutasteride (a combined 5α-reductase type 1 and type 2 inhibitor) have produced controversial outcomes (Andriole et al., 2010, N. Engl. J. Med. 362:1192-1202; Thompson et al., 2007, J. Clin. Oncol. 25:3076-81; Walsh, 2010, New Engl. J. Med. 362:1237-38).

Prostate tumor reappearance appears to be driven by adaptive intratumoral androgen synthesis that bypasses the effects of ADT (Attard et al., 2009, Cancer Res. 69:4937-40). This conclusion is supported by the success of the new drug abiraterone acetate ((3S,8R,9S,10R,13S,14S)-10,13-dimethyl-17-(pyridin-3-yl)-2,3,4,7,8,9,10,11,12,13,14,15-dodecahydro-1H-cyclopenta[a]phenanthren-3-ol acetate; Johnson & Johnson) at arresting CRPC and reducing the size of bone metastases in ongoing phase II/III clinical trials (Attard et al., J. Clin. Oncol. 27:3742-48; Reid et al., 2010, J. Clin. Oncol. 28:1489-95). Approved by the FDA for the treatment of CRPC, abiraterone acetate is a steroidal P450 17α-hydroxylase/17,20-lyase (CYP17) inhibitor that blocks the conversion of pregnenolone to dehydroepiandrosterone (DHEA). It blocks this step in the adrenal, which is the major source of circulating DHEA, or in the prostate, if there is de novo steroidogenesis from cholesterol. One disadvantage is that CYP17 is high up in the steroidogenic pathway. Its inhibition in the adrenal diverts pregnenolone to form the mineralocorticoid desoxycorticosterone (DOC). In addition, CYP17 inhibition prevents the formation of cortisol, which feeds-back and inhibits the production of ACTH in the anterior pituitary. The combined effect is elevated DOC production and potentially life-threatening hypertension. Abiraterone is therefore co-administered with a glucocorticoid (hydrocortisone or prednisone) to suppress the hypothalamo-pituitary-adrenal axis. Chronic use of glucocorticoids can however lead to drug induced Cushing's syndrome, immunosuppression and osteoporosis. A second generation analog of abiraterone acetate is VN/124-1 or TOK-001, which is both a CYP17 inhibitor and an AR antagonist that targets the receptor for degradation (Vasaitis et al., 2008, Mol. Cancer Therap. 7:2348-57). VN/124-1 validates the concept that the androgen axes in CRPC may be effectively shut down by inhibiting local androgen biosynthesis and by blocking the AR.

Another approach to treatment has been to develop a more potent AR antagonist than bicalutamide, whose effects may be easily surmounted by intratumoral androgen synthesis, and acts as a weak androgen receptor agonist. MDV3100

(Medivation) also known as enzalutamide prevents both AR nuclear translocation and binding to DNA and is more potent than bicalutamide and does not exhibit agonist activity (Tran et al., 2009, Science 324:787-90). MDV3100 phase I/II clinical trials show that this agent reduces serum PSA, circulating tumor cells and causes radiographic stabilization of the disease (Scher et al., 2010, Lancet 375:1437-46). However, MDV3100 belongs to a class of anti-androgens that carry seizure risk, likely mediated via antagonism of the CNS-based $GABA_A$ receptor (Foster et al., 2010, Prostate 71:480-8). MDV3100 may ultimately be replaced by the use of its congener ARN-509 (Clegg et al., 2012, Cancer Res 72:1494-1503). MDV3100 has also been approved by the FDA for the clinical treatment of CRPC.

Steroid-target tissues produce steroid hormones locally (intracrine and paracrine formation) to maintain their growth (Labrie et al., 1995, Ann. Endocrinol. 56:23-29; Labrie et al., 2000, J. Mol. Endocrinol. 25:1-16). This is important in prostate and breast cancer, which are diseases of the aging male and female. In these individuals, the gonadal production of steroid hormones has been compromised (e.g. andropause and menopause). Enzymes important in the local production of androgens (e.g. type 2 5α-reductase) and estrogens (e.g. aromatase) have become the targets for inhibitor development to treat hormone dependent malignancies of the prostate and breast (Miller, 1996, Endocrine-Related Cancer 3:65-79; Gormley, 1996, Endocrine-Related Cancer 3:65-79). Effective agents include finasteride and exemestane (10,13-dimethyl-6-methylidene-7,8,9,10,11,12,13,14,15,16-decahydrocyclopenta[a]phenanthrene-3,17-dione), which are mechanism-based inactivators for type 2 5α-reductase and aromatase, respectively (Bull et al., 1996, J. Amer. Chem. Soc. 118:2359-65; Brodie et al., 1981, Steroids 38:693-702). One disadvantage to this approach is that aromatase inhibitors cause global decreases in active estrogens and can have unintended side effects (e.g. osteoporosis). Also such treatments can cause these malignancies to become refractory to hormone ablation.

The local levels of steroid hormones are also regulated by hydroxysteroid dehydrogenases (HSDs) (Penning, 1997, Endocrine Rev. 18:281-305). HSDs catalyze the NAD(P)(H) dependent oxidation or reduction of potent steroid hormones to their cognate inactive metabolites and vice-versa. For each steroid hormone there are pairs of HSDs that will either act as reductases or oxidases to modulate the potency of the hormone. For example, type 1 17β-HSD reduces E1 to E2 and is estrogenic, while type 2 and type 4 17β-HSD will oxidize E2 to E1 and attenuate estrogen action (Labrie et al., 2000, J. Mol. Endocrinol. 25:1-16; Labrie et al., 1997, Steroids 62:148-58; Labrie et al., 1995, Cell Biol. 14(10):849-61; Adamski et al., 1995, Biochem J. 311(Pt 2):437-43).

Aldo-keto reductases are a superfamily of 15 families of generally monomeric (37 kDa) cytosolic NAD(P)(H) dependent oxidoreductases that convert carbonyl groups to alcohols. Natural substrates for these enzymes include steroids, prostaglandins and lipid aldehydes (Hyndman et al., 2003, Chem-Biol. Inter. 143-144:621-31). All the HSDs in this superfamily are highly related in sequence (>67% identity) and comprise the AKR1 C family. The four human AKR1C isoforms (AKR1C1—SEQ ID NO:1; AKR1C2—SEQ ID NO:2; AKR1C3—SEQ ID NO:3; AKR1C4—SEQ ID NO:4) have been cloned and expressed, their enzymatic properties in vitro have been assigned, and their tissue specific expression patterns have been studied (Penning et al., 2000, Biochem. J. 351:67-77). Each of the four isoforms share >86% sequence identity but have different ratios of 3-, 17- and 20-ketosteroid reductase activities. AKR1C1 is a major 20α-HSD, AKR1C2 (type 3 3α-HSD and bile acid binding protein) is a major peripheral 3α-HSD, AKR1C3 is a peripheral 17β-HSD, and AKR 1 C4 (type 1 3αHSD/chlordecone reductase) is a hepatic specific 3α-HSD (Penning et al., 2000, Biochem. J. 351:67-77). These enzymes have the potential to regulate ligand occupancy of the PR, AR, and ER. This is referred to as the pre-receptor regulation of nuclear receptors (FIG. 1).

AKR1C3 catalyzes the NADPH dependent reduction of carbonyl moieties on substrates of importance to the pre-receptor regulation of signaling pathways involved in cell proliferation. The interconversion of a ketone group with a hydroxyl group on lipophilic ligands can drastically alter their affinity for their cognate receptors (FIG. 2). For example, AKR1C3 reduces the 17-position of $\Delta^4$-AD (a weak androgen) to form testosterone (a potent androgen) and of estrone (a weak estrogen) to form 17β-estradiol (a potent estrogen), leading to trans-activation of the androgen and estrogen receptors, respectively (Byrns et al., 2010, J. Steroid. Biochem. Mol. Biol. 118:177-87; Dufort et al., 1999, Endocrinology 140:568-74). Because of this activity, AKR1C3 is also known as type 5 17β-hydroxysteroid dehydrogenase. It can also act at the 20-position of progesterone and deoxycorticosterone, forming 20α-hydroxy metabolites with reduced affinities for the progesterone and mineralocorticoid receptors, respectively (Sharma et al., 2006, Mol. Cell. Endocrinol. 248:79-86). Finally, as prostaglandin (PG) F synthase, AKR1C3 catalyzes the stereo-specific reduction of $PGH_2$ to $PGF_{2\alpha}$ and of $PGD_2$ to 9α,11β-$PGF_2$ (Byrns et al., 2010, J. Steroid. Biochem. Mol. Biol. 118:177-87; Suzuki-Yamamoto et al., 1999, FEBS Lett. 462:335-40; Koda et al., 2004, Arch. Biochem. & Biophys. 424:128-36). In the absence of AKR1C3 activity, $PGD_2$ spontaneously dehydrates and rearranges to form the $PGJ_2$ prostanoids (Byrns et al., 2010, J. Steroid. Biochem. Mol. Biol. 118:177-87). The $PGF_2$ isomers are pro-inflammatory and enhance proliferation, while the $PGJ_2$ products, particularly 15-deoxy-$\Delta^{12,14}$-$PGJ_2$ (15d$PGJ_2$), are anti-inflammatory, promote differentiation, and are anti-neoplastic via several mechanisms (Jabbour et al., 2005, Endocrinology 146:4657-64; Ray et al., 2006, J. Immunol. 177:5068-76; Diers et al., 2010, Biochem. J. 430: 69-78; Nakata et al., 2006, Mol. Cancer Therapeutics 1827-35; Butler et al., 2000, Cell Growth Differ. 11:49-61; Scher & Pillinger, 2009, J. Investig. Med. 57:703-08).

The products of reactions catalyzed by AKR1C3 promote tumor growth. It is therefore an important target for the prevention or treatment of both hormone-dependent and hormone-independent cancers. AKR1C3 likely contributes to the development of CRPC through the intratumoral formation of the active androgen testosterone (Penning et al., 2008, Mol. Cell. Endocrinol. 281:1-8). Transcript levels and measurement of testosterone: 5α-dihydrotestosterone (5α-DHT) ratios support the notion that there is a reprogramming of androgen dependence in castrate resistant disease that favors formation of testosterone by AKR1C3 (Montgomery et al., 2008, Cancer Res. 68:4447-54; Mostaghel et al., 2007, Cancer Res. 67:5033-41). Other studies have shown that there three pathways to the potent androgen 5α-DHT in prostate cancer, and AKR1C3 is required for each pathway. The first pathway known as the "classical pathway" involves the sequence: DHEA→$\Delta^4$-Aandrostene-3,17-dione ($\Delta^4$AD) →testosterone→5α-DHT. In this pathway AKR1C3 catalyzes the NADPH dependent reduction of $\Delta^4$-AD→testosterone. The second pathway is known as the "backdoor pathway" in which 5α-reduction occurs at the level of the pregnanes and by-passes DHEA and testosterone altogether (Auchus, 2004, Trends, Endocrinol. Metab. 15: 432-38). The critical conversions are: 5α-pregnane-3,20-dione (DHP)→allopregnanolone→androsterone→3α-androstanediol→5α-DHT. In this pathway, AKR1C3 catalyzes the NADPH dependent reduction of androsterone→3α-androstanediol. The third pathway known as the "alternative pathway" involves the sequence: DHEA→Δ$^4$-AD→5α-androstane-3,17-dione→5α-DHT (Chang et al., 2011, Proc. Natl. Acad, sci. USA 108, 13728-33). In this pathway AKR1C3 catalyzes the NADPH dependent reduction of 5α-androstane-3,17-dione→5α-DHT. Thus AKR1C3 plays essential roles in the formation of the potent androgens that activate the AR, irrespective of the pathway responsible for their formation, FIG. 3.

In the breast, AKR1C3 catalyzes the reduction of Δ$^4$-AD to testosterone, which can undergo aromatization to form 17β-estradiol. In addition, AKR1C3 also reduces estrone to 17β-estradiol. Consistent with these activities AKR1C3 has been shown to promote proliferation of MCF-7 hormone-dependent breast cancer cells (Byrns et al., 2010, J. Steroid. Biochem. Mol. Biol. 118:177-87).

In the endometrium, AKR1C3 could increase estrogen levels and decrease progesterone levels and thus promote endometrial cancer cell proliferation (Smuc & Rizner, 2009, Mol. Cell. Endocrinol. 301:74-82).

By increasing proliferative $PGF_2$ isomers and decreasing anti-proliferative $PGJ_2$ products, the prostaglandin F synthase activities of AKR1C3 have the potential to impact both hormone-dependent and hormone-independent cancers. In particular, prostaglandin metabolism by AKR1C3 has been shown to prevent differentiation of leukemia cells and AKR1C3 inhibition is being explored as a treatment for acute myelogenous leukemia (AML) (Khanim et al., 2009, PLoS One 4 e8147).

AKR1C3 is over-expressed across a wide variety of cancers, including those of prostate and breast, and its expression increases with tumor aggressiveness (Guise et al., Cancer Res. 70:1573-84; Lin et al., 2004, Steroids 69:795-801; Stanbrough et al., 2006, Cancer Res. 66:2815-25; Hofland et al., 2010, Cancer Res. 70:1256-64; Nakamura et al., 2005, Endocrine-Related Cancer 12:101-07; Jansson et al., 2006, Cancer Res. 66:11471-77).

AKR1C3-catalyzed reactions also play important roles in other physiological and pathological processes that may be targets for therapeutic intervention. Androgen production by AKR1C3 is likely involved in the development of benign prostatic hyperplasia (Ballinan et al., 2006, Mol. Endocrinol. 20:444-58). Increased estrogen and decreased progesterone receptor signaling due to increased AKR1C3 activity could contribute to endometriosis and dysmenorrhea (Smuc et al., 2009, Mol. Cell. Endocrinol. 301:59-64). $PGF_2$ isomers formed by AKR1C3 stimulate smooth muscle contraction during parturition, while the AKR1C3 substrate progesterone prevents parturition, so AKR1C3 inhibitors may be useful as progestational agents (Breuiller-Fouche et al., Biol. Reprod. 83:155-62; Andersson et al., 2008, J. Clin. Endocrinol. Metab. 93:2366-74). Interestingly, indomethacin has proven effective at stopping premature parturition. This effect is thought to result from its inhibition of the prostaglandin G/H synthases (PGHS), but indomethacin also inhibits AKR1C3 in the same therapeutic dose range. Use of indomethacin for this purpose is limited due to side-effects in the fetus that likely stem from the inhibition of PGHS activities in developing organ systems (Loudon et al., 2003, Best Pract. Res. Clin. Obstet. Gynaecol. 17:731-44).

Because $PGF_{2\alpha}$ is involved in preventing adipocyte differentiation and $15dPGJ_2$ promotes differentiation of adipocytes, inhibiting the prostaglandin F synthase activities of AKR1C3 may have beneficial effects in diabetes similar to those observed with PPARγ agonists (Reginato et al., 1998, J. Biol. Chem. 273:1855-58; Kliewer et al., 1995, Cell 83:813-19). AKR1C3 is also involved in the metabolism of other steroids as well as prostaglandins, suggesting that AKR1C3 may be used to treat other diseases. Currently, a non-selective AKR1C3 inhibitor, 6-medroxyprogesterone acetate, is used in early clinical trials to treat AML in Europe, based on a clearly defined role of AKR1C3 in regulating the differentiation of AML cells (Khanin et al., 2009, PLoS One e1847). A selective AKR1C3 could be a promising lead for the treatment of AML.

A specific inhibitor of AKR1C3 would be a valuable tool to better understand AKR1C3 and its contribution to normal physiology and disease. One challenge in the development of an AKR1C3 inhibitor is that three other closely related enzyme isoforms (AKR1C1, AKR1C2, and AKR1C4) are also involved in steroid hormone metabolism (Penning et al., 2000, Biochem. J. 351:67-77). AKR1C4 is liver specific, while AKR1C1 and AKR1C2 are widely expressed across tissue types, including prostate. Inhibition of these three isoforms, particularly AKR1C1 and AKR1C2, is not desirable in prostate cancer as they act primarily as 3-ketosteroid reductases towards androgens. For example, AKR1C1 reduces 5α-DHT to 3β-androstanediol (a pro-apoptotic ligand of estrogen receptor β) and AKR1C2 reduces 5α-DHT to 3α-androstanediol (a weak androgen). Inhibition of these activities would promote androgen dependent proliferative signaling in the prostate and would be counterproductive.

Twenty-two crystal structures of different AKR1C3 ternary complexes have been deposited into the Protein Data Bank (Table 1) (Qiu et al., 2007, J. Biol. Chem. 282:8368-79; Komoto et al., 2004, Biochemistry 43:2188-98; Lovering et al., 2004, Cancer Res. 64:1802-10; Qiu et al., 2004, Mol. Endocrinol. 18:1798-1807; Komoto et al., 2006, Biochemistry 45:1987-96; Bennett et al., 1997, Structure 5:799-812).

TABLE 1

Available crystal structures of AKR1C3 in the Protein Data Bank.

| PDBID | Ligands | Reference |
|---|---|---|
| 1RYO | NADP$^+$, PGD$_2$ | Komoto et al., 2004, |
| 1RY8 | NADP$^+$, rutin | Biochemistry 43: 2188-98 |
| 1S1P | NADP$^+$, 2-methyl-2,4-pentanediol, acetate ion | Lovering et al., 2004, |
| 1S1R | NADP$^+$, 2-methyl-2,4-pentanediol, acetate ion | Cancer Res. 64: 1802-10 |
| 1S2A | NADP$^+$, indomethacin pH 6.0, unknown atom or ion, dimethyl sulfoxide | |
| 1S2C | NADP$^+$, flufenamic acid, dimethyl sulfoxide | |
| 1XFO | NADP$^+$, 4-androstene-3,17-dione, acetate ion | Qiu et al., 2004, Mol. Endocrinol. 18: 1798-1807 |
| 2F38 | NADP$^+$, bimatoprost | Komoto et al., 2006, Biochemistry 45: 1987-96 |

TABLE 1-continued

Available crystal structures of AKR1C3 in the Protein Data Bank.

| PDBID | Ligands | Reference |
|---|---|---|
| 1ZQ5 | NADP+, EM1404, acetate ion | Qiu et al., 2007, J. Biol. Chem. 282: 8368-79 |
| 2FGB | NADP+, hexaethylene glycol, acetate ion | |
| 3UWE | NADP+, 3-phenoxybenzoic acid, 1,2-ethanediol | Yusaatmadja et al, released May 2012 |
| 3UG8 | NADP+, indomethacin pH 7.5, 1,2-ethandiol | Yusaatmadja et al, released May 2012 |
| 3UGR | NADP+, indomethacin pH 6.8, 1,2-ethanediol | Yusaatmadja et al, released May 2012 |
| 3R58 | NADP+, Naproxen, 1,2-ethanediol | Yusaatmadja et al, released May 2012 |
| UFY | NADP+, R-Naproxen, 1,2-ethanediol | Yusaatmadja et al, released May 2012 |
| R43 | NADP+, Mefenamic acid, 1,2-ethanediol | Yusaatmadja et al, released May 2012 |
| 3R6I | NADP+, meclofenamic acid, 1,2-ethanediol | Yusaatmadja et al, released May 2012 |
| 3R94 | NADP+, flurbiprofen, 1,2-ethanediol | Yusaatmadja et al, released May 2012 |
| 3R8H | NADP+, zomepirac, 1,2-ethanediol | Yusaatmadja et al, released May 2012 |
| 3R8G | NADP+, ibuprofen, 1,2-ethanediol | Yusaatmadja et al, released May 2012 |
| 3R7M | NADP+, sulindac, 1,2-ethanediol | Yusaatmadja et al, released May 2012 |
| 4FAM | NADP+ 3-(3,4-Dihydroisoquinolin-2(1H)-ylsulfonyl)benzoic acids, 12-ethanediol | Turnbull et al., 2012 |

In the twenty two crystal structures of AKR1C3, the enzyme is complexed with the cofactor NADP+ and a second ligand. Close inspection of these structures reveals that the binding site for the second ligand is large and can be dissected into the following sub-sites: oxyanion site, steroid channel, and three sub-pockets named SP1, SP2, and SP3. One common feature of all twelve AKR1C3 structures is an occupied SP1 site (albeit to different degree), while the occupancy of other sites varies with different ligands. The occupancies of sub-sites in AKR1C3 by four inhibitors EM1404, bimatoprost, flufenamic acid, and indomethacin are depicted in FIG. 5. Understanding the binding interactions between ligands and their sub-pockets may aid inhibitor design and synthesis.

The oxyanion site refers to the conserved site that anchors the oxyanion intermediate formed during the enzyme reaction and consists of the catalytic residues Y55, H117 and NADP+ in all AKR1C enzymes (Bennett et al., 1997, Structure 5:799-812). This position is often found occupied by the oxygen atom of a carboxylic acid, ketone, or hydroxyl group of a ligand. Strong hydrogen bonding interactions form between the occupant and Y55 and H117 (2.6 Å and 2.8 Å, respectively). The positioning of the carbonyl group of a substrate at the oxyanion site is believed to be essential for productive binding since the anchoring brings the carbonyl group in proximity to the cofactor, allowing the reaction to proceed (Bennett et al., 1997, Structure 5:799-812; Jin & Penning, 2006, Steroids 71:380-91; Jin et al., 2001, Biochemistry 40:10161-68). Similarly, it is believed that the binding of the carboxylate or ketone group of an NSAID at the oxyanion site explains the general inhibition of AKR1C enzymes by NSAIDs. For example, the carboxylic acid moiety of flufenamic acid is anchored at the oxyanion site of AKR1C3, while the bridge carbonyl group of indomethacin at pH 6.0 binds via an unidentified atom to the oxyanion site of the enzyme (FIGS. 5C and 5D). At pH 7.0, indomethacin rotates so that its crabxylate is now tethered to the oxyanion site. Interestingly, the oxyanion site does not appear to significantly contribute to the binding of EM1404 and bimatoprost (FIGS. 5A and 5B) in AKR1C3, as the site was occupied by an acetate ion and a water molecule, respectively in the crystal structures of the AKR1C3.NADP+.EM1404 and AKR1C3.NADP+.bimatoprost complexes (Komoto et al., 2006, Biochemistry 45:1987-96).

The steroid channel refers to the elongated open channel that is also conserved in all AKR1C enzymes (Bennett et al., 1997, Structure 5:799-812). W227 and L/V54 are important gate keepers for the steroid channel and determine the positional and stereochemical specificities of the steroid transforming activity of AKR1C enzymes (Jin et al., 2001, Biochem. 40:10161-68). Interestingly, the steroid channel does not appear to be an important inhibitor binding site for AKR1C3. With the exception of EM1404, which has its steroid ring structure partially occupying the steroid channel, this channel is left empty by bimatoprost, flufenamic acid, and indomethacin (FIG. 5).

The SP1 sub-pocket is formed by residues S118, N167, F306, F311, and Y319 in AKR1C3, and is the only site that is occupied in all available crystal structures of this enzyme. As such, it accommodates the lactone moiety of EMI404 (FIG. 5A), the 12β-chain of PGD$_2$, the 8α-chain of bimatoprost (FIG. 5B), or the —CF$_3$ substituted B-ring of flufenamic acid (FIG. 5C). The p-chlorobenzoyl group of indomethacin also projects into this site, although in that structure a solvent molecule from the crystallization solution (dimethyl sulfoxide) was bound in the bottom of SP1 (FIG. 5D).

The SP2 sub-pocket refers to a pocket formed by residues W86, S129, W227 and F311 in AKR1C3. This pocket is where the 8α-chain of PGD$_2$ and the 12β-chain of bimatoprost were bound (Komoto et al., 2004, Biochemistry 43:2188-98). It appears that this sub-pocket is only used by the two prostanoids.

The SP3 sub-pocket refers to a large pocket lined by residues Y24, E192, S217, S221, Q222, Y305, and F306 in AKR1C3. These residues surround the indole ring and the carboxylate group of the indomethacin molecule at pH 6.0. SP3 is not occupied by other ligands in AKR1C3.

The variety of AKR1C3 ligands in structure and size demonstrate the flexibility of the enzyme's ligand binding site. The key residues to AKR1C3's ability to accommodate different ligands are W227, F306, and F311. These residues can assume different conformations and result in "induced-fit" to various ligands. W227 controls the sizes of SP2 and the steroid channel. F306 lines the SP1 site for the AKR1C3-NADP+-flufenamic acid complex, but assumes a different rotamer conformation in the crystal of the AKR1C3-NADP+-indomethacin complex, thereby exposing the SP3 pocket. F311 forms part of SP1 for the binding of flufenamic acid, but lines SP2 for the binding of bimatoprost and PGD$_2$.

Comparison of the ligand binding sites of AKR1C 1-4 reveals that there are considerable structural differences in sub-pockets between AKR1C3 and the other isoforms (Couture et al., 2003, J. Mol. Biol. 331:593-604). SP1 is significantly larger for AKR1C3. The difference in the size of SP1 is largely due to the shift in main chain positions of residues 305-311 between AKR1C3 and the other enzymes (FIG. 6A). As a result, residue 308 collapses inward and significantly reduces the size of SP1 for AKR1C1, AKR1C2 and AKR1C4. In AKR1C3 the side chain of S308 is not involved in ligand binding (>4 Å), but the corresponding residues of L308 in AKR1C2 and M308 in AKR1C4 would extend into SP1. In addition, different residues at positions 118 and 319 also reduce the size of SP1 in AKR1C ½ and AKR1C4. In AKR1C3, the side-chains of S118 and Y319 are >4 Å away from the ligand, whereas the corresponding residues of F118 (1.7 Å) and F319 (~1 Å) in AKR1C2 would clash with a long ligand such as PGD$_2$ or bimatoprost (Komoto et al., 2006, Biochem. 45:1987-96). Importantly, the serine residue at position 118 in AKR1C3 is capable of forming hydrogen-bonding interactions with a ligand, i.e., with the amide group of the 8α-chain of bimatoprost (Komoto et al., 2006, Biochem. 45:1987-96). In contrast, the corresponding residue for AKR1C1, AKR1C2 and AKR1C4 is a phenylalanine incapable of hydrogen bonding with a ligand.

No ligands have been observed to occupy the SP2 site in crystals of AKR1C1, AKR1C2, or AKR1C4. Comparison of the SP2 sites of these enzymes shows structural differences at position 129 and 311 that make the SP2 pocket shorter for AKR1C1, AKR1C2, and AKR1C4 than that for AKR1C3 (FIG. 6B). In addition, S129 of AKR1C3 can form hydrogen-bonding interactions with a ligand, i.e., with the carboxylate group of the 8α-chain of PGD$_2$ or with the hydroxyl group on 12β-chain of bimatoprost (Komoto et al., 2006, Biochem. 45:1987-96). In contrast, the corresponding residues in other isoforms—I129 for AKR1C1 and AKR1C2 and L129 for AKR1C4—are incapable of hydrogen bonding with a ligand.

Structural differences at position 306 also cause the SP3 site of AKR1C3 to differ from those for the other enzymes (FIG. 6C). In the AKR1C3-NADP+-indomethacin complex at pH 6.0, the side chain of F306 assumes a conformation that points away from the ligand. However, the corresponding residues L306 of AKR1C1 and AKR1C2 and V306 of AKR1C4 have more rigid side chains that would clash with the indole ring of indomethacin.

Despite the availability of structural information, there has been no report to date of an AKR1C3 inhibitor that does not inhibit AKR1C1 and AKR1C2 and has good developmental properties. Such a selective inhibitor is needed to explore the role of AKR1C3 in normal and aberrant cell signaling. Such a selective compound may find use in treating CRPC through the inhibition of AKR1C3. There is thus a need in the art to identify novel inhibitors of AKR1C3 that show selectivity over AKR1C1 or AKR1C2. The present invention fulfills this need.

BRIEF SUMMARY OF THE INVENTION

In one aspect, the invention includes a composition comprising a compound of Formula (I) or a salt thereof:

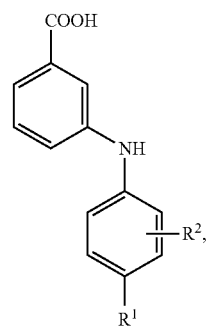

(I)

wherein:
R$^1$ is selected from the group consisting of C$_1$-C$_6$ alkyl, haloalkyl, halo, nitro, —CN, C$_1$-C$_6$ alkoxy, —C(C═O)H, —C(C═O)OH, —C(C═O)—(C$_1$-C$_6$ alkyl), and —SO$_3$H; and, each occurrence of R$^2$ is independently selected from the group consisting of H, C$_1$-C$_6$ alkyl, haloalkyl, halo, nitro, —CN, C$_1$-C$_6$ alkoxy, —C(C═O)H, —C(C═O)OH, —C(C═O)—(C$_1$-C$_6$ alkyl), and —SO$_3$H.

In one embodiment, R$^1$ is selected from the group consisting of methyl, tert-butyl, methoxy, fluoro, chloro, bromo, trifluoromethyl, nitro and acetyl. In another embodiment, each occurrence of R$^2$ is independently selected from the group consisting of H, methyl, tert-butyl, methoxy, fluoro, chloro, bromo, trifluoromethyl, nitro and acetyl. In yet another embodiment, the compound of Formula (I) is selected from the group consisting of 3-[N-(4-nitrophenyl)amino]benzoic acid, 3-[N-(4-acetylphenyl)amino]benzoic acid, 3-[N-(4-trifluoromethylphenyl)amino]benzoic acid, 3-[N-(4-chlorophenyl)amino]benzoic acid, 3-[N-(4-bromophenyl)amino]benzoic acid, 3-[N-(4-tert-butylphenyl)amino]benzoic acid, 3-[N-(4-methoxyphenyl)amino]benzoic acid, 3-[N-(4-methylphenyl)amino]benzoic acid, mixtures thereof and salts thereof.

In one aspect, the invention includes a composition comprising a compound of Formula (II) or a salt thereof where the naphthyl ring can be alpha or beta substituted:

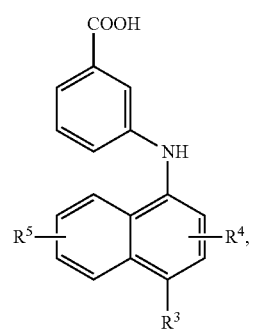

(II)

wherein:
R$^3$ is selected from the group consisting of C$_1$-C$_6$ alkyl, haloalkyl, halo, nitro, —CN, C$_1$-C$_6$ alkoxy, —C(C═O)H, —C(C═O)OH, —C(C═O)—(C$_1$-C$_6$ alkyl), and —SO$_3$H; and, each occurrence of $R^4$ and $R^5$ is independently selected from the group consisting of H, $C_1$-$C_6$ alkyl, haloalkyl, halo, nitro, —CN, $C_1$-$C_6$ alkoxy, —C(C=O)H, —C(C=O)OH, —C(C=O)—($C_1$-$C_6$ alkyl), and —$SO_3$H.

In one embodiment, $R^3$ is selected from the group consisting of methyl, tert-butyl, methoxy, fluoro, chloro, bromo, trifluoromethyl, nitro and acetyl. In another embodiment, each occurrence of $R^4$ is independently selected from the group consisting of H, methyl, tert-butyl, methoxy, fluoro, chloro, bromo, trifluoromethyl, nitro and acetyl. In yet another embodiment, each occurrence of $R^5$ is independently selected from the group consisting of H, methyl, tert-butyl, methoxy, fluoro, chloro, bromo, trifluoromethyl, nitro and acetyl. In yet another embodiment, the compound of Formula (II) is 3-((4-nitronaphthalen-1-yl)amino)benzoic acid or a salt thereof.

In one embodiment, the composition further comprises a pharmaceutically acceptable carrier. In another embodiment, the composition further comprises at least one therapeutic agent selected from the group consisting of indomethacin, desatinib, selegiline, seliciclib, TOK-001, SAHA, docetaxel, bevacizumab, taxotere, thalidomide, prednisone, Sipuleucel-T, cabazitaxel, MDV3100, ARN-509, abiraterone, temozolomide, tamoxifen, anastrozole, letrozole, vorozole, exemestane, fadrozole, formestane, raloxifene, mixtures thereof and salts thereof.

In one aspect, the invention includes a method of treating, ameliorating or preventing cancer in a subject in need thereof. The method comprises administering to the subject a composition comprising a pharmaceutically acceptable carrier and a therapeutically effective amount of at least one compound selected from the group consisting of:

(i) a compound of Formula (I):

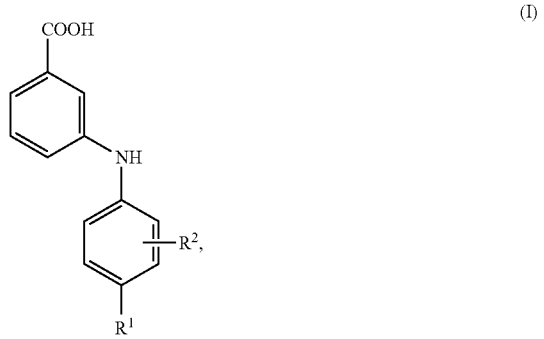

wherein:

$R^1$ is selected from the group consisting of $C_1$-$C_6$ alkyl, haloalkyl, halo, nitro, —CN, $C_1$-$C_6$ alkoxy, —C(C=O)H, —C(C=O)OH, —C(C=O)—($C_1$-$C_6$ alkyl), and —$SO_3$H; and, each occurrence of $R^2$ is independently selected from the group consisting of H, $C_1$-$C_6$ alkyl, haloalkyl, halo, nitro, —CN, $C_1$-$C_6$ alkoxy, —C(C=O)H, —C(C=O)OH, —C(C=O)—($C_1$-$C_6$ alkyl), and —$SO_3$H; and, (ii) a compound of Formula (II) where the naphthyl ring can be alpha or beta substituted:

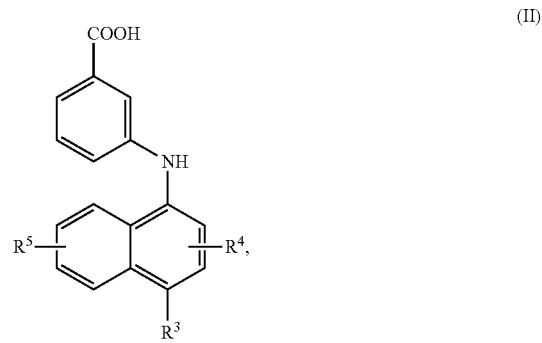

wherein:

$R^3$ is selected from the group consisting of $C_1$-$C_6$ alkyl, haloalkyl, halo, nitro, —CN, $C_1$-$C_6$ alkoxy, —C(C=O)H, —C(C=O)OH, —C(C=O)—($C_1$-$C_6$ alkyl), and —$SO_3$H; and, each occurrence of $R^4$ and $R^5$ is independently selected from the group consisting of H, $C_1$-$C_6$ alkyl, haloalkyl, halo, nitro, —CN, $C_1$-$C_6$ alkoxy, —C(C=O)H, —C(C=O)OH, —C(C=O)—($C_1$-$C_6$ alkyl), and —$SO_3$H;

mixtures thereof and salts thereof, whereby the administering treats, ameliorates or prevents the cancer in the subject, wherein the cancer is selected from the group consisting of prostate cancer, breast cancer, endometrial cancer, acute myelogenous leukemia, and combinations thereof.

In one embodiment, the prostate cancer comprises castrate resistant prostate cancer. In another embodiment, the cancer is androgen dependent. In yet another embodiment, the cancer is prostate cancer and the method further comprises administering to the subject at least one therapeutic agent selected from the group consisting of indomethacin, desatinib, selegiline, seliciclib, TOK-001, SAHA, docetaxel, bevacizumab, taxotere, thalidomide, prednisone, Sipuleucel-T, cabazitaxel, MDV3100, ARN-509, abiraterone, temozolomide, mixtures thereof and salts thereof. In yet another embodiment, the composition and the at least one therapeutic agent are administered concomitantly to the subject. In yet another embodiment, the composition and the at least one therapeutic agent are co-formulated. In yet another embodiment, the cancer is breast cancer and the method further comprises administering to the subject at least one therapeutic agent selected from the group consisting of tamoxifen, anastrozole, letrozole, vorozole, exemestane, fadrozole, formestane, raloxifene, mixtures thereof and salts thereof. In yet another embodiment, the composition and the at least one therapeutic agent are administered concomitantly to the subject. In yet another embodiment, the composition and the at least one therapeutic agent are co-formulated. In yet another embodiment, the subject is a human.

In one aspect, the invention includes a method of treating, ameliorating or preventing a condition or disease in a subject in need thereof. The method comprising administering to the subject a composition comprising a pharmaceutically acceptable carrier and a therapeutically effective amount of at least one compound selected from the group consisting of:

(i) a compound of Formula (I):

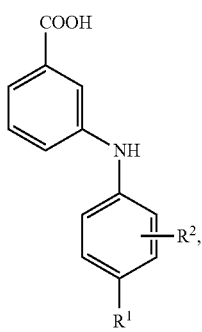
(I)

wherein:
R$^1$ is selected from the group consisting of C$_1$-C$_6$ alkyl, haloalkyl, halo, nitro, —CN, C$_1$-C$_6$ alkoxy, —C(C=O)H, —C(C=O)OH, —C(C=O)—(C$_1$-C$_6$ alkyl), and —SO$_3$H; and, each occurrence of R$^2$ is independently selected from the group consisting of H, C$_1$-C$_6$ alkyl, haloalkyl, halo, nitro, —CN, C$_1$-C$_6$ alkoxy, —C(C=O)H, —C(C=O)OH, —C(C=O)—(C$_1$-C$_6$ alkyl), and —SO$_3$H; and, (ii) a compound of Formula (II) where the naphthyl ring can be alpha or beta substituted:

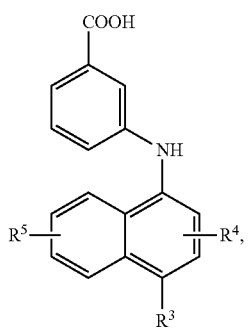
(II)

wherein:
R$^3$ is selected from the group consisting of C$_1$-C$_6$ alkyl, haloalkyl, halo, nitro, —CN, C$_1$-C$_6$ alkoxy, —C(C=O)H, —C(C=O)OH, —C(C=O)—(C$_1$-C$_6$ alkyl), and —SO$_3$H; and, each occurrence of R$^4$ and R$^5$ is independently selected from the group consisting of H, C$_1$-C$_6$ alkyl, haloalkyl, halo, nitro, —CN, C$_1$-C$_6$ alkoxy, —C(C=O)H, —C(C=O)OH, —C(C=O)—(C$_1$-C$_6$ alkyl), and —SO$_3$H;

mixtures thereof and salts thereof, wherein the condition or disease is selected from the group consisting of diabetes, premature parturition, endometriosis, dysmenorrhea, benign prostate hyperplasia and combinations thereof, whereby the administering treats, ameliorates or prevents said condition or disease in the subject. In one embodiment, the subject is a human.

In one aspect, the invention includes a method of treating, ameliorating or preventing a condition or disease in a subject in need thereof. The method comprising administering to the subject a composition comprising a pharmaceutically acceptable carrier and a therapeutically effective amount of at least one compound selected from the group consisting of:

(i) a compound of Formula (I):

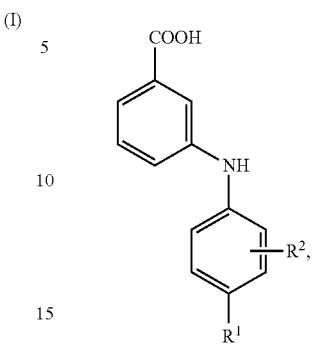
(I)

wherein:
R$^1$ is selected from the group consisting of C$_1$-C$_6$ alkyl, haloalkyl, halo, nitro, —CN, C$_1$-C$_6$ alkoxy, —C(C=O)H, —C(C=O)OH, —C(C=O)—(C$_1$-C$_6$ alkyl), and —SO$_3$H; and, each occurrence of R$^2$ is independently selected from the group consisting of H, C$_1$-C$_6$ alkyl, haloalkyl, halo, nitro, —CN, C$_1$-C$_6$ alkoxy, —C(C=O)H, —C(C=O)OH, —C(C=O)—(C$_1$-C$_6$ alkyl), and —SO$_3$H; and, (ii) a compound of Formula (II): where the naphthyl ring can be alpha or beta substituted

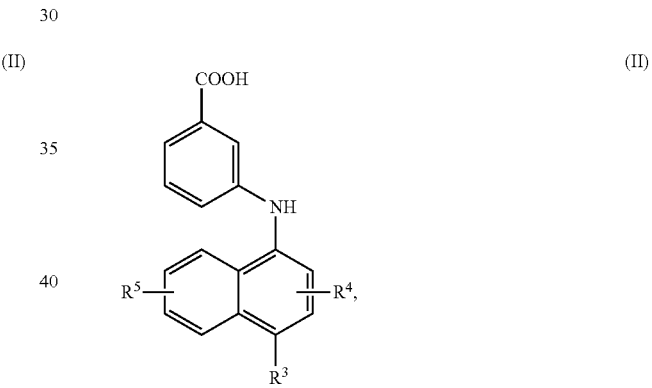
(II)

wherein:
R$^3$ is selected from the group consisting of C$_1$-C$_6$ alkyl, haloalkyl, halo, nitro, —CN, C$_1$-C$_6$ alkoxy, —C(C=O)H, —C(C=O)OH, —C(C=O)—(C$_1$-C$_6$ alkyl), and —SO$_3$H; and, each occurrence of R$^4$ and R$^5$ is independently selected from the group consisting of H, C$_1$-C$_6$ alkyl, haloalkyl, halo, nitro, —CN, C$_1$-C$_6$ alkoxy, —C(C=O)H, —C(C=O)OH, —C(C=O)—(C$_1$-C$_6$ alkyl), and —SO$_3$H;

mixtures thereof and salts thereof, wherein the condition or disease is dependent on a tissue-specific androgen effect, whereby the administering treats, ameliorates or prevents said condition or disease in the subject.

In one embodiment, the at least one compound is a selective androgen receptor modulator. In another embodiment, the condition or disease is selected from the group consisting of alopecia, hirsutism, muscle wasting, cancer cachexia, aplastic anemia, osteoporosis, male andropause, and combinations thereof. In yet another embodiment, the subject is a human.

In one aspect, the invention includes a method of achieving a tissue-specific effect in a male subject in need thereof. The method comprises administering to the subject a composition comprising a pharmaceutically acceptable carrier and a therapeutically effective amount of at least one compound selected from the group consisting of:

(i) a compound of Formula (I):

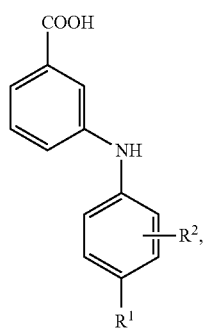

(I)

wherein:

$R^1$ is selected from the group consisting of $C_1$-$C_6$ alkyl, haloalkyl, halo, nitro, —CN, $C_1$-$C_6$ alkoxy, —C(C=O)H, —C(C=O)OH, —C(C=O)—($C_1$-$C_6$ alkyl), and —SO$_3$H; and, each occurrence of $R^2$ is independently selected from the group consisting of H, $C_1$-$C_6$ alkyl, haloalkyl, halo, nitro, —CN, $C_1$-$C_6$ alkoxy, —C(C=O)H, —C(C=O)OH, —C(C=O)—($C_1$-$C_6$ alkyl), and —SO$_3$H; and, (ii) a compound of Formula (II) where the naphthyl ring can be alpha or beta substituted:

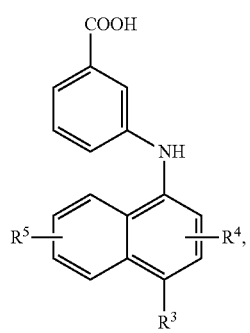

(II)

wherein:

$R^3$ is selected from the group consisting of $C_1$-$C_6$ alkyl, haloalkyl, halo, nitro, —CN, $C_1$-$C_6$ alkoxy, —C(C=O)H, —C(C=O)OH, —C(C=O)—($C_1$-$C_6$ alkyl), and —SO$_3$H; and, each occurrence of $R^4$ and $R^5$ is independently selected from the group consisting of H, $C_1$-$C_6$ alkyl, haloalkyl, halo, nitro, —CN, $C_1$-$C_6$ alkoxy, —C(C=O)H, —C(C=O)OH, —C(C=O)—($C_1$-$C_6$ alkyl), and —SO$_3$H; mixtures thereof and salts thereof, whereby the administering treats, ameliorates or prevents the condition or disease in said subject.

In one embodiment, the effect comprises an anabolic effect or erythropoiesis. In another embodiment, the at least one compound is a selective androgen receptor modulator. In yet another embodiment, the subject is a human.

In one embodiment, the compound of Formula (I) is selected from the group consisting of 3-[N-(4-nitrophenyl)amino]benzoic acid, 3-[N-(4-acetylphenyl)amino]benzoic acid, 3-[N-(4-trifluoromethylphenyl)amino]benzoic acid, 3-[N-(4-chlorophenyl)amino]benzoic acid, 3-[N-(4-bromophenyl)amino]benzoic acid, 3-[N-(4-tert-butylphenyl)amino]benzoic acid, 3-[N-(4-methoxyphenyl)amino]-benzoic acid, 3-[N-(4-methylphenyl)amino]benzoic acid, mixtures thereof and salts thereof. In another embodiment, the compound of Formula (II) is 3-((4-nitronaphthalen-1-yl)amino)benzoic acid or a salt thereof.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 2 is an illustration of reactions catalyzed by AKR1C3.

FIG. 4 illustrates the chemical structures of representative AKR1C3 inhibitors and their inhibitory potency towards AKR1C3 and closely related isoforms AKR1C1 and AKR1C2. ND, not determined.

FIGS. 5A-5D, illustrates the occupancies of AKR1C3 ligand binding sub-sites by inhibitors EM1404, bimatoprost, flufenamic acid, and indomethacin (A through D). SC=steroid channel; OS=oxyanion site; ACT=acetate ion; HOH=water; BMP=bimatoprost; FLF=flufenamic acid; OMS=dimethyl sulfoxide; IMN=indomethacin; UNX=unknown atom or ion; SP1-3=sub-pockets 1-3. In FIG. 5A, the lactone portion of EM1404 is bound in SP1 while the estrone portion extends into the steroid channel (PDB ID: 1ZQ5). In FIG. 5B, the α-chain of bimatoprost is bound in SP1 while the β-chain of the inhibitor is bound in SP2 (PDB ID: 2F38). In FIG. 5C, the trifluoromethyl substituted B-ring of flufenamic acid is located in SP1 and the carboxylic acid moiety of the molecule is anchored at the oxyanion site (PDB ID: 1S2C). In FIG. 5D, the bridge carbonyl group of indomethacin is positioned via an unknown atom located at the oxyanion site. The p-chlorobenzoyl group of indomethacin projects into SP1, while the indole ring and carboxylic acid is bound in the well-defined SP3 (PDB ID: 1 S2A). Ligands are depicted in ball-and-stick representation.

FIGS. 6A-6C, illustrates the comparison of SP1, SP2, and SP3 sub-pockets of four human AKR1C enzymes. The crystal structures used for comparisons are AKR1C1-NADP$^+$-20α-hydroxyprogesterone (PDB ID: 1MRQ), AKR1C2-NADPtursodeoxycholate (PDB ID: 1IHI), and AKR1C4-NADP$^+$ (PDB ID: 2FVL). The respective AKR1C3 structures in FIGS. 6A-6C are AKR1C3-NADP$^+$-flufenamic acid (PDB ID: 1S2C, for comparison of SP1), AKR1C3-NADP+-bimatoprost (PDB ID: 2F38, for comparison of SP2) and AKR1C3-NADP+-indomethacin pH 6.0 (PDB ID: 1S2A, for comparison of SP3). The residues are shown in stick presentation. For clarity, only key residues for binding are shown and are labeled by the number and their respective identities. AKR1C1 has the same residues as AKR1C2 at all positions shown. FLF=flufenamic acid, BMP=bimatoprost, and IMN=indomethacin. FIG. 6A: AKR1C3 has a larger SP1 site than the other isoforms due to a different main chain position at 308 and different residues at 118. In addition, S118 of AKR1C3 can form a side chain hydrogen bonding interaction with a ligand, whereas the corresponding residue F118 in other isoforms cannot. FIG. 6B: structural differences at positions 129 and 311 make the SP2 pocket shorter for AKR1C1, AKR1C2 and AKR1C4 than for AKR1C3. S129 of AKR1C3 can form side chain hydrogen bonding interactions with a ligand, whereas the corresponding I129 of AKR1C ½ and L129 of AKR1C4 cannot. FIG. 6C: the side chain of F306 in AKR1C3 assumes a conformation that exposes the SP3 site for indomethacin binding. However, the corresponding L306 of AKR1C ½ and V306 for AKR1C4 with more rigid side chains would extend into the indole ring of indomethacin.

FIG. 8, comprising FIGS. 8A-8B, illustrates compound structure and inhibitory potency on AKR1C2 and AKR1C3 for Compounds 1-12.

FIGS. 12A-12B, is a reproduction of an electrophoretic gel illustrating the specificity of the monoclonal Ab for AKR1C3. FIG. 12A: Homogeneous recombinant AKRs (3.5 µg) separated by SDS-PAGE were subjected to immunoblot analysis using a 1 in 1,000 dilution of the AKR1C3 mAb. FIG. 12B: Coomassie Blue staining.

FIG. 17 is a table illustrating compounds to be used in xenograft studies.

FIG. 18 is a table illustrating the regulation of nuclear receptors by human AKRs.

FIG. 26, comprising

FIG. 30 is a table illustrating the selectivity of compounds recited in the application to inhibit AKR1C3 over other human AKR enzymes FIG. 31 illustrates the inability of compounds recited in the application to inhibit COX-1 or COX-2.

FIGS. 37A-37C, is a schematics illustrating the occupancy of the AKR1C3 steroid binding sub-pockets (SP1, SP2, and SP3) by compound 7 (FIG. 37A), compound 1 (FIG. 37B), and compound 13 (FIG. 37C). Compound 7, Compound 1, and the first molecule of compound 13 were tethered to the oxyanion site (OS) by hydrogen bonds between the carboxylate group and Tyr55 and His 117. The N-phenylamino/naphthylamino rings of the inhibitors projected to the SP1 pocket. The second molecule of compound 13 stacked against the first one in the SP1 pocket by overlapping the N-naphthylamino ring, but its N-benzoic acid ring extended to the steroid channel (SC) that opened to the solvent. The simulated-annealing omit map of compound 7 was contoured at 2.5r and the map of compound 13 was contoured at 2.3r. Water molecules were shown as red spheres. Hydrogen bonds were indicated by dashes.

FIG. 38 summarizes data collection and refinement statistics.

FIG. 39, comprising

DETAILED DESCRIPTION OF THE INVENTION

This invention includes the unexpected discovery of novel inhibitors of AKR1C3. The inhibitors of the invention exhibit selectivity for AKR1C3 over the enzymes AKR1C1 and AKR1C2, as well as COX-1 and COX-2 (otherwise known as Prostaglandin G/H synthases or PGHS). The inhibitors identified herein also modulate the androgen receptor (AR), which plays an important role in cell proliferation, and thus are dual selective AKR1C3 inhibitors/AR modulators.

Figure 10:
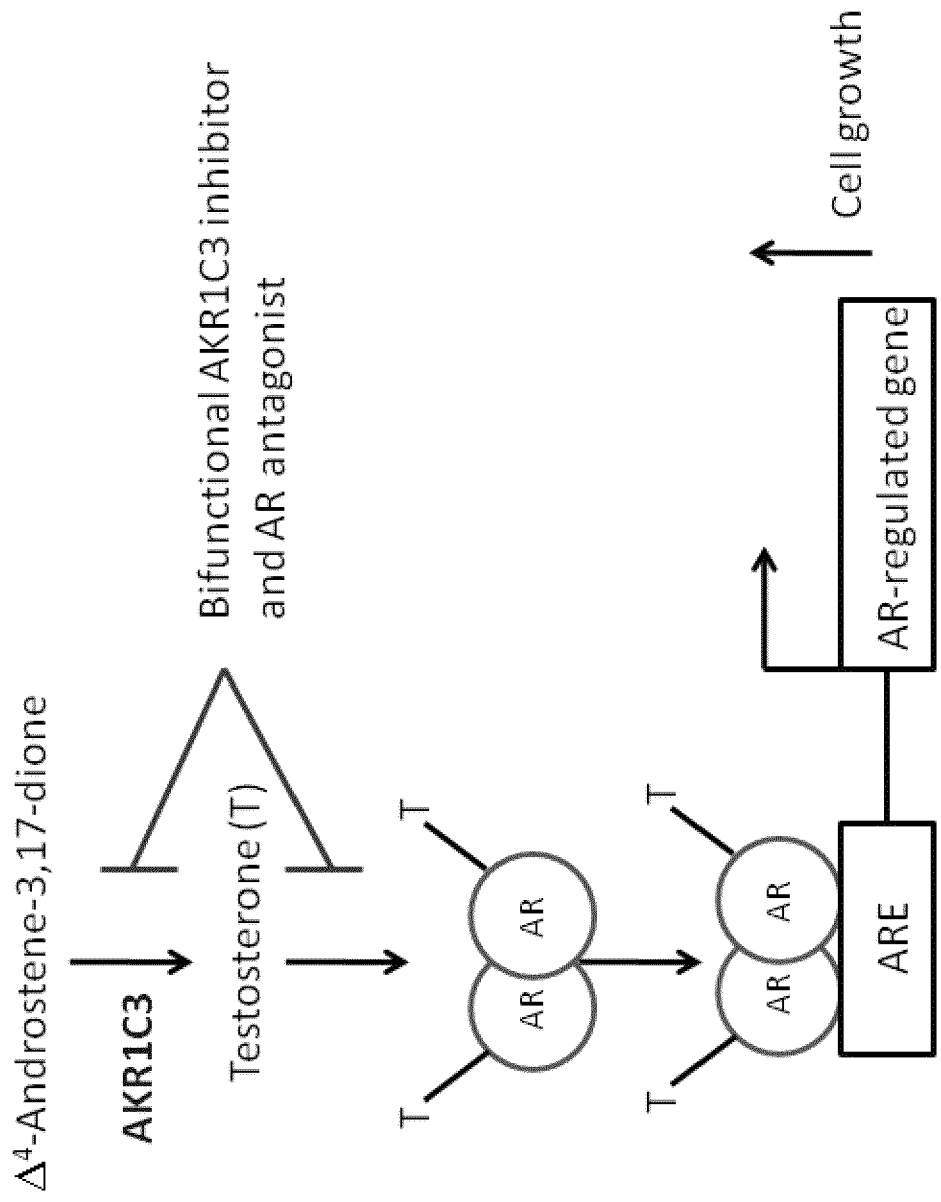
FIG. 10 illustrates the action of a bifunctional AKR1C3 inhibitor and AR antagonist on AR mediated cell growth in the prostate. AR=androgen receptor, ARE=androgen responsive element.

In one aspect, the inhibitors of the invention find use in the treatment of androgen-driven proliferative disorders or diseases, such as but not limited to benign prostatic hyperplasia and prostate cancer, including but not limited to castrate resistant prostate cancer. In another aspect, the inhibitors of the invention find use in the treatment of estrogen dependent malignancies such as breast and endometrial cancer. In yet another aspect, the inhibitors of this invention find use in the treatment, amelioration or prevention of diabetes, premature parturition, endometriosis, dysmenorrhea, and AML. In a non-limiting embodiment, the action of a bifunctional AKR1C3 inhibitor and SARM on AR mediated cell growth in the prostate is illustrated in FIG. 10. In another non-limiting embodiment, the inhibitors of the invention are selective androgen receptor modulators.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in biochemistry, analytical chemistry and organic chemistry are those well-known and commonly employed in the art. Standard techniques or modifications thereof are used for chemical syntheses and chemical analyses.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent on the context in which it is used. As used herein, "about" when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "PC" refers to prostate cancer. As used herein, the term "ADT" refers to androgen deprivation therapy. As used herein, the term "CRPC" refers to castrate resistant prostate cancer. As used herein, the term "AR" refers to the androgen receptor. As used herein, the term "ARE" refers to androgen responsive element. As used herein, the term "AML" refers to acute myeloid leukemia. As used herein, the term "3β-HSD/KSI refers to 3β-hydroxysteroid dehydrogenase/ketosteroid isomerase. As used herein, the term "3β-Adiol" refers to 5α-androstane-3β,17β-diol or a salt thereof. As used herein, the term "3α-Adiol" refers to 5α-androstane-3α,17β-diol or a salt thereof. As used herein, the term "ERβ" refers to estrogen receptor β. As used herein, the terms SP1, SP2 and SP3 refers to sub-pockets 1-3, respectively.

As used herein, the term "receptor modulator" refers to a molecule or peptide that binds to at least one receptor in the body, affecting its activity, function or biological response. In some embodiments, a receptor modulator may act as an agonist, antagonist or inverse agonist. In some embodiments, the activity of a receptor modulator is dependent on the tissue localization of the receptor.

As used herein, the term "SARM" refers to selective androgen receptor modulator. As used herein, the term "SERM" refers to selective estrogen receptor modulator.

An "amino acid" as used herein is meant to include both natural and synthetic amino acids, and both D and L amino acids. "Standard amino acid" means any of the twenty L-amino acids commonly found in naturally occurring peptides. "Nonstandard amino acid residues" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides, and particularly at the carboxy- or amino-terminus, can be modified by methylation, amidation, acetylation or substitution with other chemical groups which can change a peptide's circulating half-life without adversely affecting activity of the peptide. Additionally, a disulfide linkage may be present or absent in the peptides.

As used herein, the terms "protein", "peptide" and "polypeptide" are used interchangeably, and refer to a compound comprised of amino acid residues covalently linked by peptide bonds. The term "peptide bond" means a covalent amide linkage formed by loss of a molecule of water between the carboxyl group of one amino acid and the amino group of a second amino acid. A protein or peptide must contain at least two amino acids, and no limitation is placed on the maximum number of amino acids that may comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Proteins" include, for example, biologically active fragments, substantially homologous proteins, oligopeptides, homodimers, heterodimers, protein variants, modified proteins, derivatives, analogs, and fusion proteins, among others. The proteins include natural proteins, recombinant proteins, synthetic proteins, or a combination thereof. A protein may be a receptor or a non-receptor.

As used herein, the term "fragment," as applied to a protein or peptide, refers to a subsequence of a larger protein or peptide. A "fragment" of a protein or peptide may be at least about 20 amino acids in length; for example at least about 50 amino acids in length; at least about 100 amino acids in length, at least about 200 amino acids in length, at least about 300 amino acids in length, and at least about 400 amino acids in length (and any integer value in between).

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). The term "nucleic acid" typically refers to large polynucleotides.

The term "DNA" as used herein is defined as deoxyribonucleic acid. The term "RNA" as used herein is defined as ribonucleic acid. The term "recombinant DNA" as used herein is defined as DNA produced by joining pieces of DNA from different sources.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides, at least about 1000 nucleotides to about 1500 nucleotides; or about 1500 nucleotides to about 2500 nucleotides; or about 2500 nucleotides (and any integer value in between).

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T."

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the term "alkyl," by itself or as part of another substituent means, unless otherwise stated, a straight or branched chain hydrocarbon having the number of carbon atoms designated (i.e. $C_{1-6}$ or $C_1$-$C_6$ means one to six carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$)alkyl, particularly ethyl, methyl, isopropyl, isobutyl, n-pentyl, n-hexyl and cyclopropylmethyl.

As used herein, the term "substituted alkyl" means alkyl, as defined above, substituted by one, two or three substituents selected from the group consisting of halogen, —OH, alkoxy, —$NH_2$, —$N(CH_3)_2$, —C(C═O)OH, trifluoromethyl, —C≡N, —C(C═O)O($C_1$—C4)alkyl, —C(C═O)$NH_2$, —$SO_2NH_2$, —C(═NH)$NH_2$, and —$NO_2$, preferably containing one or two substituents selected from halogen, —OH, alkoxy, —NH₂, trifluoromethyl, —N(CH₃)₂, and —C(C=O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are (C₁-C₃) alkoxy, particularly ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH₂—CH₂—CH₃, —CH₂—CH₂—CH₂—OH, —CH₂—CH₂—NH—CH₃, —CH₂—S—CH₂—CH₃, and —CH₂CH₂—S(=O)—CH₃. Up to two heteroatoms may be consecutive, such as, for example, —CH₂—NH—OCH₃, or —CH₂—CH₂—S—S—CH₃

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Preferred are phenyl and naphthyl, most preferred is phenyl.

As used herein, the term "aryl-(C₁-C₃)alkyl" means a functional group wherein a one to three carbon alkylene chain is attached to an aryl group, e.g., —CH₂CH₂-phenyl. Preferred is aryl-CH₂— and aryl-CH(CH₃)—. The term "substituted aryl-(C₁-C₃)alkyl" means an aryl-(C₁-C₃)alkyl functional group in which the aryl group is substituted. Preferred is substituted aryl(CH₂)—. Similarly, the term "heteroaryl-(C₁-C₃)alkyl" means a functional group wherein a one to three carbon alkylene chain is attached to a heteroaryl group, e.g., —CH₂CH₂-pyridyl. Preferred is heteroaryl-(CH₂)—. The term "substituted heteroaryl-(C₁-C₃)alkyl" means a heteroaryl-(C₁-C₃)alkyl functional group in which the heteroaryl group is substituted. Preferred is substituted heteroaryl-(CH₂)—.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group.

For aryl, aryl-(C₁-C₃)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. In yet another embodiment, the substituents are independently selected from the group consisting of C₁₋₆ alkyl, —OH, C₁₋₆ alkoxy, halo, amino, acetamido and nitro. In yet another embodiment, the substituents are independently selected from the group consisting of C₁₋₆ alkyl, C₁₋₆ alkoxy, halo, acetamido, and nitro. As used herein, where a substituent is an alkyl or alkoxy group, the carbon chain may be branched, straight or cyclic, with straight being preferred.

By the term "specifically binds," as used herein, is meant a molecule, such as an antibody or a small molecule, which recognizes and binds to another molecule or feature, but does not substantially recognize or bind other molecules or features in a sample.

The phrase "inhibit," as used herein, means to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists or inverse agonists.

"Effective amount" or "therapeutically effective amount" are used interchangeably herein, and refer to an amount of a compound, formulation, material, or composition, as described herein effective to achieve a particular biological result. Such results may include, but are not limited to, the treatment of a disease or condition as determined by any means suitable in the art.

As used herein, the term "pharmaceutical composition" refers to a mixture of at least one compound of the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to, intravenous, oral, aerosol, parenteral, ophthalmic, pulmonary and topical administration.

"Pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "salt" embraces addition salts of free acids or free bases that are compounds useful within the invention. Suitable acid addition salts may be prepared from an inorganic acid or from an organic acid. Examples of inorganic acids include hydrochloric, hydrobromic, hydriodic, nitric, carbonic, sulfuric, phosphoric acids, perchloric and tetrafluoroboronic acids. Appropriate organic acids may be selected from aliphatic, cycloaliphatic, aromatic, arylaliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Suitable base addition salts of compounds useful within the invention include, for example, metallic salts including alkali metal, alkaline earth metal and transition metal salts such as, for example, lithium, calcium, magnesium, potassium, sodium and zinc salts. Acceptable base addition salts also include organic salts made from basic amines such as, for example, N,N'-dibenzylethylenediamine, chloroprocaine, choline, diethanolamine, ethylenediamine, meglumine (N-methylglucamine) and procaine. All of these salts may be prepared by conventional means from the corresponding free base compound by reacting, for example, the appropriate acid or base with the corresponding free base.

An "individual", "patient" or "subject", as that term is used herein, includes a member of any animal species including, but are not limited to, birds, humans and other primates, and other mammals including commercially relevant mammals such as cattle, pigs, horses, sheep, cats, and dogs. Preferably, the subject is a human.

The term "treat" or "treating", as used herein, means reducing the frequency with which symptoms are experienced by a subject or administering an agent or compound to reduce the frequency and/or severity with which symptoms are experienced. As used herein, "alleviate" is used interchangeably with the term "treat." Treating a disease, disorder or condition may or may not include complete eradication or elimination of the symptom. The term "therapeutic" as used herein means a treatment and/or prophylaxis. A therapeutic effect is obtained by suppression, remission, or eradication of the diseases disclosed herein.

As used herein, the term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating or preventing a disease in a subject.

"Instructional material," as that term is used herein, includes a publication, a recording, a diagram, or any other medium of expression which can be used to communicate the usefulness of the composition and/or compound of the invention in a kit. The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

AKR1C3 Inhibitors

There is a need in the art for novel treatments for androgen-dependent cancers, such as prostate cancer, including but not limited to castrate resistant prostate cancer (CRPC). AKR1C3 is overexpressed in a wide variety of cancers, including breast and prostate cancer, and is further up-regulated in CRPC. Multiple mechanisms contribute to the emergence of CRPC, but clinical trials with abiraterone acetate suggest that de novo synthesis of potent androgens within the prostate contribute to this disease stage. Indeed, the CRPC phenotype is characterized by elevated transcript levels for AKR1C3 and decreased transcript levels for 5α-reductase type 2, which results in an increased testosterone:5α-DHT ratio and indicates that testosterone (and not 5α-DHT) is the driver of CRPC.

AKR1C3 is therefore an attractive target for treating of androgen-dependent cancers, since inhibitors of this enzyme would block the penultimate step in androgen biosynthesis within the prostate. However, a clinically useful inhibitor of AKR1C3 should not inhibit the closely related isoforms AKR1C1 and AKR1C2, as they are involved in steroid hormone inactivation in target tissues.

AKR1C3 is inhibited by several structural classes of compounds. Structures of representative compounds from each known class of inhibitors and their potency towards AKR1C isoforms are shown in FIG. 4. Although there is significant structural diversity in the types of compounds that inhibit AKR1C3, they all contain one or more aromatic ring and at least one carbonyl group.

One class of compounds found to be AKR1C inhibitors are the NSAIDs and their analogues (Penning & Talalay, 1983, Proc. Natl. Acad. Sci. USA 80:4504-08; Byrns et al., 2008, Biochem. Pharmacol. 75:484-93; Bauman et al., 2005, Mol. Pharmacol. 67:60-68; Steckelbroeck et al., 2006, J. Pharmacol. Exp. Ther. 316:1300-09). In general, NSAIDs inhibit the AKR1C isoforms with potencies similar to those observed for the inhibition of their putative targets (PGHS). Given that NSAIDs have been extensively used in humans, their analogues are predicted to be well tolerated. Two classes of NSAIDs particularly stand out for their potential to lead to a selective inhibitor of AKR1C3 (Byrns et al., 2008, Biochem. Pharmacol. 75:484-93). Indomethacin exhibits a strong selectivity for AKR1C3 over AKR1C1 and AKR1C2, while the N-phenylanthranilic acids are the most potent NSAID inhibitors of AKR1C3.

Use of Crystal Structures in the Rational Design of Isoform-Specific Inhibitors of AKR1C3

Inspection of the available crystal structures of AKR1C3 bound to multiple ligands along with the crystal structures of the other AKR1C isoforms provides a structural basis for the rational design of isoform specific inhibitors of AKR1C3. To date, the available crystal structures and molecular docking studies of inhibitors using these structures have been mostly used to account for the observed activity of existing inhibitors. These structural studies have revealed features of AKR1C3 that can be exploited in the rational design of new selective inhibitors for this enzyme. However, the complexity of the ligand binding site of AKR1C3 deems the rational design of a new selective inhibitor of AKR1C3 a challenging task. Because of the existence of multiple sites and "induced-fit", it is not guaranteed that any given inhibitor would bind in the predicted mode.

As disclosed herein, the N-phenylanthranilates may be used as templates for rational AKR1C3 inhibitor design, based on the binding mode of flufenamic acid in AKR1C3. The binding properties of flufenamic acid in AKR1C3 suggest that A-ring substitution may be utilized to eliminate COX-inhibition and B-ring substitution may confer selectivity among AKR1C isoforms. Selectivity among AKRIC isoforms may be difficult to achieve. Based on the structural characteristics of the SP1 site of AKR1C3, B-ring substituents larger than the —$CF_3$ group of flufenamic acid and polar groups that would participate in hydrogen-bonding interaction with 5118 and/or Y319 of AKR1C3 may provide selectivity against other AKR1C isoforms.

Evaluation of Inhibitors

Compounds may be evaluated as selective reversible inhibitors of AKR1C3 by screening them against homogeneous recombinant AKR1C1-AKR1C4 expressed in *E. coli*. In each case, a discontinuous radiometric assay may be used to monitor the inhibition of progesterone reduction (20-ketosteroid reduction) catalyzed by AKR1C1, the inhibition of $\Delta^4$-AD reduction (17-ketosteroid reduction) catalyzed by AKR1C3, and the inhibition of 5α-DHT reduction (3-ketosteroid reduction) catalyzed by AKR1C2 and AKR1C4 (by measuring the formation of 20α-hydroxyprogesterone, testosterone or 3α-androstanediol by radiochromatography). $IC_{50}$ values are generated using steroid concentrations at $K_M$.

The most selective inhibitors may then be screened over a range of fixed substrate concentrations while varying the inhibitor concentration and the pattern of inhibition will be identified as competitive; non-competitive and uncompetitive using a global fit of the family of lines in GRAFIT (Byrns et al., 2008, Biochem. Pharmacol 75: 484-93). The most potent and selective inhibitors may be re-screened against recombinant COX-1 and COX-2 in assays in which the bis-dioxygenation of arachidonic acid is linked to the oxidation N',N',N', N'-tetramethyl-1,4-phenylenediamine, which is used as co-reductant in the peroxidase step (E=12,000 $M^{-1}cm^{-1}$ at 610 nm).

It should be noted that, as the volume of the SP1 site becomes completely occupied, tight-binding inhibition may be observed. In this instance, double-reciprocal plots of 1/v versus 1/[S] would be curvilinear at high substrate concentrations or display classical noncompetitive inhibition. Competitive tight-binding inhibition can be best diagnosed by plots of $IC_{50}$ values versus $[S]/K_M$, which should be linear and would fit to Equation 1, where $K_i$ is the dissociation constant for the tight binding inhibitor and $[E]_T$ is total enzyme. Selective AKR1C3 Inhibitors may be ultimately evaluated in the cell-based assays described elsewhere herein.

$$IC_{50}=K_i \cdot (1+[S]/K_M)+½[E]_T \qquad \text{(Equation 1)}$$

Compositions Useful within the Invention

In one aspect, the compositions useful within the methods of the invention comprise a compound of Formula (I):

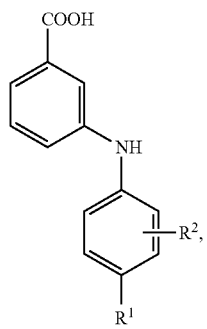

(I)

wherein:

$R^1$ is selected from the group consisting of $C_1$-$C_6$ alkyl, haloalkyl, halo, nitro, —CN, $C_1$-$C_6$ alkoxy, —C(C=O)H, —C(C=O)OH, —C(=O)—($C_1$-$C_6$ alkyl), and —$SO_3H$; and, each occurrence of $R^2$ is independently selected from the group consisting of H, $C_1$-$C_6$ alkyl, haloalkyl, halo, nitro, —CN, $C_1$-$C_6$ alkoxy, —C(C=O)H, —C(C=O)OH, —C(=O)—($C_1$-$C_6$ alkyl), and —$SO_3H$, or a salt thereof.

In one embodiment, $R^1$ is selected from the group consisting of $C_1$-$C_6$ alkyl, haloalkyl, halo, nitro, $C_1$-$C_6$ alkoxy, and —C(=O)—($C_1$-$C_6$ alkyl). In another embodiment, $R^1$ is selected from the group consisting of methyl, tert-butyl, methoxy, fluoro, chloro, bromo, trifluoromethyl, nitro and acetyl.

In one embodiment, each occurrence of $R^2$ is independently selected from the group consisting of H, $C_1$-$C_6$ alkyl, haloalkyl, halo, nitro, $C_1$-$C_6$ alkoxy, and —C(=O)—($C_1$-$C_6$ alkyl). In another embodiment, each occurrence of $R^2$ is independently is selected from the group consisting of H, methyl, tert-butyl, methoxy, fluoro, chloro, bromo, trifluoromethyl, nitro and acetyl.

In one embodiment, the compound of Formula (I) is selected from the group consisting of 3-[N-(4-nitrophenyl)amino]benzoic acid (Compound 5), 3-[N-(4-acetylphenyl)amino]benzoic acid (Compound 6), 3-[N-(4-trifluoromethylphenyl)amino]benzoic acid (Compound 7), 3-[N-(4-chlorophenyl)amino]benzoic acid (Compound 8), 3-[N-(4-bromophenyl)amino]benzoic acid (Compound 9), 3-[N-(4-tert-butylphenyl)amino]benzoic acid (Compound 10), 3-[N-(4-methoxyphenyl)amino]benzoic acid (Compound 11), 3-[N-(4-methylphenyl)amino]benzoic acid (Compound 12), mixtures thereof and salts thereof.

In one embodiment, the composition further comprises a pharmaceutically acceptable carrier.

In another aspect, the compositions useful within the methods of the invention comprise a compound of Formula (II) where the naphthyl ring can be alpha or beta substituted:

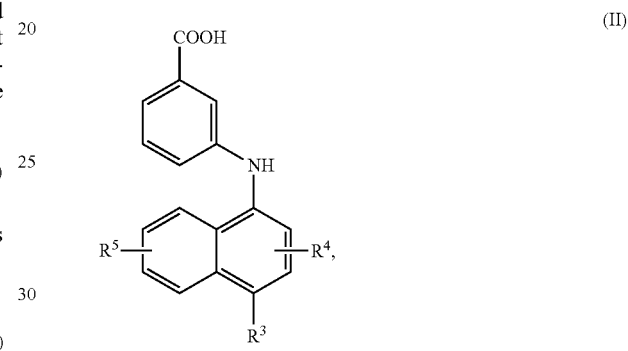

(II)

wherein:

$R^3$ is selected from the group consisting of $C_1$-$C_6$ alkyl, haloalkyl, halo, nitro, —CN, $C_1$-$C_6$ alkoxy, —C(C=O)H, —C(C=O)OH, —C(C=O)—($C_1$-$C_6$ alkyl), and —$SO_3H$; and, each occurrence of $R^4$ and $R^5$ is independently selected from the group consisting of H, $C_1$-$C_6$ alkyl, haloalkyl, halo, nitro, —CN, $C_1$-$C_6$ alkoxy, —C(C=O)H, —C(C=O)OH, —C(C=O)—($C_1$-$C_6$ alkyl), and —$SO_3H$, or a salt thereof.

In one embodiment, $R^3$ is selected from the group consisting of $C_1$-$C_6$ alkyl, haloalkyl, halo, nitro, $C_1$-$C_6$ alkoxy, and —C(C=O)—($C_1$-$C_6$ alkyl). In another embodiment, $R^3$ is selected from the group consisting of methyl, tert-butyl, methoxy, fluoro, chloro, bromo, trifluoromethyl, nitro and acetyl.

In one embodiment, each occurrence of $R^4$ is independently selected from the group consisting of H, $C_1$-$C_6$ alkyl, haloalkyl, halo, nitro, $C_1$-$C_6$ alkoxy, and —C(C=O)—($C_1$-$C_6$ alkyl). In another embodiment, each occurrence of $R^4$ is independently selected from the group consisting of H, methyl, tert-butyl, methoxy, fluoro, chloro, bromo, trifluoromethyl, nitro and acetyl.

In one embodiment, each occurrence of $R^5$ is independently selected from the group consisting of H, $C_1$-$C_6$ alkyl, haloalkyl, halo, nitro, $C_1$-$C_6$ alkoxy, and —C(C=O)—($C_1$-$C_6$ alkyl). In another embodiment, each occurrence of $R^5$ is independently selected from the group consisting of H, methyl, tert-butyl, methoxy, fluoro, chloro, bromo, trifluoromethyl, nitro and acetyl.

In one embodiment, the compound of Formula (II) is 3-((4-nitronaphthalen-1-yl)amino)benzoic acid (Compound 13), or a salt thereof:

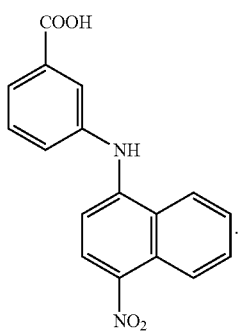 [SMILES: O=C(O)c1cccc(Nc2ccc([N+](=O)[O-])c3ccccc23)c1]

In one embodiment, the composition further comprises a pharmaceutically acceptable carrier.

Compounds useful within the methods of the invention may be synthesized using methodology described herein or any other techniques known in the art of organic synthesis, or may be obtained from commercial sources.

Salts

The compounds described herein may form salts with acids or bases, and such salts are included in the present invention. In one embodiment, the salts are pharmaceutically acceptable salts. The term "salts" embraces addition salts of free acids or free bases that are compounds of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. All of these salts may be prepared from the corresponding compound by reacting, for example, the appropriate acid or base Methods of the Invention The invention includes a method of treating, ameliorating or preventing cancer in a subject in need thereof. The method comprises administering to the subject a composition comprising a pharmaceutically acceptable carrier and a therapeutically effective amount of at least one compound selected from the group consisting of:

(i) a compound of Formula (I):

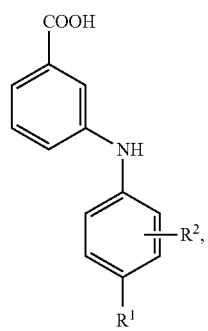

(I)

wherein:

$R^1$ is selected from the group consisting of $C_1$-$C_6$ alkyl, haloalkyl, halo, nitro, —CN, $C_1$-$C_6$ alkoxy, —C(C=O)H, —C(C=O)OH, —C(C=O)—($C_1$-$C_6$ alkyl), and —SO$_3$H; and, each occurrence of $R^2$ is independently selected from the group consisting of H, $C_1$-$C_6$ alkyl, haloalkyl, halo, nitro, —CN, $C_1$-$C_6$ alkoxy, —C(C=O)H, —C(C=O)OH, —C(C=O)—($C_1$-$C_6$ alkyl), and —SO$_3$H, (ii) a compound of Formula (II) where the naphthyl ring can be alpha or beta substituted:

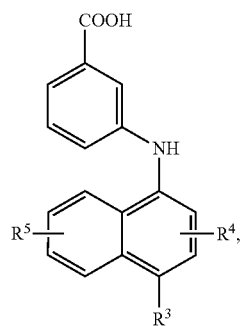

(II)

wherein:

$R^3$ is selected from the group consisting of $C_1$-$C_6$ alkyl, haloalkyl, halo, nitro, —CN, $C_1$-C6 alkoxy, —C(C=O)H, —C(C=O)OH, —C(C=O)—($C_1$-$C_6$ alkyl), and —SO$_3$H; and, each occurrence of $R^4$ and $R^5$ is independently selected from the group consisting of H, $C_1$-$C_6$ alkyl, haloalkyl, halo, nitro, —CN, $C_1$-$C_6$ alkoxy, —C(C=O)H, —C(C=O)OH, —C(C=O)—($C_1$-$C_6$ alkyl), and —SO$_3$H, mixtures thereof and salts thereof.

In one aspect, the cancer is androgen-dependent. In another aspect, the cancer is selected from the group consisting of prostate cancer, breast cancer, endometrial cancer, and acute myelogenous leukemia (AML). In yet another aspect, the prostate cancer comprises castrate resistant prostate cancer. In yet another embodiment, the subject is human.

In one embodiment, the compound of Formula (I) is selected from the group consisting of 3-[N-(4-nitrophenyl) amino]benzoic acid (Compound 5), 3-[N-(4-acetylphenyl) amino]benzoic acid (Compound 6), 3-[N-(4-trifluoromethylphenyl)amino]benzoic acid (Compound 7), 3-[N-(4-chlorophenyl)amino]benzoic acid (Compound 8), 3-[N-(4-bromophenyl)amino]benzoic acid (Compound 9), 3-[N-(4-tert-butylphenyl)amino]benzoic acid (Compound 10), 3-[N-(4-methoxyphenyl)amino]benzoic acid (Compound 11), 3-[N-(4-methylphenyl)amino]benzoic acid (Compound 12), mixtures thereof and salts thereof.

In one embodiment, the compound of Formula (II) is 3-((4-nitronaphthalen-1-yl)amino)benzoic acid (Compound 13), or a salt thereof.

In one embodiment, the cancer is prostate cancer and the method further comprises administering to the subject at least one therapeutic agent selected from the group consisting of indomethacin, desatinib, selegiline, seliciclib, TOK-001, SAHA, docetaxel, bevacizumab, taxotere, thalidomide, prednisone, Sipuleucel-T, cabazitaxel, MDV3100, ARN-509, abiraterone, temozolomide, mixtures thereof and salts thereof.

In one embodiment, the cancer is breast cancer and the method further comprises administering to the subject at least one therapeutic agent selected from the group consisting of tamoxifen, anastrozole, letrozole, vorozole, exemestane, fadrozole, formestane, raloxifene, mixtures thereof and salts thereof.

In one embodiment, the composition and the at least one therapeutic agent are administered concomitantly to the subject. In another embodiment, the composition and the at least one therapeutic agent are co-formulated.

The invention also includes a method of treating, ameliorating or preventing a condition or disease in a subject in need thereof, wherein the condition or disease is selected from the group consisting of diabetes, premature parturition, endometriosis, dysmenorrhea and benign prostate hyperplasia. The method comprises the step of administering to the subject a composition comprising a pharmaceutically acceptable carrier and a therapeutically effective amount of at least one compound selected from the group consisting of:
(i) a compound of Formula (I):

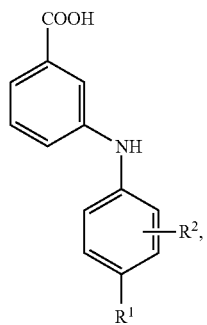

(I)

wherein:
$R^1$ is selected from the group consisting of $C_1$-$C_6$ alkyl, haloalkyl, halo, nitro, —CN, $C_1$-$C_6$ alkoxy, —C(C=O)H, —C(C=O)OH, —C(C=O)—($C_1$-$C_6$ alkyl), and —SO$_3$H; and,
each occurrence of $R^2$ is independently selected from the group consisting of H, $C_1$-$C_6$ alkyl, haloalkyl, halo, nitro, —CN, $C_1$-$C_6$ alkoxy, —C(C=O)H, —C(C=O)OH, —C(C=O)—($C_1$-$C_6$ alkyl), and —SO$_3$H, (ii) a compound of Formula (II) where the naphthyl ring can be alpha or beta substituted:

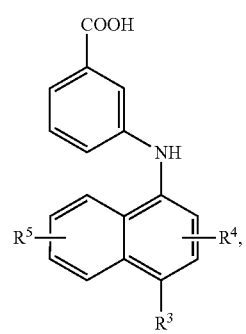

(II)

wherein:
$R^3$ is selected from the group consisting of $C_1$-$C_6$ alkyl, haloalkyl, halo, nitro, —CN, $C_1$-$C_6$ alkoxy, —C(C=O)H, —C(C=O)OH, —C(C=O)—($C_1$-$C_6$ alkyl), and —SO$_3$H; and,
each occurrence of $R^4$ and $R^5$ is independently selected from the group consisting of H, $C_1$-$C_6$ alkyl, haloalkyl, halo, nitro, —CN, $C_1$-$C_6$ alkoxy, —C(C=O)H, —C(C=O)OH, —C(C=O)—($C_1$-$C_6$ alkyl), and —SO$_3$H, mixtures thereof and salts thereof.

In one embodiment, the subject is human.

In one embodiment, the compound of Formula (I) is selected from the group consisting of 3-[N-(4-nitrophenyl) amino]benzoic acid (Compound 5), 3-[N-(4-acetylphenyl) amino]benzoic acid (Compound 6), 3-[N-(4-trifluoromethylphenyl)amino]benzoic acid (Compound 7), 3-[N-(4-chlorophenyl)amino]benzoic acid (Compound 8), 3-[N-(4-bromophenyl)amino]benzoic acid (Compound 9), 3-[N-(4-tert-butylphenyl)amino]benzoic acid (Compound 10), 3-[N-(4-methoxyphenyl)amino]benzoic acid (Compound 11), 3-[N-(4-methylphenyl)amino]benzoic acid (Compound 12), mixtures thereof and salts thereof.

In one embodiment, the compound of Formula (II) is 3-((4-nitronaphthalen-1-yl)amino)benzoic acid (Compound 13), or a salt thereof.

The invention further includes a method of treating, ameliorating or preventing a condition or disease which is dependent on a tissue-specific androgen effect. The method comprises the step of administering to the subject a composition comprising a pharmaceutically acceptable carrier and a therapeutically effective amount of at least one compound selected from the group consisting of:
(i) a compound of Formula (I):

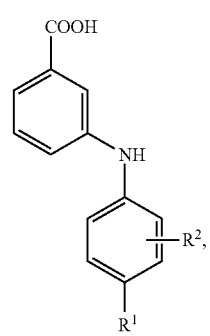

(I)

wherein:

$R^1$ is selected from the group consisting of $C_1$-$C_6$ alkyl, haloalkyl, halo, nitro, —CN, $C_1$-$C_6$ alkoxy, —C(C=O)H, —C(C=O)OH, —C(C=O)—($C_1$-$C_6$ alkyl), and —$SO_3$H; and, each occurrence of $R^2$ is independently selected from the group consisting of H, $C_1$-$C_6$ alkyl, haloalkyl, halo, nitro, —CN, $C_1$-$C_6$ alkoxy, —C(C=O)H, —C(C=O)OH, —C(C=O)—($C_1$-$C_6$ alkyl), and —$SO_3$H, (ii) a compound of Formula (II) where the naphthyl ring can be alpha or beta substituted:

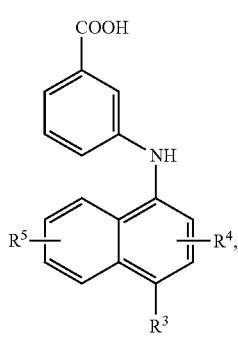

(II)

wherein:

$R^3$ is selected from the group consisting of $C_1$-$C_6$ alkyl, haloalkyl, halo, nitro, —CN, $C_1$-$C_6$ alkoxy, —C(C=O)H, —C(C=O)OH, —C(C=O)—($C_1$-$C_6$ alkyl), and —$SO_3$H; and, each occurrence of $R^4$ and $R^5$ is independently selected from the group consisting of H, $C_1$-$C_6$ alkyl, haloalkyl, halo, nitro, —CN, $C_1$-$C_6$ alkoxy, —C(C=O)H, —C(C=O)OH, —C(C=O)—($C_1$-$C_6$ alkyl), and —$SO_3$H, mixtures thereof and salts thereof.

In one embodiment, the compound useful within the method is a selective androgen receptor modulator (SARM). In another embodiment, the condition or disease is selected from the group consisting of alopecia, hirsutism, muscle wasting, cancer cachexia, aplastic anaemia, osteoporosis, male andropause, and combinations thereof. In yet another one embodiment, the subject is human.

In one embodiment, the compound of Formula (I) is selected from the group consisting of 3-[N-(4-nitrophenyl)amino]benzoic acid (Compound 5), 3-[N-(4-acetylphenyl)amino]benzoic acid (Compound 6), 3-[N-(4-trifluoromethylphenyl)amino]benzoic acid (Compound 7), 3-[N-(4-chlorophenyl)amino]benzoic acid (Compound 8), 3-[N-(4-bromophenyl)amino]benzoic acid (Compound 9), 3-[N-(4-tert-butylphenyl)amino]benzoic acid (Compound 10), 3-[N-(4-methoxyphenyl)amino]benzoic acid (Compound 11), 3-[N-(4-methylphenyl)amino]benzoic acid (Compound 12), mixtures thereof and salts thereof.

In one embodiment, the compound of Formula (II) is 3-((4-nitronaphthalen-1-yl)amino)benzoic acid (Compound 13), or a salt thereof.

The invention also includes a method of achieving a tissue-specific effect in a male subject in need thereof. The method comprises the step of administering to the subject a composition comprising a pharmaceutically acceptable carrier and a therapeutically effective amount of at least one compound selected from the group consisting of:

(i) a compound of Formula (I):

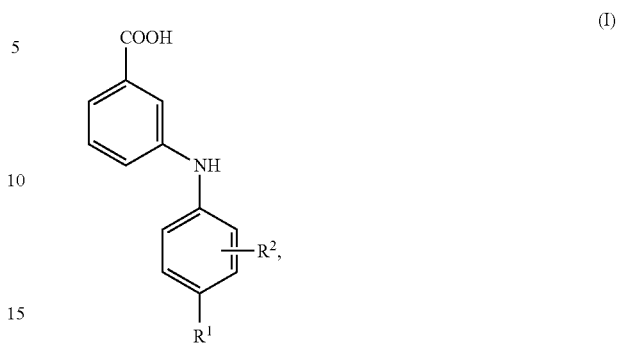

(I)

wherein:

$R^1$ is selected from the group consisting of $C_1$-$C_6$ alkyl, haloalkyl, halo, nitro, —CN, $C_1$-$C_6$ alkoxy, —C(C=O)H, —C(C=O)OH, —C(C=O)—($C_1$-$C_6$ alkyl), and —$SO_3$H; and, each occurrence of $R^2$ is independently selected from the group consisting of H, $C_1$-$C_6$ alkyl, haloalkyl, halo, nitro, —CN, $C_1$-$C_6$ alkoxy, —C(C=O)H, —C(C=O)OH, —C(C=O)—($C_1$-$C_6$ alkyl), and —$SO_3$H, (ii) a compound of Formula (II) where the naphthyl ring can be alpha or beta substituted:

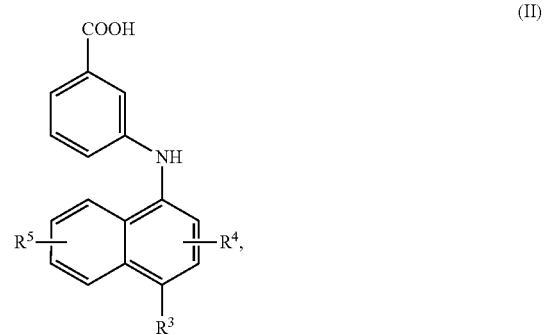

(II)

wherein:

$R^3$ is selected from the group consisting of $C_1$-$C_6$ alkyl, haloalkyl, halo, nitro, —CN, $C_1$-$C_6$ alkoxy, —C(C=O)H, —C(C=O)OH, —C(C=O)—($C_1$-$C_6$ alkyl), and —$SO_3$H; and, each occurrence of $R^4$ and $R^5$ is independently selected from the group consisting of H, $C_1$-$C_6$ alkyl, haloalkyl, halo, nitro, —CN, $C_1$-$C_6$ alkoxy, —C(C=O)H, —C(C=O)OH, —C(C=O)—($C_1$-$C_6$ alkyl), and —$SO_3$H, mixtures thereof and salts thereof.

In one embodiment, the tissue-specific androgen effect comprises an anabolic effect and erythropoiesis. In another embodiment, the compound useful within the method is a selective androgen receptor modulator. In yet another embodiment, the subject is human.

In one embodiment, the compound of Formula (I) is selected from the group consisting of 3-[N-(4-nitrophenyl)amino]benzoic acid (Compound 5), 3-[N-(4-acetylphenyl)amino]benzoic acid (Compound 6), 3-[N-(4-trifluoromethylphenyl)amino]benzoic acid (Compound 7), 3-[N-(4-chlorophenyl)amino]benzoic acid (Compound 8), 3-[N-(4-bromophenyl)amino]benzoic acid (Compound 9), 3-[N-(4- tert-butylphenyl)amino]benzoic acid (Compound 10), 3-[N-(4-methoxyphenyl)amino]benzoic acid (Compound 11), 3-[N-(4-methylphenyl)amino]benzoic acid (Compound 12), mixtures thereof and salts thereof.

In one embodiment, the compound of Formula (II) is 3-((4-nitronaphthalen-1-yl)amino)benzoic acid (Compound 13), or a salt thereof.

Combination Therapies

In one aspect, the compositions contemplated within the invention are useful in the methods of present invention in combination with one or more agents useful in the treatment of cancer, such as prostate cancer. These additional agents may comprise compositions of the present invention or agents (such as commercially available compounds) known to treat, prevent, or reduce cancer, such as prostate cancer. In one embodiment, the combination of a composition contemplated within the invention and a chemotherapeutic agent has additive, complementary or synergistic effects in the treatment of cancer, such as prostate cancer, in a subject, or prevention of cancer, such as prostate cancer, in a subject. In another embodiment, the combination of a compound contemplated within the invention and an agent used to treat cancer, such as prostate cancer, has additive, complementary or synergistic effects in the treatment of cancer, such as prostate cancer, in a subject, or prevention of cancer, such as prostate cancer, in a subject.

In one embodiment, the therapeutic agents that may be used to treat prostate cancer include:
indomethacin (2-{1-[(4-chlorophenyl)carbonyl]-5-methoxy-2-methyl-1H-indol-3-yl}acetic acid),
desatinib (N-(2-chloro-6-methylphenyl)-2-[[6-[4-(2-hydroxyethyl)-1-piperazinyl]-2-methyl-4-pyrimidinyl]amino]-5-thiazole carboxamide monohydrate),
selegiline ((R)—N-methyl-N-(1-phenylpropan-2-yl)prop-2-yn-1-amine),
seliciclib (2-(R)-(1-Ethyl-2-hydroxyethylamino)-6-benzylamino-9-isopropylpurine),
TOK-001 (VN/124-1; (3β)-17-(1H-benzimidazol-1-yl)androsta-5,16-dien-3-ol),
SAHA ($N^1$-hydroxy-$N^8$-phenyl-octanediamide),
docetaxel (1,7β,10β-trihydroxy-9-oxo-5β,20-epoxytax-11-ene-2α,4,13α-triyl 4-acetate 2-benzoate 13-{(2R,3S)-3-[(tert-butoxycarbonyl)amino]-2-hydroxy-3-phenylpropanoate}),
bevacizumab (Avastin),
taxotere (1,7β,10β-trihydroxy-9-oxo-5β,20-epoxytax-11-ene-2α,4,13α-triyl 4-acetate 2-benzoate 13-{(2R,3S)-3-[(tert-butoxycarbonyl)amino]-2-hydroxy-3-phenylpropanoate}),
thalidomide ((RS)-2-(2,6-dioxopiperidin-3-yl)-1H-isoindole-1,3(2H)-dione),
prednisone ((8S,9S,10R,13S,14S,17R)-17-hydroxy-17-(2-hydroxyacetyl)-10,13-dimethyl-7,8,9,10,12,13,14,15,16,17-decahydro-3H-cyclopenta[a]phenanthrene-3,11(6H)-dione),
Provenge (Sipuleucel-T or APC8015),
cabazitaxel ((1S,2S,3R,4S,7R,9S,10S,12R,15S)-4-(Acetyloxy)-15-{[(2R,3S)-3-{[(tert-butoxy)carbonyl]amino}-2-hydroxy-3-phenylpropanoyl]oxy}-1-hydroxy-9,12-dimethoxy-10,14,17,17-tetramethyl-11-oxo-6-oxatetracyclo[11.3.1.0$^{3,10}$.0$^{4,7}$]heptadec-13-ene-2-yl),
MDV3100 (4-(3-(4-cyano-3-(trifluoromethyl)phenyl)-5,5-dimethyl-4-oxo-2-thioxoimidazolidin-1-yl)-2-fluoro-N-methylbenzamide),
ARN-509 (4-(7-(6-cyano-5-(trifluoromethyl)pyridin-3-yl)-8-oxo-6-thioxo-5,7-diazaspiro[3.4]octan-5-yl)-2-fluoro-N-methylbenzamide),
abiraterone ((3S,8R,9S,10R,13S,14S)-10,13-dimethyl-17-(pyridin-3-yl)-2,3,4,7,8,9,10,11,12,13,14,15-dodecahydro-1H-cyclopenta[a]phenanthren-3-ol), and
temozolomide (TMZ; 4-methyl-5-oxo-2,3,4,6,8-pentazabicyclo-[4.3.0]-nona-2,7,9-triene-9-carboxamide).

In another aspect, the compositions contemplated within the invention are useful in the methods of present invention in combination with one or more agents useful in the treatment of cancer, such as breast cancer. These additional agents may comprise compositions of the present invention or agents (such as commercially available compounds) known to treat, prevent, or reduce cancer, such as breast cancer. In one embodiment, the combination of a composition contemplated within the invention and a chemotherapeutic agent has additive, complementary or synergistic effects in the treatment of cancer, such as breast cancer, in a subject, or prevention of cancer, such as breast cancer, in a subject.

In one embodiment, the therapeutic agents that may be used to treat breast cancer include:
Tamoxifen: (Z)-2-[4-(1,2-diphenylbut-1-enyl)phenoxy]-N,N-dimethylethanamine;
Anastrozole: 2-[3-(1-cyano-1-methyl-ethyl)-5-(1H-1,2,4-triazol-1-ylmethyl)phenyl]-2-methyl-propanenitrile;
Letrozole: 4-[(4-cyanophenyl)-(1,2,4-triazol-1-yl)methyl]benzonitrile;
Vorozole: 6-[(4-chlorophenyl)-(1,2,4-triazol-1-yl)methyl]-1-methyl-benzotriazole;
Exemestane: 10,13-dimethyl-6-methylidene-7,8,9,10,11,12,13,14,15,16-decahydrocyclopenta[a]phenanthrene-3,17-dione;
Fadrozole: 4-(5,6,7,8-tetrahydroimidazo[1,5-c]pyridin-5-yl)benzonitrile;
Formestane: (8R,9S,10R,13S,14S)-4-hydroxy-10,13-dimethyl-2,6,7,8,9,11,12,14,15,16-decahydro-1H-cyclopenta[a]phenanthrene-3,17-dione; and,
Raloxifene: [6-hydroxy-2-(4-hydroxyphenyl)-benzothiophen-3-yl]-[4-[2-(1-piperidyl)ethoxy]phenyl]-methanone.

In yet another aspect, the compositions contemplated within the invention are useful in the methods of present invention in combination with one or more agents useful in the treatment of a condition or disease selected from the group consisting of endometrial cancer and AML.

In yet another aspect, the compositions contemplated within the invention are useful in the methods of present invention in combination with one or more agents useful in the treatment of a condition or disease selected from the group consisting of diabetes, premature parturition, endometriosis, dysmenorrhea, benign prostate hyperplasia, alopecia, hirsutism, muscle wasting, cancer cachexia, aplastic anaemia, osteoporosis, male andropause, and combinations thereof.

In one embodiment, the compositions useful within the invention and the therapeutic agents are administered concomitantly to said subject. The term "concomitantly" indicates that the compositions useful within the invention and the agents are administered to the subject at the same time or within a limited interval of time (such as 4 hours, 2 hours, 1 hour, 30 minutes, 15 minutes, 5 minutes or 1 minute, or any fraction thereof) of each other. In another embodiment, the compositions useful within the invention and the therapeutic agents are co-formulated.

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Pharmaceutical Compositions and Therapies

Administration of a composition useful within the invention may be achieved in a number of different ways, using methods known in the art. The therapeutic and prophylactic methods of the invention thus encompass the use of pharmaceutical compositions comprising the compounds useful within the invention to practice the methods of the invention. The pharmaceutical compositions useful for practicing the invention may be administered to deliver a dose of 1 ng/kg/day to 100 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Although the description of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Typically, dosages that may be administered in a method of the invention to an animal, preferably a human, range in amount from 0.5 µg to about 50 mg per kilogram of body weight of the animal. While the precise dosage administered will vary depending upon any number of factors, including but not limited to, the type of animal and type of disease state being treated, the age of the animal and the route of administration, the dosage of the compound will preferably vary from about 1 µg to about 10 mg per kilogram of body weight of the animal. More preferably, the dosage will vary from about 3 µg to about 1 mg per kilogram of body weight of the animal.

Pharmaceutical compositions that are useful in the methods of the invention may be prepared, packaged, or sold in formulations suitable for oral, parenteral, topical, buccal, or another route of administration. Other contemplated formulations include projected nanoparticles, liposomal preparations, resealed erythrocytes containing the active ingredient, and immunologically-based formulations.

The formulations of the pharmaceutical compositions described herein may be prepared by any method known or hereafter developed in the art of pharmacology. In general, such preparatory methods include the step of bringing the active ingredient into association with a pharmaceutically acceptable carrier or one or more other accessory ingredients, and then, if necessary or desirable, shaping or packaging the product into a desired single- or multi-dose unit.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage.

In one embodiment, the compositions of the invention are formulated using one or more pharmaceutically acceptable excipients or carriers. In one embodiment, the pharmaceutical compositions of the invention comprise a therapeutically effective amount of a compound or conjugate of the invention and a pharmaceutically acceptable carrier. Pharmaceutically acceptable carriers that are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin. In one embodiment, the pharmaceutically acceptable carrier is not DMSO alone.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an anti-oxidant and a chelating agent that inhibits the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Controlled- or sustained-release formulations of a composition of the invention may be made using conventional technology, in addition to the disclosure set forth elsewhere herein. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the compositions of the invention.

Controlled-release of an active ingredient can be stimulated by various inducers, for example pH, temperature, enzymes, water, or other physiological conditions or compounds. The term "controlled-release component" in the context of the present invention is defined herein as a compound or compounds, including, but not limited to, polymers, polymer matrices, gels, permeable membranes, liposomes, nanoparticles, or microspheres or a combination thereof that facilitates the controlled-release of the active ingredient.
Administration/Dosing The regimen of administration may affect what constitutes an effective amount. The therapeutic formulations may be administered to the subject either prior to or after a diagnosis of disease. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a subject, preferably a mammal, more preferably a human, may be carried out using known procedures, at dosages and for periods of time effective to prevent or treat disease. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the subject being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

The composition may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Actual dosage levels of the active ingredients in the pharmaceutical compositions of this invention may be varied so as to obtain an amount of the active ingredient that is effective to achieve the desired therapeutic response for a particular subject, composition, and mode of administration, without being toxic to the subject.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease in a subject.

In one embodiment, the compositions of the invention are administered to the subject in dosages that range from one to five times per day or more. In another embodiment, the compositions of the invention are administered to the subject in range of dosages that include, but are not limited to, once every day, every two, days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any subject will be determined by the attending physical taking all other factors about the subject into account.

Compounds of the invention for administration may be in the range of from about 0.1 mg to about 1,000 mg, about 0.2 mg to about 950 mg, about 0.4 mg to about 900 mg, about 1 mg to about 850 mg, about 5 mg to about 750 mg, about 20 mg to about 700 mg, about 30 mg to about 600 mg, about 50 mg to about 500 mg, about 75 mg to about 400 mg, about 100 mg to about 300 mg, about 120 mg to about 250 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating the same or another disease as that treated by the compositions of the invention) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a composition of the invention, alone or in combination with a second pharmaceutical agent; and instructions for using the composition to treat, prevent, or reduce one or more symptoms of a disease in a subject.

Routes of Administration

Routes of administration of any of the compositions of the invention include oral, nasal, rectal, parenteral, sublingual, transdermal, transmucosal (e.g., sublingual, lingual, (trans) buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

For oral administration, the compositions of the invention may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400).

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl para-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium.

The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds of the invention, and a further layer providing for the immediate release of a medication for treatment of a disease. Using a wax/pH-sensitive polymer mix, a gastric insoluble composition may be obtained in which the active ingredient is entrapped, ensuring its delayed release.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraocular, intravitreal, subcutaneous, intraperitoneal, intramuscular, intrasternal injection, intratumoral, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations that are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Topical Administration

A pharmaceutical composition of the invention may be prepared, packaged, or sold in a formulation suitable for topical administration. There are several advantages to delivering compounds, including drugs or other therapeutic agents, into the skin (dermal drug delivery) or into the body through the skin (transdermal drug delivery). Transdermal compound delivery offers an attractive alternative to injections and oral medications. Dermal compound delivery offers an efficient way to deliver a compound to the skin of a mammal, and preferably a human, and provides a method of treatment of the skin, or otherwise provides a method of affecting the skin, without the need to break or damage the outer layer of the skin. In the present invention, dermal delivery, by way of a dermally-acting compound of the invention, provides these advantages for treatment of a skin-related condition, disorder or disease.

A number of compounds, including some drugs, will penetrate the skin effectively simply because the molecules are relatively small and potent at small doses of 0.1 mg to 15 mg/day (Kanikkannan et al., 2000, Curr. Med. Chem. 7:593-608). Many other compounds and drugs can be delivered only when an additional enhancement system is provided to "force" them to pass through the skin. Among several methods of transdermal drug delivery are electroporation, sonophoresis, iontophoresis, permeation enhancers (cyclodextrins), and liposomes. While the aforementioned methods are also included in the present invention for dermal delivery of the compounds of the invention, liposomes represent a preferred dermal delivery method.

The composition of the invention may consist of the active ingredient alone, in a form suitable for administration to a subject, or the composition may comprise at least one active ingredient and one or more pharmaceutically acceptable carriers, one or more additional ingredients, or some combination of these. The active ingredient may be present in the composition in the form of a physiologically acceptable ester or salt, such as in combination with a physiologically acceptable cation or anion, as is well known in the art. Compositions of the invention will also be understood to encompass pharmaceutical compositions useful for treatment of other conditions, disorders and diseases associated with the skin.

In one aspect, a dermal delivery vehicle of the invention is a composition comprising at least one first compound that can facilitate dermal delivery of at least one second compound associated with, or in close physical proximity to, the composition comprising the first compound. As will be understood by the skilled artisan, when armed with the disclosure set forth herein, such delivery vehicles include, but should not be limited to, liposomes, nanosomes, phospholipid-based non-liposome compositions (eg., selected cochleates), among others.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 0.001% to about 90% (w/w) active ingredient, although the concentration of the active ingredient may be as high as the solubility limit of the active ingredient in the solvent. Formulations for topical administration may further comprise one or more of the additional ingredients described herein.

In one aspect of the invention, a dermal delivery system includes a liposome delivery system, and that the present invention should not be construed to be limited to any particular liposome delivery system. Based on the disclosure set forth herein, the skilled artisan will understand how to identify a liposome delivery system as being useful in the present invention.

The present invention also encompasses the improvement of dermal and transdermal drug delivery through the use of penetration enhancers (also called sorption promoters or accelerants), which penetrate into skin to reversibly decrease the barrier resistance. Many compounds are known in the art for penetration enhancing activity, including sulphoxides (such as dimethylsulphoxide, DMSO), azones (e.g. laurocapram), pyrrolidones (for example 2-pyrrolidone, 2P), alcohols and alkanols (ethanol, or decanol), glycols (for example propylene glycol, PG, a common excipient in topically applied dosage forms), surfactants (also common in dosage forms) and terpenes. Other enhancers include oleic acid, oleyl alcohol, ethoxydiglycol, laurocapram, alkanecarboxylic acids, dimethylsulfoxide, polar lipids, or N-methyl-2-pyrrolidone.

In alternative embodiments, the topically active pharmaceutical or cosmetic composition may be optionally combined with other ingredients such as moisturizers, cosmetic adjuvants, anti-oxidants, chelating agents, surfactants, foaming agents, conditioners, humectants, wetting agents, emulsifying agents, fragrances, viscosifiers, buffering agents, preservatives, sunscreens and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art.

In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art. The compositions of this invention may also contain active amounts of retinoids (i.e., compounds that bind to any members of the family of retinoid receptors), including, for example, tretinoin, retinol, esters of tretinoin and/or retinol and the like.

The composition of the invention may comprise a preservative from about 0.005% to 2.0% by total weight of the composition. The preservative is used to prevent spoilage in the case of an aqueous gel because of repeated patient use when it is exposed to contaminants in the environment from, for example, exposure to air or the patient's skin, including contact with the fingers used for applying a composition of the invention such as a therapeutic gel or cream. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an antioxidant and a chelating agent which inhibit the degradation of the compound for use in the invention in the aqueous gel formulation. Preferred antioxidants for some compounds are BHT, BHA, alpha-tocopherol and ascorbic acid in the preferred range of about 0.01% to 5% and BHT in the range of 0.01% to 1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Additional components may include, but should not be limited to those including water, oil (eg., olive oil/PEG7), biovera oil, wax (eg., jojoba wax), squalene, myristate (eg., isopropyl myristate), triglycerides (eg., caprylic triglyceride), Solulan 98, cocoa butter, shea butter, alcohol (eg., behenyl alcohol), stearate (eg., glycerol-monostearate), chelating agents (eg., EDTA), propylene glycol, SEPIGEL (Seppic, Inc., Fairfield, N.J.), silicone and silicone derivatives (eg., dimethicone, cyclomethicone), vitamins (eg., vitamin E), among others.

Buccal Administration

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

Rectal Administration

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier.

As is well known in the art, enema preparations may be administered using, and may be packaged within, a delivery device adapted to the rectal anatomy of the subject. Enema preparations may further comprise various additional ingredients including, but not limited to, antioxidants, and preservatives.

Additional Administration Forms

Additional dosage forms of this invention include dosage forms as described in U.S. Pat. Nos. 6,340,475; 6,488,962; 6,451,808; 5,972,389; 5,582,837 and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

Controlled- or sustained-release formulations of a pharmaceutical composition of the invention may be made using conventional technology, using for example proteins equipped with pH sensitive domains or protease-cleavable fragments. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, micro-particles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gel-caps, and caplets, which are adapted for controlled-release are encompassed by the present invention.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased subject compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilitates the controlled-release of the active ingredient.

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form.

For sustained release, the compounds may be formulated with a suitable polymer or hydrophobic material that provides sustained release properties to the compounds. As such, the compounds for use the method of the invention may be administered in the form of microparticles, for example, by injection or in the form of wafers or discs by implantation.

In a preferred embodiment of the invention, the compounds of the invention are administered to a subject, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Kits of the Invention

The invention also includes a kit comprising a compound useful within the methods of the invention and an instructional material that describes, for instance, administering the compound to a subject as a prophylactic or therapeutic treatment for cancer, for example prostate cancer, as described elsewhere herein. In an embodiment, the kit further comprises a (preferably sterile) pharmaceutically acceptable carrier suitable for dissolving or suspending the therapeutic composition, comprising the compound useful within the methods of the invention, for instance, prior to administering the molecule to a subject. Optionally, the kit comprises an applicator for administering the compound.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

The materials and methods employed in the experiments and the results of the experiments presented in this Example are now described.

General Methods:

Solvents used for extraction and purification were HPLC grade from Fisher. Unless otherwise indicated, all reactions were run under an inert atmosphere of argon. Anhydrous toluene was obtained via distillation from the appropriate drying agents. Commercial reagents were used as received. Deuterated solvents were obtained from Cambridge Isotope labs.

Merck pre-coated silica gel plates (250 µm, 60 F254) were used for analytical TLC. Spots were visualized using 254 nm ultraviolet light, with either anisaldehyde or potassium permanganate stains as visualizing agents. Chromatographic purifications were performed on Sorbent Technologies silica gel (particle size 32-63 microns).

$^1$H and $^{13}$C NMR spectra were recorded at 500 MHz, 360 MHz and 125 MHz, 90 MHz respectively, in $CDCl_3$ or $(CD_3)_2SO$ on a Bruker AM-500, DRX-500, or DRX-360 spectrometer. Chemical shifts are reported relative to the internal standards chloroform ($\delta$ 7.27 for $^1$H, $\delta$ 77.23 for $^{13}$C) or dimethyl sulfoxide (($\delta$ 2.50 for $^1$H, $\delta$ 39.53 for $^{13}$C).

High resolution mass spectra were obtained at the University of Pennsylvania Mass Spectrometry Service Center on an Autospec high resolution double-focusing electrospray ionization/chemical ionization spectrometer with either DEC 11/73 or OPUS software data system. All compounds were >94-95% pure as judged by RP-HPLC coupled to UV detection.

Molecular Probes for AKR1C3: Real-Time RT-PCR and Monoclonal Ab Development

Because AKR1C3 shares high sequence identity (>86%) with AKR1C1-AKR1C4, selective reagents are needed to detect only this specific isoform at the mRNA, protein, and functional level. An isoform specific real-time PCR protocol was developed for the detection of each AKR1C isoform and a high-titer isoform specific monoclonal antibody (mAb) was developed for AKR1C3.

Figure 11:
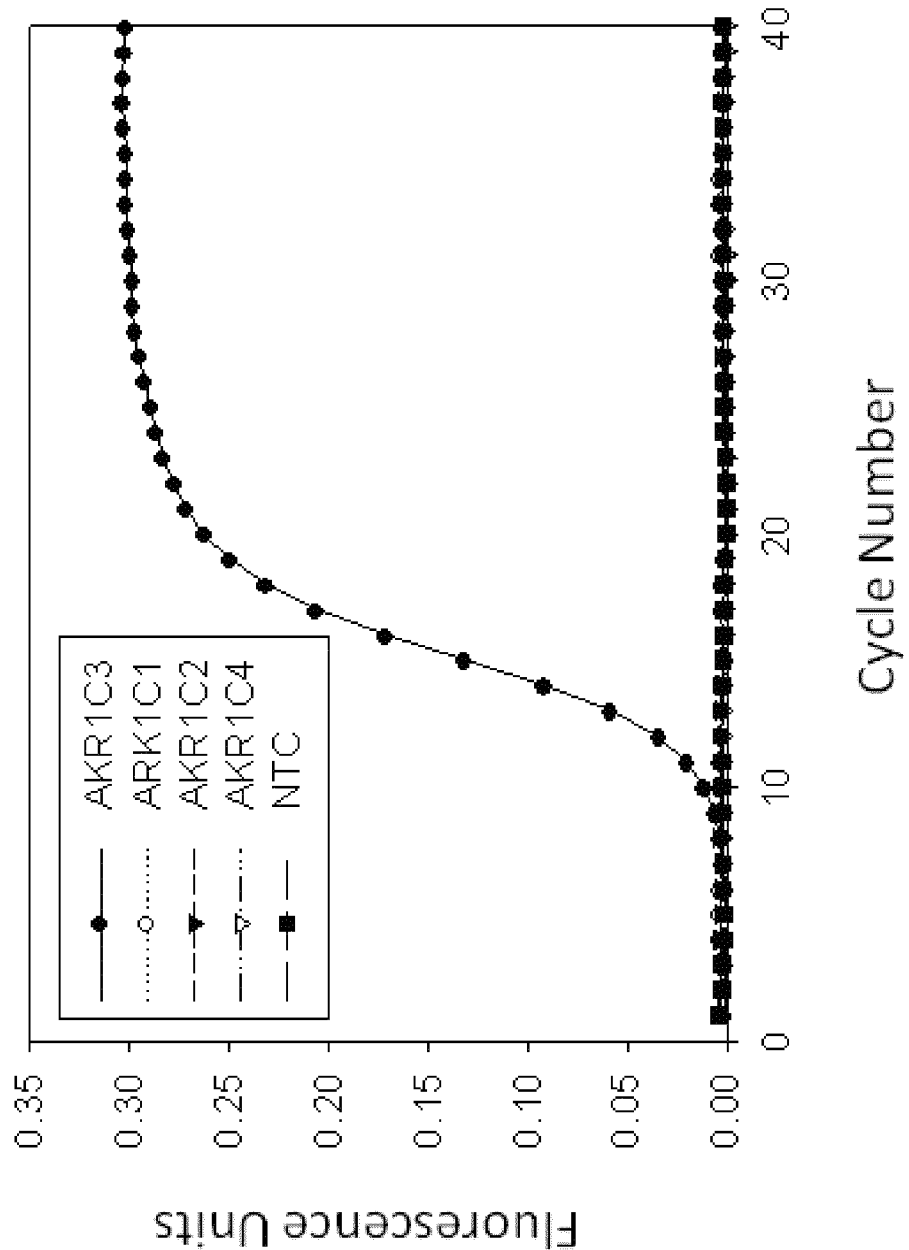
FIG. 11 is a graph illustrating the isoform specific real-time RT-PCR for AKR1C3. Only AKR1C3 forward and reverse primers amplified an AKR1C3 template (25 pg). The primers failed to amplify 25 pg of a AKR1C1, 1C2 and 1C4 template or a nontemplate control (NTC).

Real-Time RT-PCR Protocol for AKR1C3:

Specific oligonucleotide primer pairs for AKR1C1-AKR1C4 were designed that bind to relatively diverse regions of sequences located in exon 2 and exon 3. Primer pairs for high-abundance and low abundance house-keeping genes GAPDH and PBGD (porphobilinogen deaminase) were also developed. Real-time PCR reactions were carried out with the DNA Engine 2 Opticon™ (MJ Research, Inc., Waltham, Mass., USA) using the non-specific DNA binding dye SYBR green I for detection of the PCR products. To control for AKR1C isoform-specificity, possible false amplification of the other three isoforms were checked for. For this purpose, 25 pg of the target cDNA standard, as well as 25 pg of the other three cDNA standards were subjected to each real-time PCR assay. All four real time PCR methods were highly isoform-specific, since none of the assays significantly amplified the high amounts of the non-target cDNA standards (FIG. 11). Overall-specificity of the assays was checked by amplification of AKR1C1-1C4 in a total cDNA mixture. The subsequent fractionation on 2% agarose gels revealed exclusive amplification of PCR products of the predicted size. Non-specific PCR products such as primer-dimer amplicons were not observed and sequence analyses verified the exclusive amplification of the target cDNA. Finally, the protocols were checked by generating $C_t$-value standard curves and measuring the $r^2$-values. The threshold cycle (CO is the cycle at which the fluorescence signal is significantly above background. For accurate quantitation, a standard dilution series (2,500,000 to 0.025 fg) was employed in each assay. All four protocols produced linear standard curves over the dynamic range ($10^9$) and gave $r^2$-values of >0.995. Quantitation of target mRNA expression levels in total RNA samples is based on the measurement of threshold cycles (CO. Comparison of the $C_t$-values of target mRNA species in the total RNA samples with the respective standard curve enabled the quantification of expression levels in fg of full-length target gene mRNA per ng of total RNA [$fg_{target}$ mRNA/$ng_{total}$ RNA]. Transcript levels are normalized to the mean value of GAPDH or PBDG seen in replicate samples.

Figure 12:
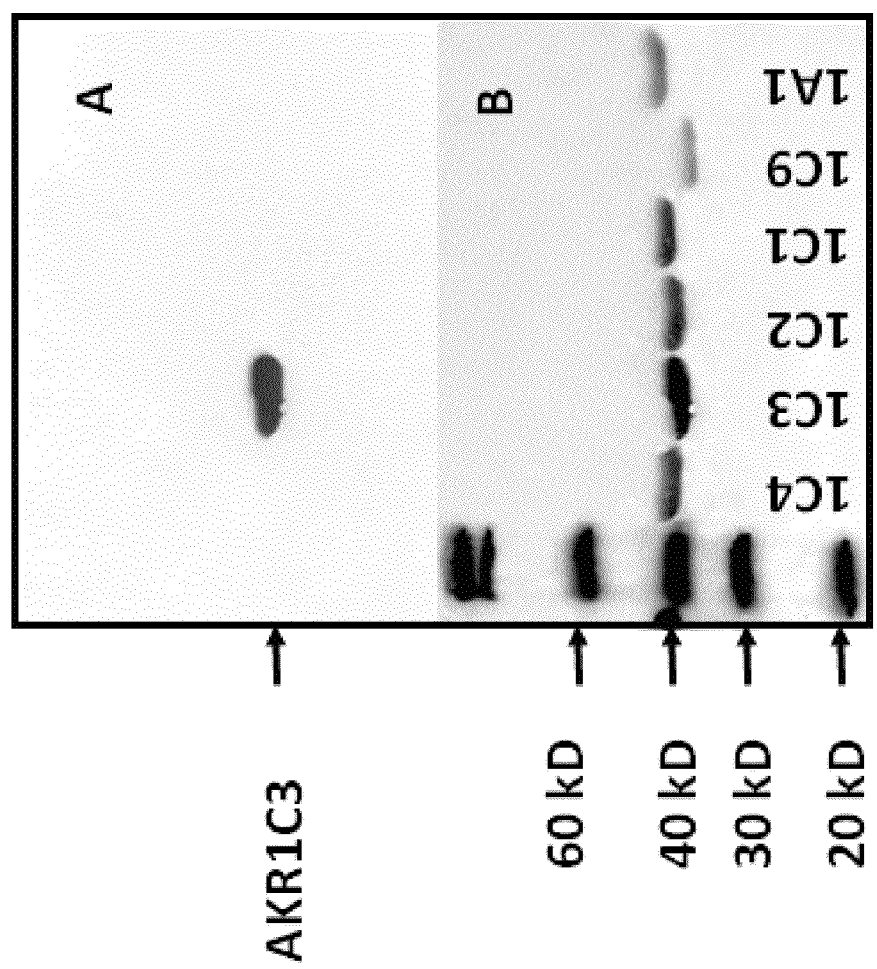
FIG. 12, comprising
Figure 13:
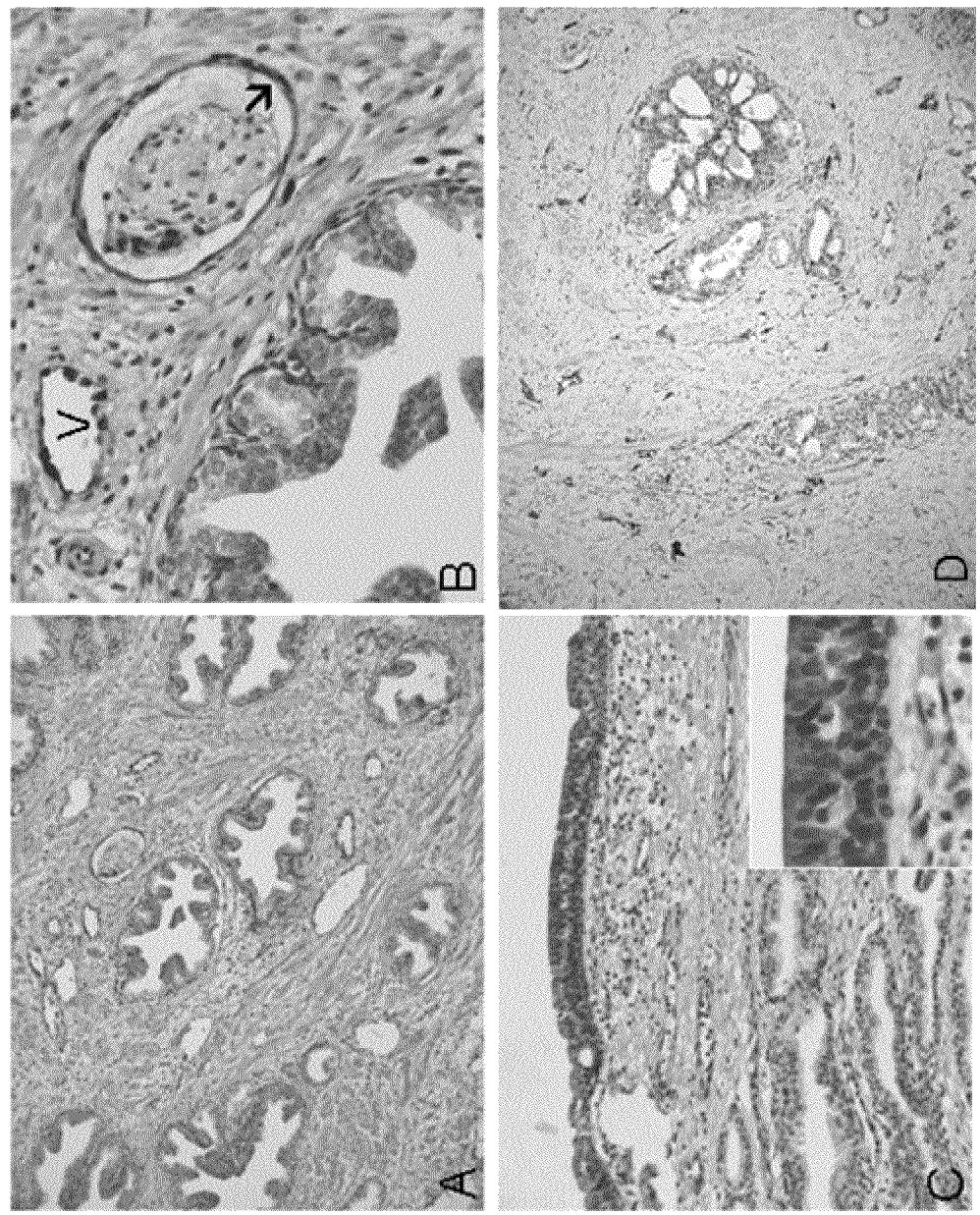
FIG. 13 illustrates the immunohistochemical (IHC) staining of AKR1C3 in prostate. IHC positive staining was observed in stromal cells (A), endothelial cells (B), prostatic urothelial (transitional) epithelium (C), and adenocarcinoma (D).

Development of Monoclonal Ab for AKR1C3:

Using hybridoma technology, a high-titer murine anti-human AKR1C3-IgG suitable for immunoblot analysis and IHC was developed. Mice were immunized with 200 µg homogeneous recombinant AKR1C3. Spleen cells from the immunized animals were harvested, fused, and clonal cells isolated. Culture media from a total of 2000 hybridomas were screened via ELISA on 96-well titer plates containing immobilized AKR1C1-AKR1C4 using HRP-conjugated goat anti-murine IgG using HRP and 2,2-azinodi-[3-ethylbenzothiazoline sulfonate] as chromogenic agent. This produced a monoclonal antibody that was specific for AKR1C3 (clone NP6.G6). The AKR1C3 mAb does not cross-react with human AKR1C1, AKR1C2 or AKR1C4, or AKR1A1 or rat 3α-HSD (AKR1C9) on immunoblot analysis (FIG. 12). The AKR1C3 mAb can be used to detect AKR1C3 expression by IHC in sections of paraffin-embedded prostate and mammary gland. In the normal prostate, enzyme staining was limited to stromal and endothelial cells with only faint staining in the epithelial cells. In adenocarcinoma of the prostate elevated staining was observed in carcinoma cells and endothelial cells (FIG. 13). In a pilot study positive immunoreactivity in 9/11 adenocarcinoma specimens that also stained positive for the AR were also observed. But no correlation was noted between levels of AKR1C3 and AR expression. In the breast, enzyme staining was detected in ductal carcinoma in situ (DCIS) where the cancerous cells were strongly immunoreactive. The immunoreactivity was ablated by pre-incubation of the primary Ab with recombinant AKR1C3. Thus the reagent has utility to assess the localized expression of AKR1C3 in hormonal-dependent malignancies of the prostate and breast. The mAb also detected AKR1C3 expression in prostate cancer cells that were hormone refractory.

Determination of Inhibitory Potency

The inhibitory potency of the compounds disclosed herein was determined using purified homogenous recombinant enzymes. Full concentration response studies were conducted and $IC_{50}$ values calculated using Grafit 5.0 software. The compounds were evaluated for their effects on enzyme catalyzed oxidation of S-tetralol using a 96-well plate format. This assay measures the inhibition of the NADP+ dependent oxidation of S-tetralol by monitoring the increase in fluorescence of NADPH. S-Tetralol is a universal substrate for the AKR1C isoforms and this assay has a lower background rate and provides a more stable signal than an assay that monitors the NADPH reduction of phenanthrene-9,10-dione. It is also preferred over the discontinuous radiometric assays since it does not use radioisotopes and is less time-consuming.

The reaction was fluorimetrically (exc/em; 340 nm/460 nm) monitored by the measurement of NADPH production on a BIOTEK Synergy 2 Multimode plate reader at 37° C. Assay mixture consists of S-tetralol (in DMSO), inhibitor (in DMSO), 100 mM phosphate buffer, pH 7.0, 200 µM NADP+, and purified recombinant enzyme to give a total volume of 200 µl and 4% DMSO. The S-tetralol concentration used for AKR1C2 and AKR1C3 inhibition assay were 22.5 µM and 165 µM, respectively, equal to the $K_M$ obtained for the respective isoforms under the same experimental conditions. Initial velocities, obtained by linear regression of the progress curve in the presence of varying concentrations of inhibitor, were compared to the solvent control to give percent inhibition values. $IC_{50}$ values were obtained from a single experiment with each concentration run in quadruplicate.

Figure 14:
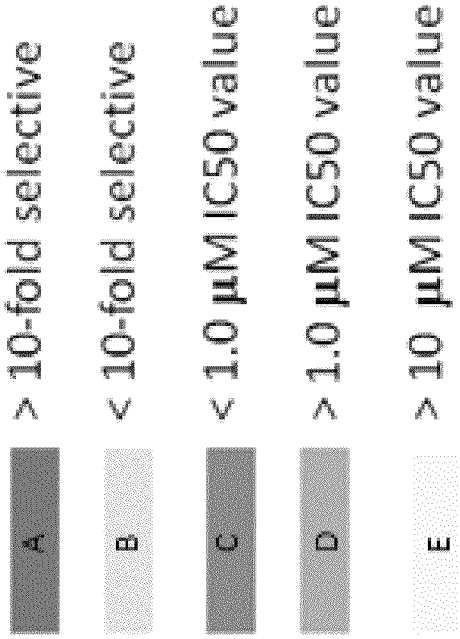
FIG. 14 illustrates a portion of the heat-map of high-throughput screening of AKR1C3 inhibitors.
Figure 15:
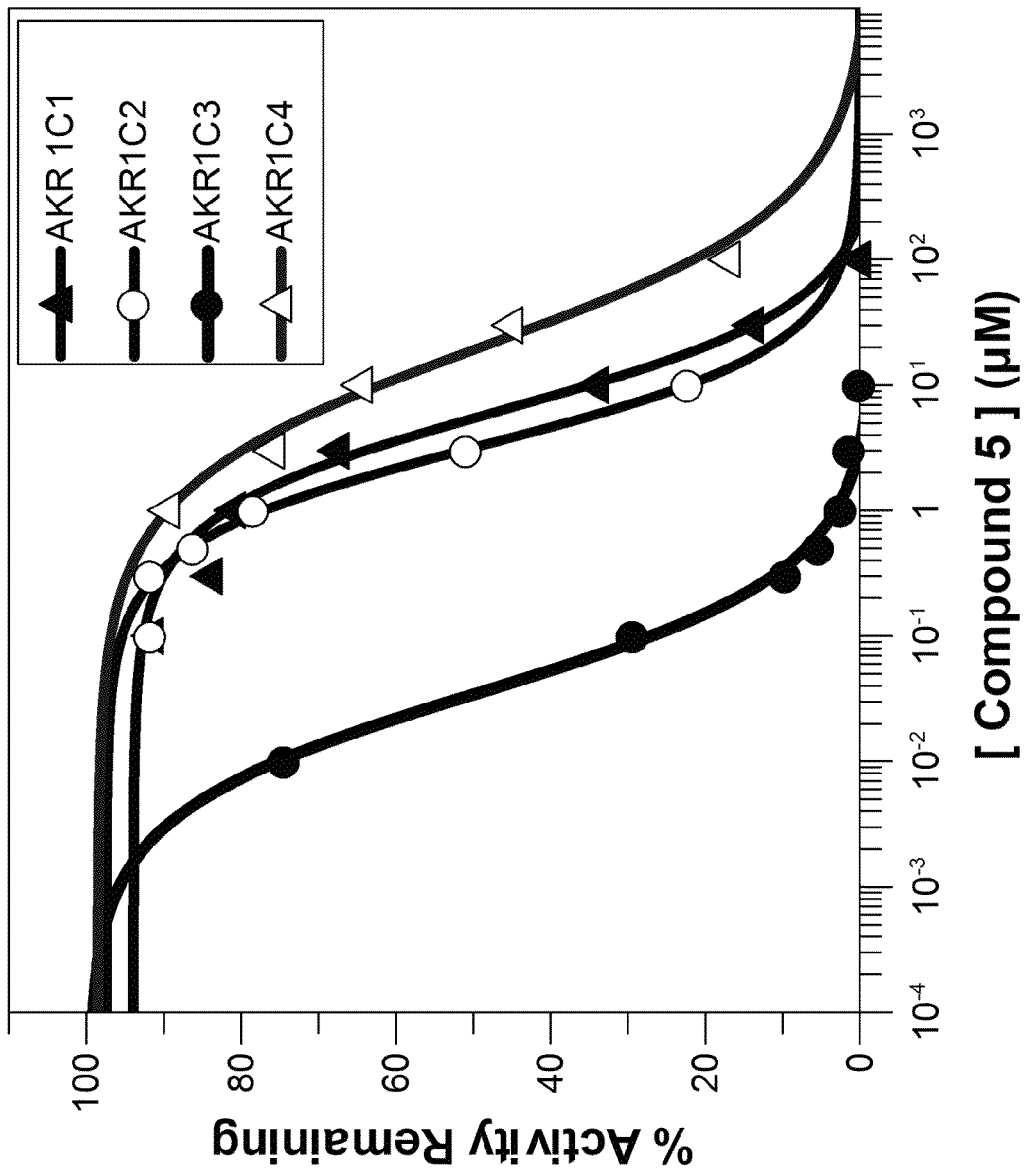
FIG. 15 is a graph illustrating the inhibition of recombinant AKR1C3 with compound 5 (3-[N-(4-nitrophenyl)amino)] benzoic acid).
Figure 23:
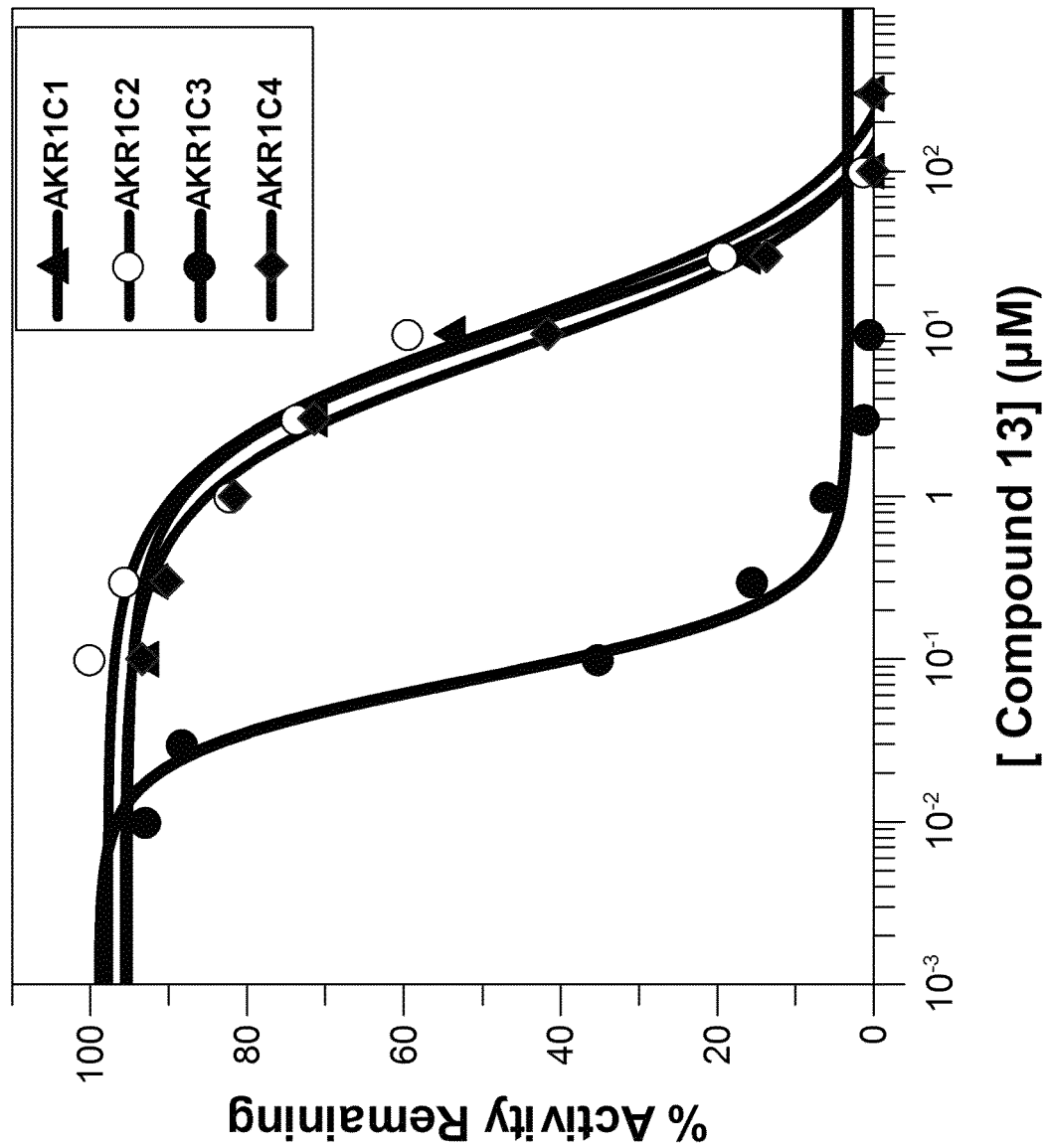
FIG. 23 is a set of graphs illustrating the selective inhibition of AKR1C3 by compound 13, 3-[(4-nitronaphthalen-1-yl) amino)benzoic acid.
Figure 24A:
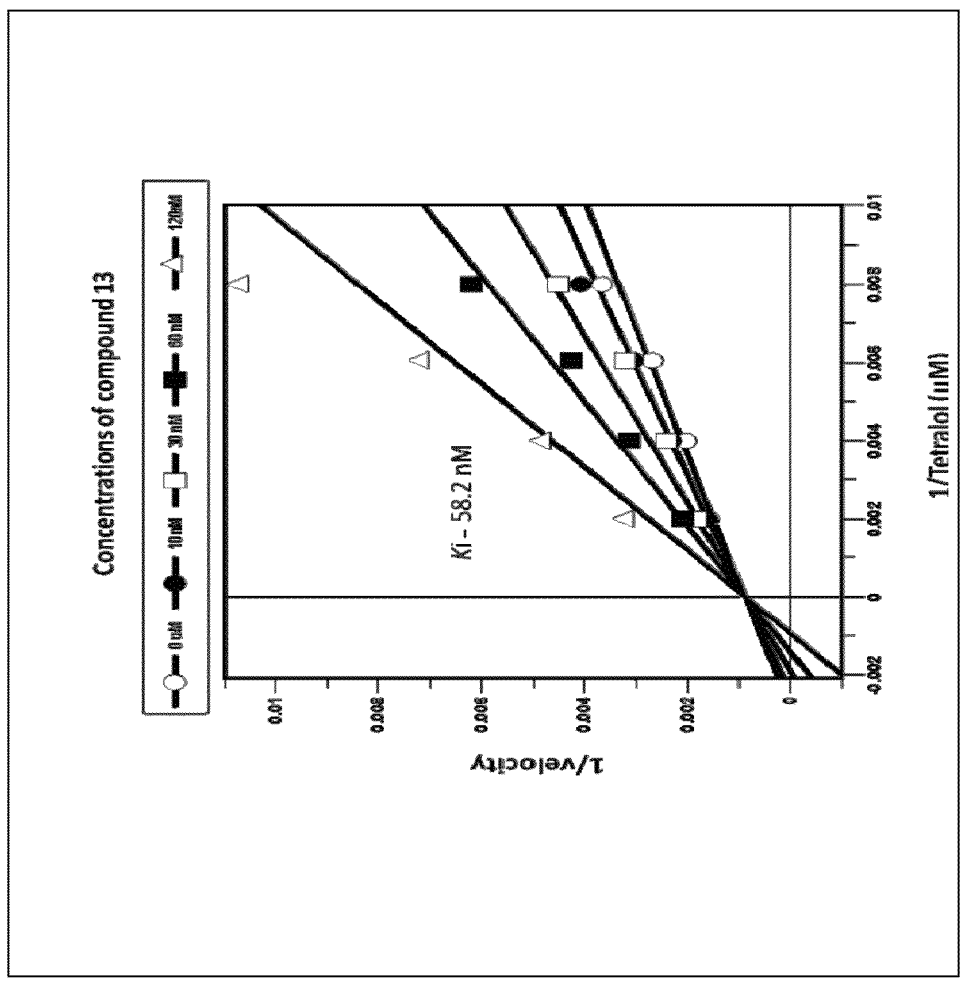
FIGS. 24A and B illustrates competitive inhibition of AKR1C3 by compound 13, 3-[(4-nitronaphthalen-1-yl) amino)benzoic acid using S-tetraol (A) and Δ$^4$-andorstene-3, 17-dione (B) yielding a Ki value s of 58.2 nM and 2.47 µM respectively.
Figure 24B:
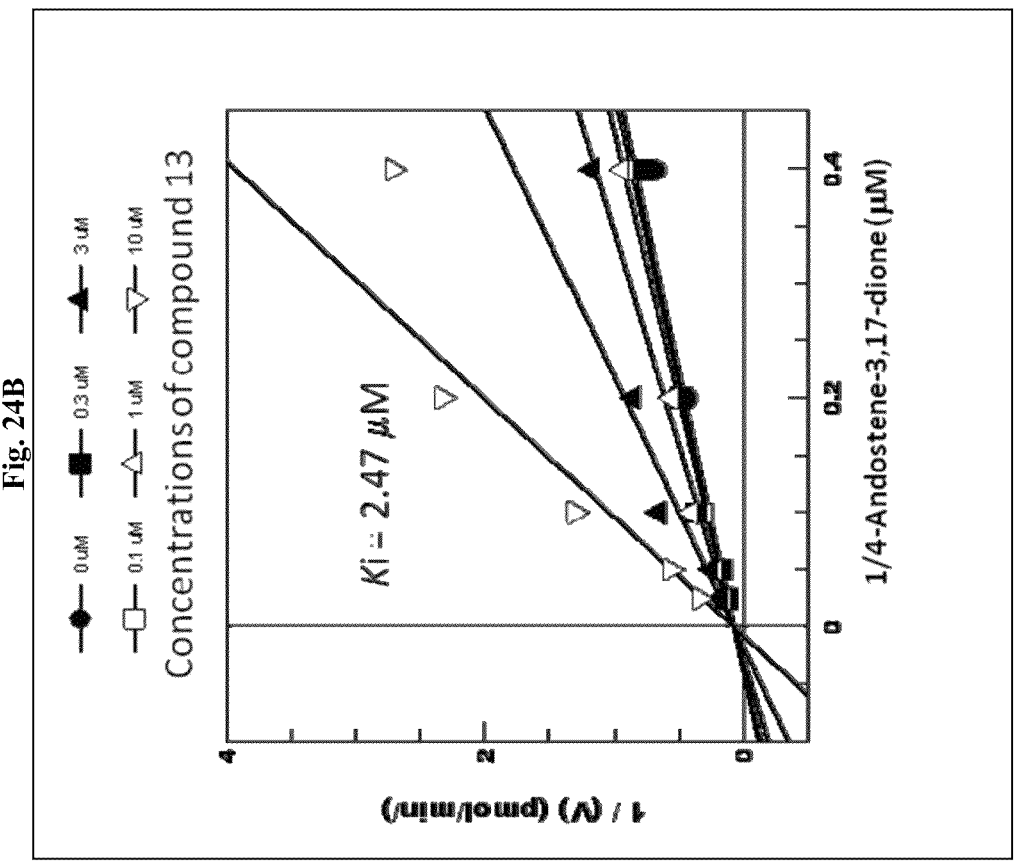
Figure 25:
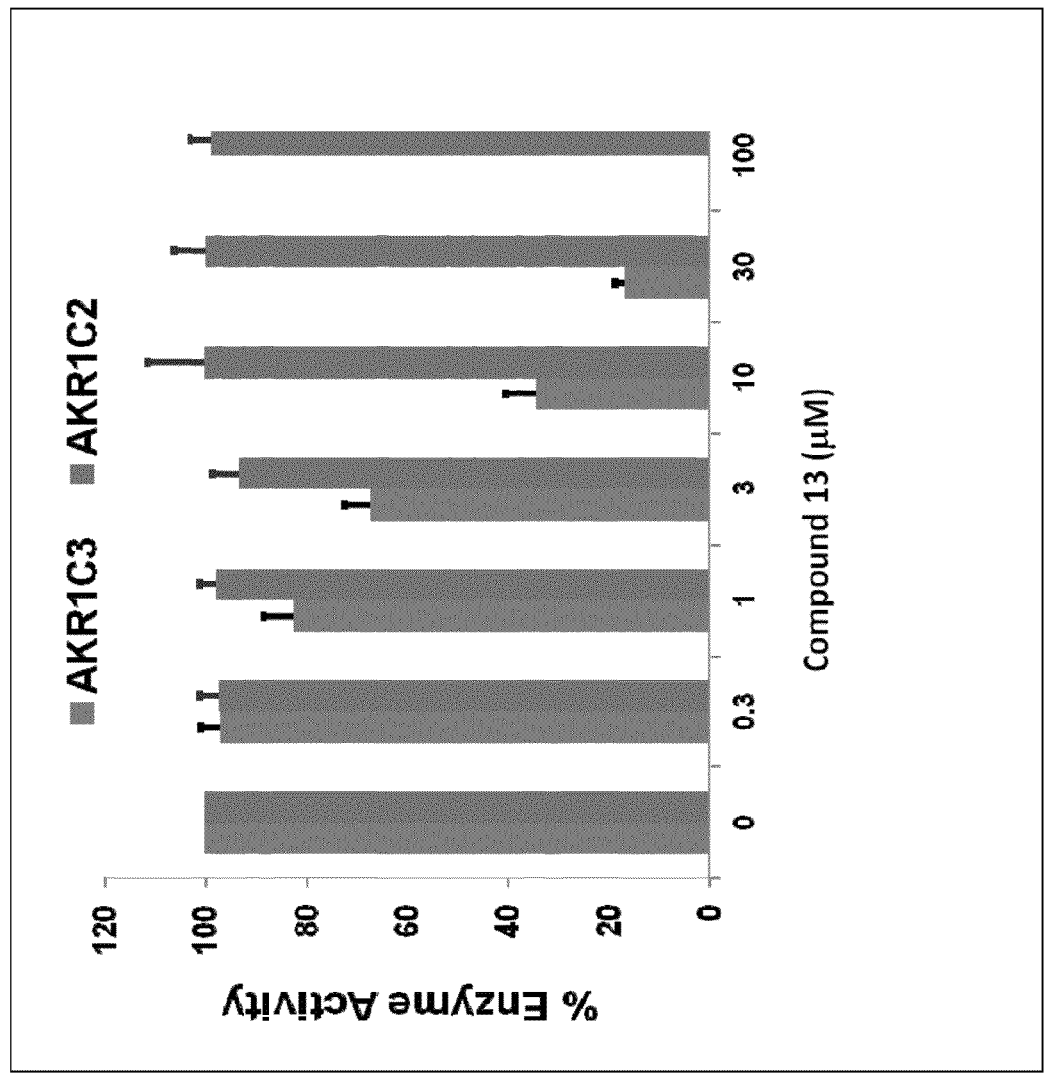
FIG. 25, illustrates the selective inhibition of AKR1C3 by compound 13, 3-[(4-nitronaphthalen-1-yl)amino)benzoic acid, using the conversion of [$^3$H]-Δ$^4$-andorstene-3,17-dione to testosterone to monitor AKR1C3 activity (blue) and the conversion of [$^3$H]-5α-DHT to monitor AKR1C2 activity (red).
Figures 26A, 26B:
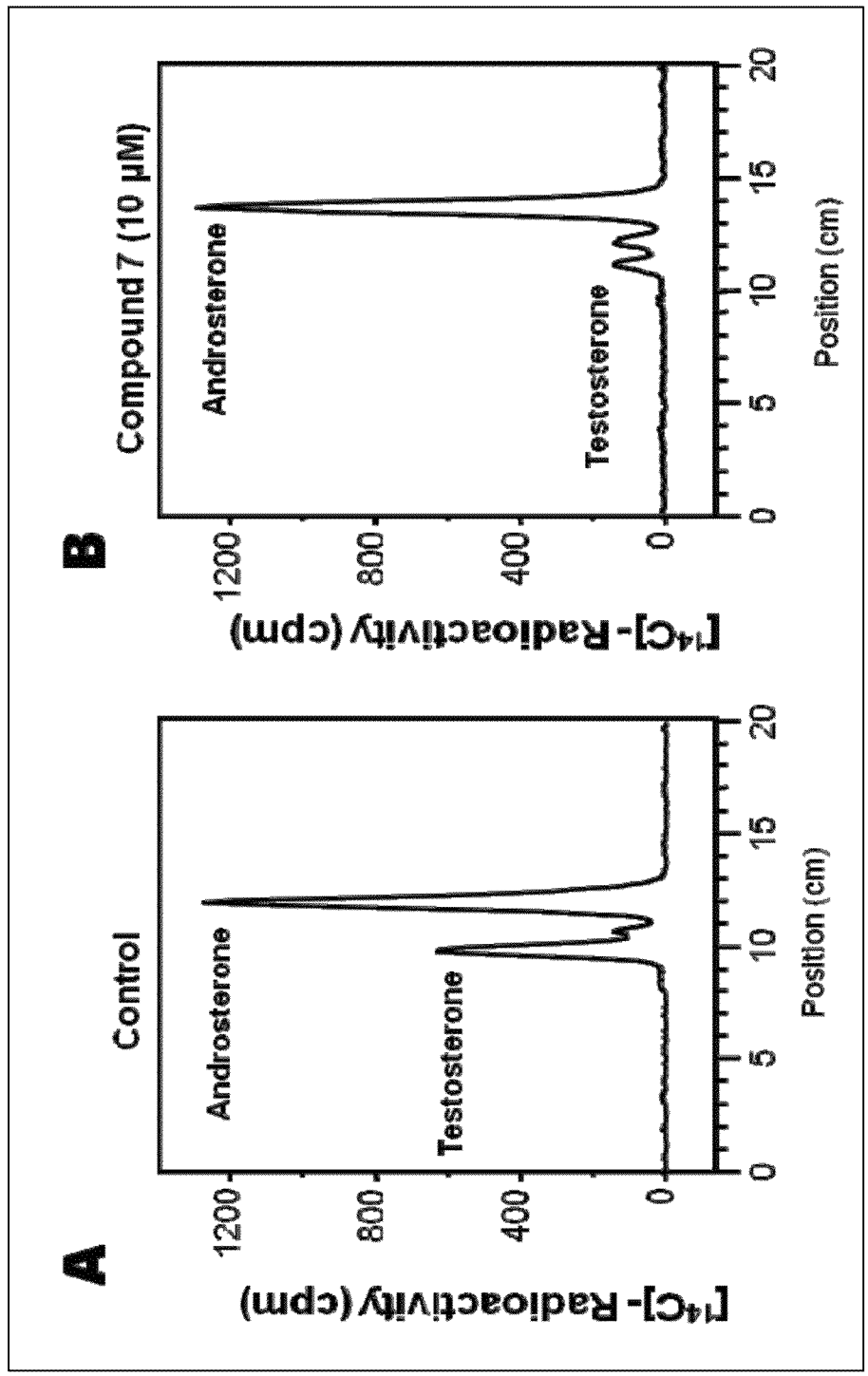
FIGS. 26A-26D, illustrates the ability of compound 7, 3-[N-(4-trifluoromethylphenyl)amino]benzoic acid (FIGS. 26A and 26B) and compound 13, 3'-[(4-nitronaphthalen-1-yl)amino]benzoic acid (FIGS. 26C and 26D) to block testosterone production in LNCaP prostate cancer cells stably transfected with AKR1C3.
Figures 26C, 26D:
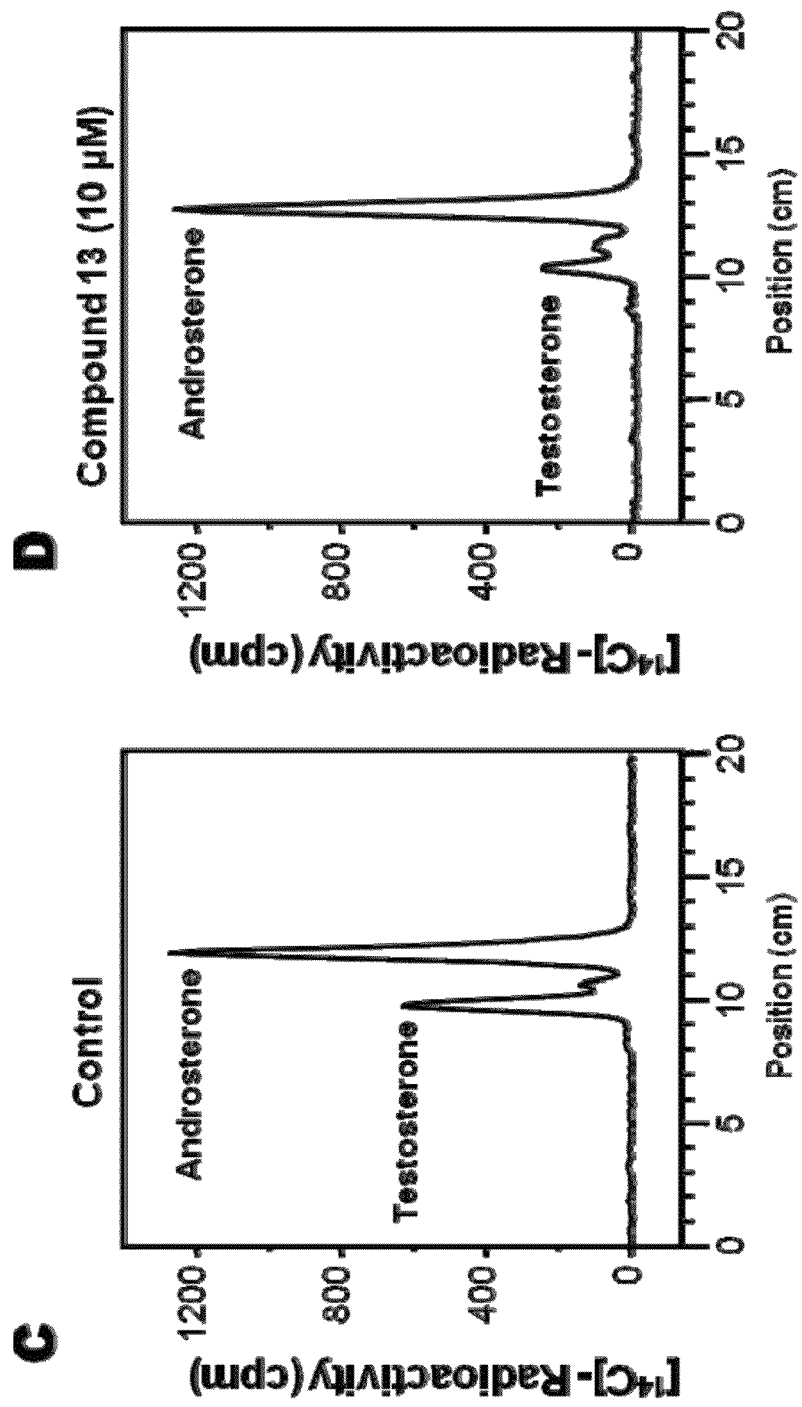

The primary screen was also modified to report the following ratio: AKR1C2 $IC_{50}$ value:AKR1C3 $IC_{50}$ value. A high ratio reflects a high selectivity for AKR1C3 and data are used to generate heat-maps, FIG. 14. This method is preferred to measuring percent inhibition using a single concentration of 1.0 µM inhibitor, since this single point method is prone to identifying false positives. Using this assay lead compounds 3-[N-(4-nitrophenyl)amino]-benzoic acid in the N-phenylaminobenzoate series was identified as inhibiting AKR1C3 in the low nanomolar range with a selectivity of 100-fold over AKR1C2 (FIG. 15). A similar result was obtained for the inhibition of AKR1C3 by compound 13, (3'-[(4-nitronaphthalen-1-yl)amino]benzoic acid), FIG. 23. Patterns of inhibition are then obtained using S-tetralol as substrate where competitive inhibition of the E.NADP+.S-tetralol complex is observed for compound 13, FIG. 24A; and competitive inhibition of the E.NADPH.Δ4-AD complex is observed for compound 13, FIG. 24B. Once identified, leads are confirmed by measuring their selectivity and potency to inhibit only the AKR1C3 catalyzed reduction of $[^3H]$-$\Delta^4$-AD to testosterone without affecting 20-ketosteroid reduction of progesterone catalyzed by AKR1C1 or 3-ketoreduction of 5α-DHT catalyzed by AKR1C2 and AKR1C4. This is illustrated to demonstrate the selectivity of compound 13, (3'-[(4-nitronaphthalen-1-yl)amino]benzoic acid) for AKR1C3, FIG. 25. The leads may then be moved into secondary in vitro screens (complete screen against all human AKR isoforms; COX-1 and COX-2; and other relevant human 17β-HSD isoforms); tertiary screens using cell-based assays (inhibition of AKR1C3 mediated testosterone production and AKR1C3 mediated cell proliferation in prostate cancer cell lines; and modulation of the androgen receptor in reporter gene assays); and quaternary screens in xenograft models of CRPC. When bifunctional AKR1C3 and SARMs are sought the androgen receptor reporter gene assay is moved up in sequence.

LNCaP Models for AKR1C3 Inhibitor Screening

LNCaP cells were stably transfected with AKR1C3 using the retroviral construct pLNCX-AKR1C3, and its expression was documented using both RT-PCR and immunoblot analysis using an isoform specific monoclonal AKR1C3 antibody (Byrns et al., 2012, J. Steroid Biochem. Mol. Biol. 130:7-15). Metabolism studies of 0.1 µM and 5.0 µM $[^{14}C]$-$\Delta^4$-AD were conducted in LNCaP and LNCaP-AKR1C3 cells with the anticipation that the transfected cells would form more testosterone. The bulk of the metabolites formed in LNCaP cells were found in the aqueous phase. When this phase was treated with β-glucuronidase (200 units/mL at pH 6.6) and re-extracted, androsterone was the predominate metabolite released into the organic soluble fraction providing evidence for the formation of androsterone-3α-glucuronide. When LNCaP-AKR1C3 transfected cells were used, the bulk of the metabolites were again found in the aqueous phase. However, β-glucuronidase treatment of the aqueous phase yielded both androsterone and testosterone, providing evidence for testosterone formation by these cells. When the LNCaP-AKR1C3 cells were treated with either compound 7 (3-[N-(4-trifluoromethylphenyl)amino]benzoic acid) or compound 13, (3'-[(4-nitronaphthalen-1-yl)amino]benzoic acid), there was a significant decline in the amount of testosterone that was formed from $\Delta^4$-AD (FIG. 26A-26D). These data indicated that these cells could be used in cell-based screens to measure the efficacy and potency of lead compounds targeting AKR1C3.

AR-Luciferase Reporter Gene Assay

HeLa-AR3A-PSA-(ARE)$_4$-Luc13 cells expressing an AR responsive firefly luciferase gene construct were plated in a 96-well plate at $1.5 \times 10^4$ cell/100 µl/well in phenol red free MEM supplemented with 5% charcoal stripped FBS, 1% Pen/Strep, 2 mM L-Glutamine, Geneticin (500 µg/ml) and hygromycin (200 µg/ml). The cells were incubated for 6-8 hours after which time the media was aspirated and fresh media containing either 0.1 nM 5α-DHT or 0.5 nM R1881 (a non-metabolizable ligand for the AR) and increasing concentrations of SARM was added to the cells. The assay was performed in triplicate. The cells were incubated for 20 h at 37° C. and 5% $CO_2$ and luciferase expression in the cells was measured using the BrightGlo luciferase assay kit according to the manufacturer's instructions. Briefly, after 20 h, the cells were allowed to equilibrate to the room temperature. The luciferase substrate was added to the cells and the luminescence in each well was measured on a BIOTEK Synergy 2 plate reader. The ratio of the luminescence in the cell treated with a SARM and those treated with 5α-DHT alone was used as an index of the AR transcriptional activity at each SARM concentration. These data indicated that these cells could be used in cell-based screens to measure the efficacy and potency of lead compounds targeting AR.

Figure 27A:
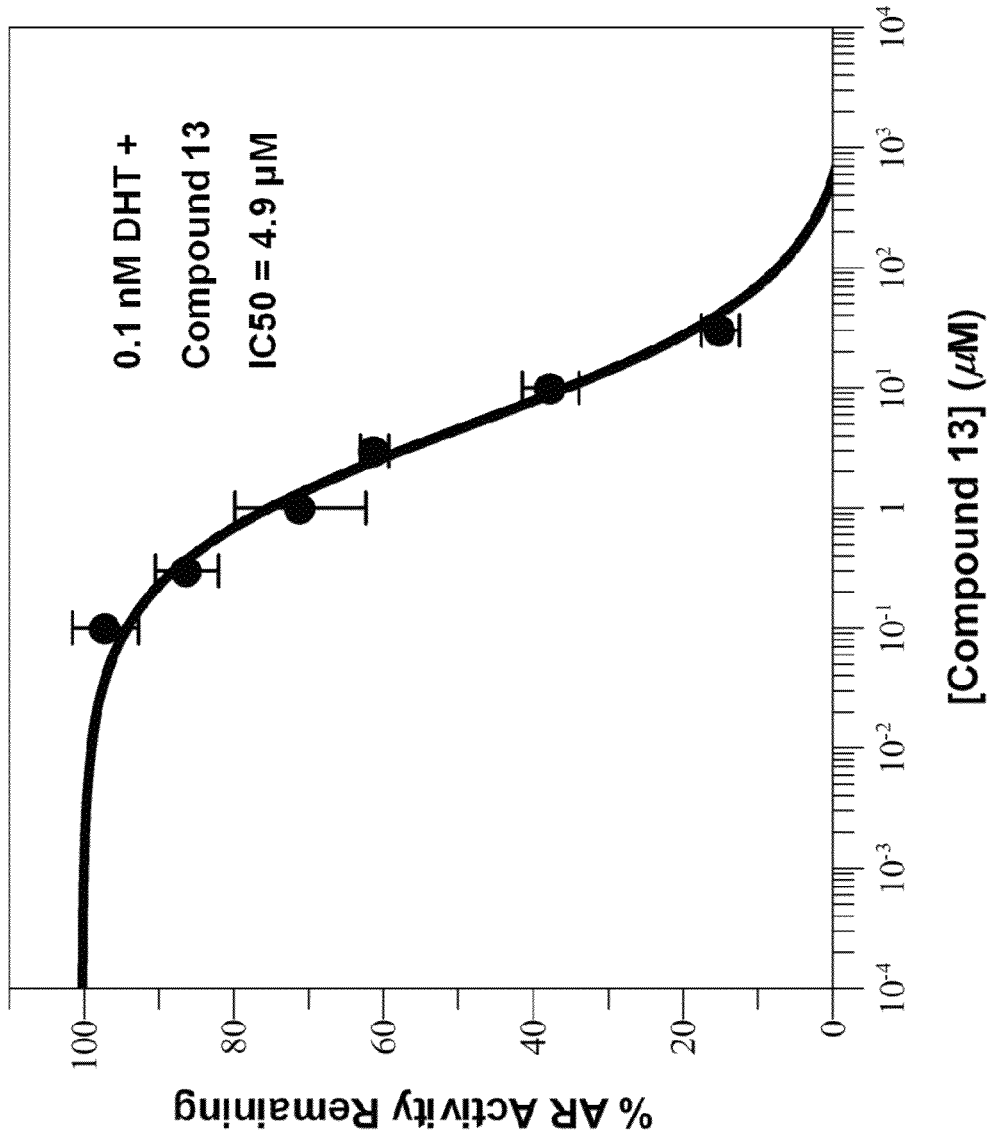
FIGS. 27A and B illustrates the ability of compound 13, (3-[(4-nitronaphthalen-1-yl)amino)]benzoic acid) to acts as an AR antagonist by blocking 5α-DHT mediated trans-activation of the AR in HeLa Cells (FIG. 27A); and by blocking 0.5 nM R1881 mediated trans-activation of the AR in HeLa cells.
Figure 27B:
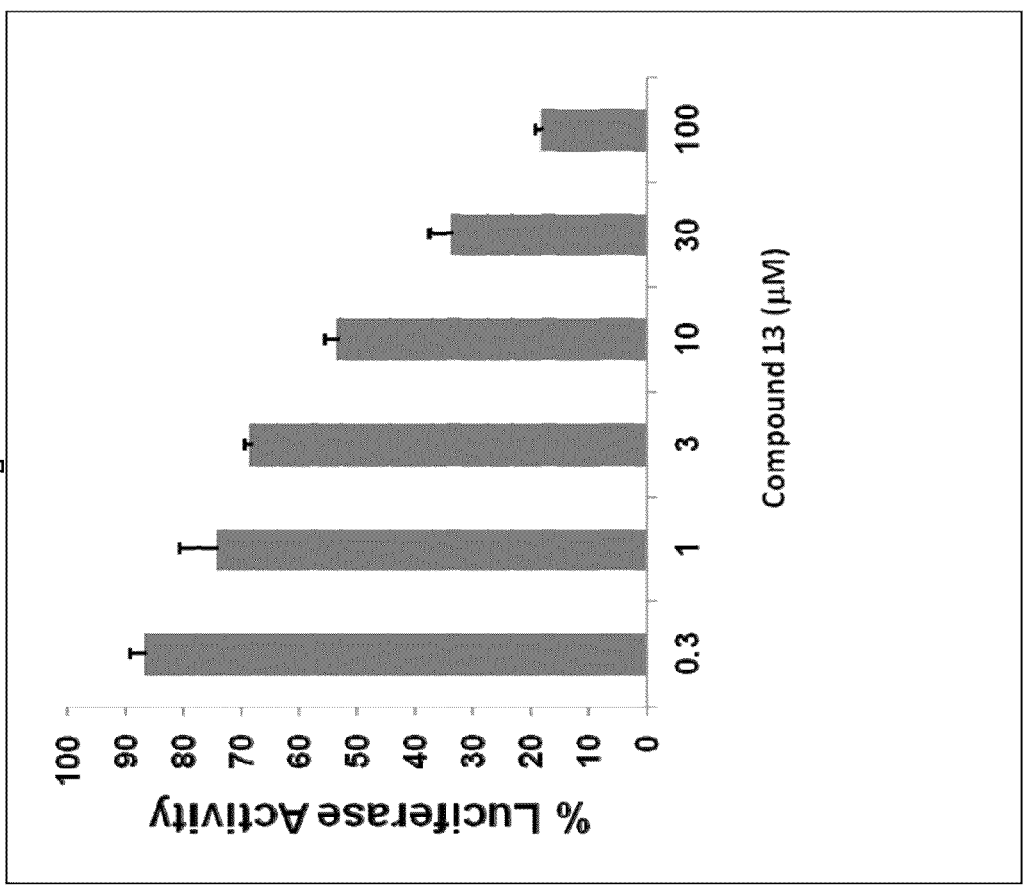

When compounds in this invention, such as (3-((4-nitronaphthalen-1-yl)amino)benzoic acid, were used in this assay it was found that they could block the trans-activation of the AR observed with both 0.1 nM 5α-DHT yielding an $EC_{50}$ value=4.9 µM (FIG. 27A) and 0.5 nM R1881 yielding an $EC_{50}$ value=11.1 µM (FIG. 27B) and were AR antagonists in this assays. These data indicated that compounds in the invention can act as bifunctional AKR1C3 inhibitors and SARMs.

AR Ligand Binding Assays

Figure 28:
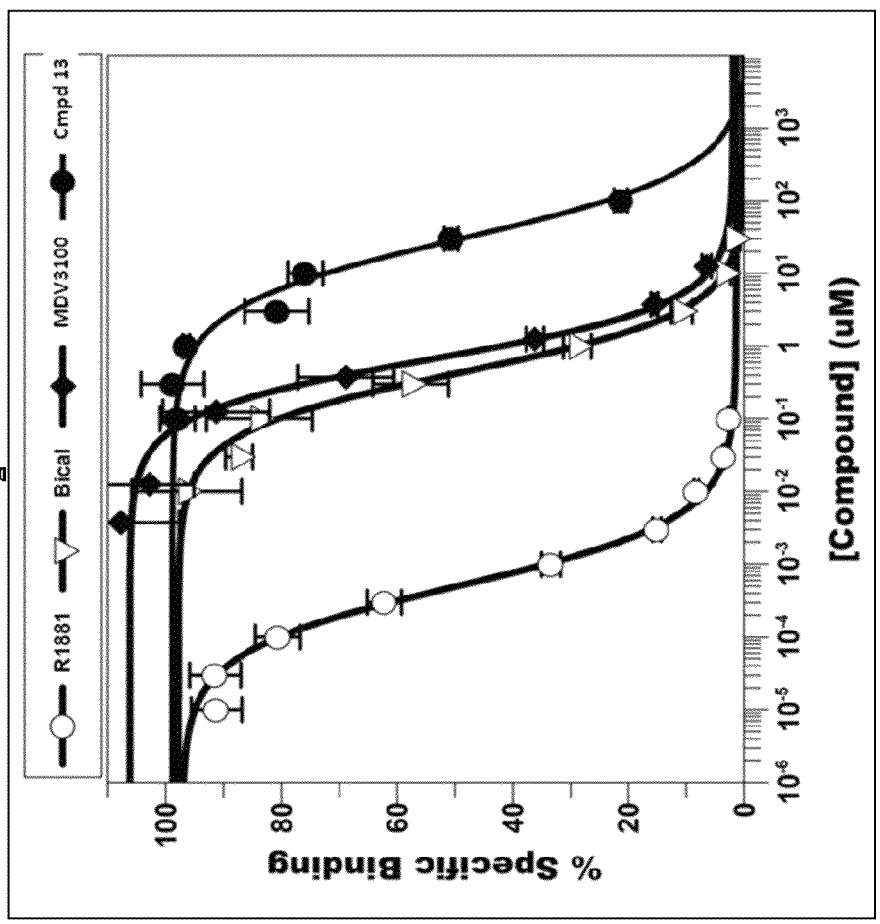
FIG. 28 illustrates the ability of compound 13, (3-[(4-nitronaphthalen-1-yl)amino)]benzoic acid) to competitively displace [$^3$H]-R1881 binding from the AR. Its potency is compared unlabeled R1881 IC$_{50}$=0.5 nM; Biaclutamide IC$_{50}$=430 nM; and MDV 3100 IC$_{50}$=660 nM. Compound 13 gave an IC$_{50}$ value of 30 µM.
Figure 29:
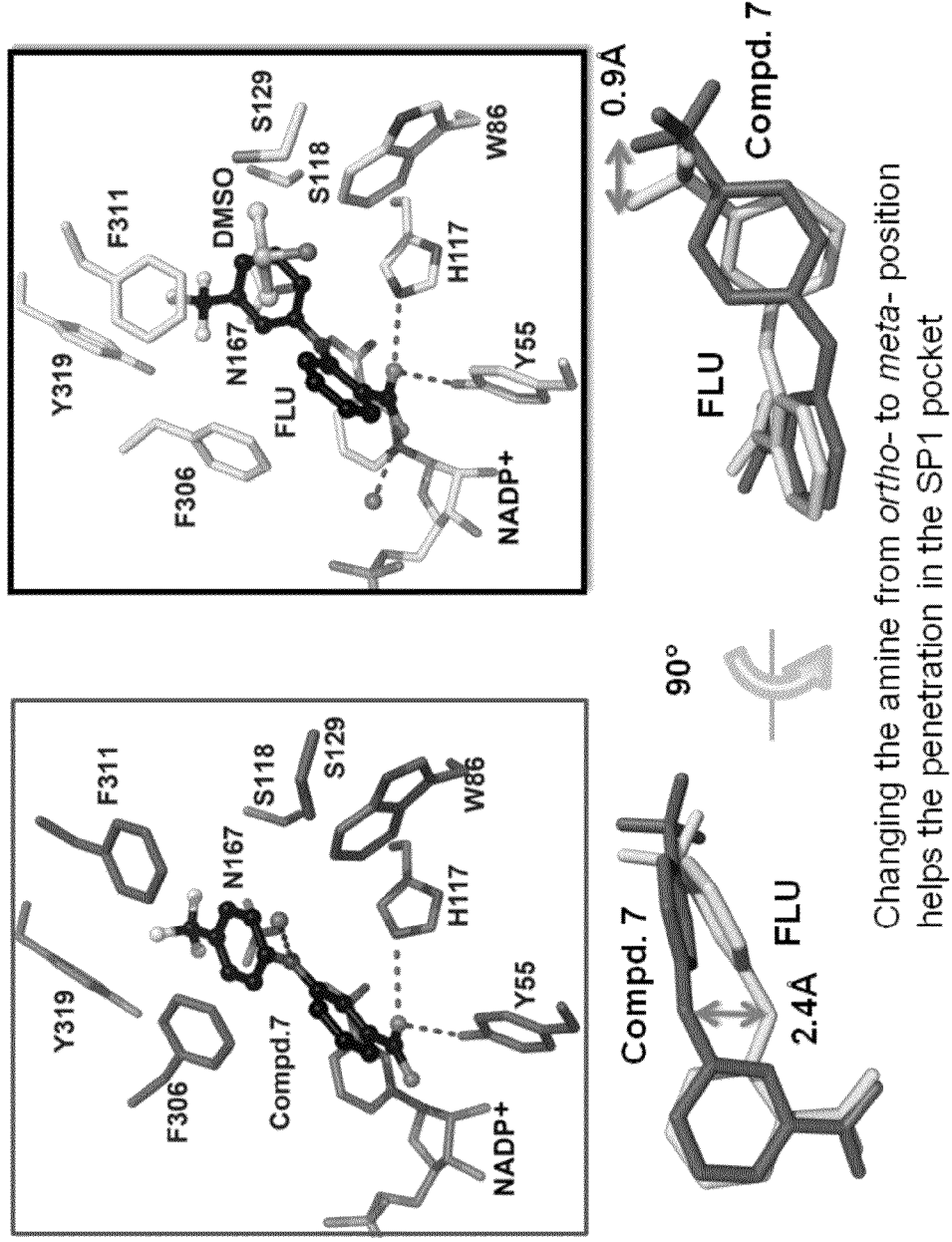
FIG. 29 displays the X-ray crystal structure of the AKR1C3.NADP+. 3-[N-(4-trifluoromethylphenyl)amino] benzoic acid complex (PDB: 4DBU) and the x-ray crystal structure of AKR1C3.NADP+.flufenamic acid complex (PDB: 1S2C), illustrating the basis of AKR1C3 selectivity.

Briefly, HeLa13 cells are cultured in phenol red free MEM supplemented with 5% CDFBS, 2 mM L-Glutamine and 1% pen/Strep for 72 h after which the cells are harvested and replated in 12 well plates at a seeding density of 400,000 cells/ml/well. The cells were then incubated for 48 h after which the media was aspirated and fresh phenol red free media without ANY supplementation containing 0.5 nM R1881 in the presence and absence of an increasing concentration of cold R1881 or other ligand (biclautamide, MDV3100 or compound 13). The cells were then incubated for 2 h after which unbound radioligand was removed by aspirating the media and washing the cells with DPBS (500 ul). The bound radioligand was then extracted by lysing the cells. This was accomplished by adding 200 ul of Buffer A (2% SDS, 10% glycerol, 10 mM Tris-HCl, pH 6.8). Following lysis, 300 ul of 10 mM Tris-HCl (pH8.0) was added and mixed well. Bound ligand was quantified by scintillation counting and normalized to total protein. The amount of radioactivity when the cells were treated with 2 μM DHT is defined as the non specific binding. The ability of the bifunctional acompoun 13, to displace [$^3$H]-R1881 binding from the AR is shown in FIG. 28.

Crystallography

Crystals were grown by the hanging drop vapor diffusion method at 4° C. The AKR1C3.NADP$^+$.Compound 7 complex was obtained from a 3.0 μL: 3.0 μL mixture of protein solution (9.3 mg/mL AKR1C3, 10 mM potassium phosphate (pH 7.0), 1 mM BME, 1 mM EDTA, 2% (v/v) DMSO, 2.0 mM compound 7, and 2.0 mM NADP$^+$) and reservoir solution (0.1 M 2-(N-morpholino)ethanesulfonic acid (pH 6.0), 15% (w/v) polyethylene glycol 8000). The AKR1C3.NADP$^+$.Compound 13 complex was obtained from a 3.0 μL: 3.0 μL mixture of protein solution (9.3 mg/mL AKR1C3, 10 mM potassium phosphate (pH 7.0), 1 mM BME, 1 mM EDTA, 3% (v/v) DMSO, 2.0 mM compound 13, and 2.0 mM NADP$^+$) and reservoir solution (0.05 M 2-(N-morpholino) ethanesulfonic acid (pH 6.0), 15% (w/v) polyethylene glycol 8000, 0.14 M NaCl).

Crystals appeared and grew to a suitable size for diffraction in approximately 3 days. Prior to flash-cooling, crystals were soaked for 5 min in a cryoprotective solution containing 16% (w/v) Jeffamine ED-2001. The AKR1C3.NADP$^+$.Compound 7 complex yielded diffraction data to 2.53 Å resolution at beamline X29 (λ=0.9795 Å) and the AKR1C3.NADP$^+$.Compound 13 complex yielded diffraction data to 1.85 Å resolution at beamline X25 (λ=0.9795 Å) of the National Synchrotron Light Source at Brookhaven National Laboratory (Upton, N.Y.). Both crystals are of the P1 space group. The unit cell contains two monomers of AKR1C3. Data were integrated and scaled with HKL2000 and Scalepack (Otwinoswski & Minor, 1997, Methods Enzymol. 276:307). Data collection and reduction statistics are reported in FIG. 38.

Figure 37:
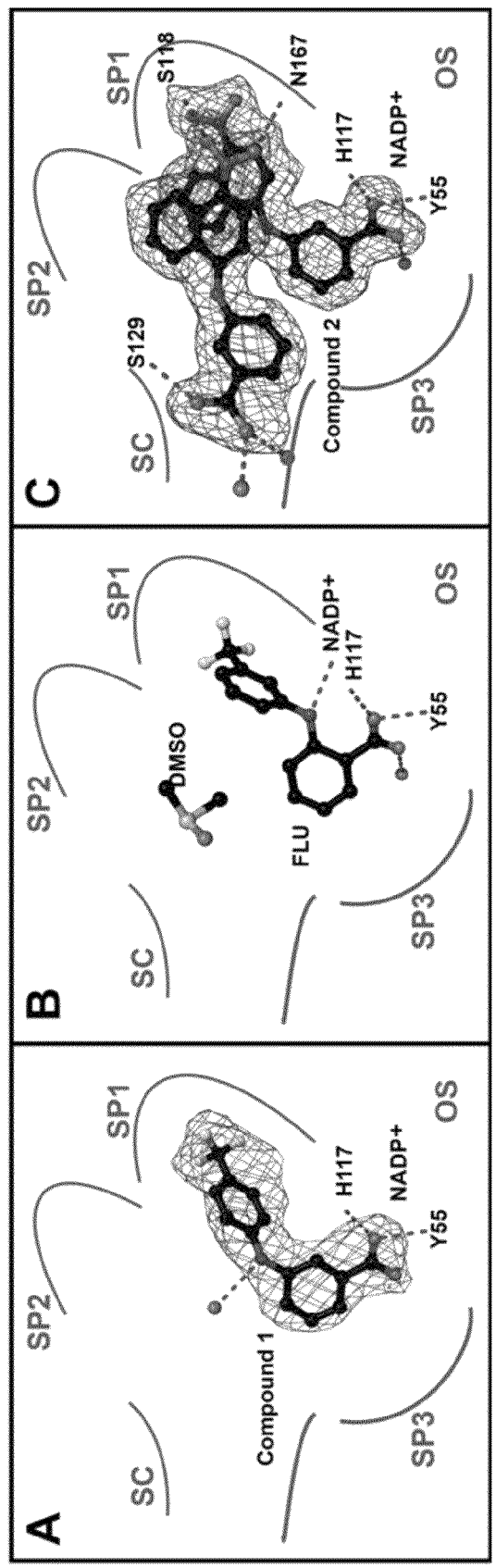
FIG. 37, comprising
Figures 39A, 39B:
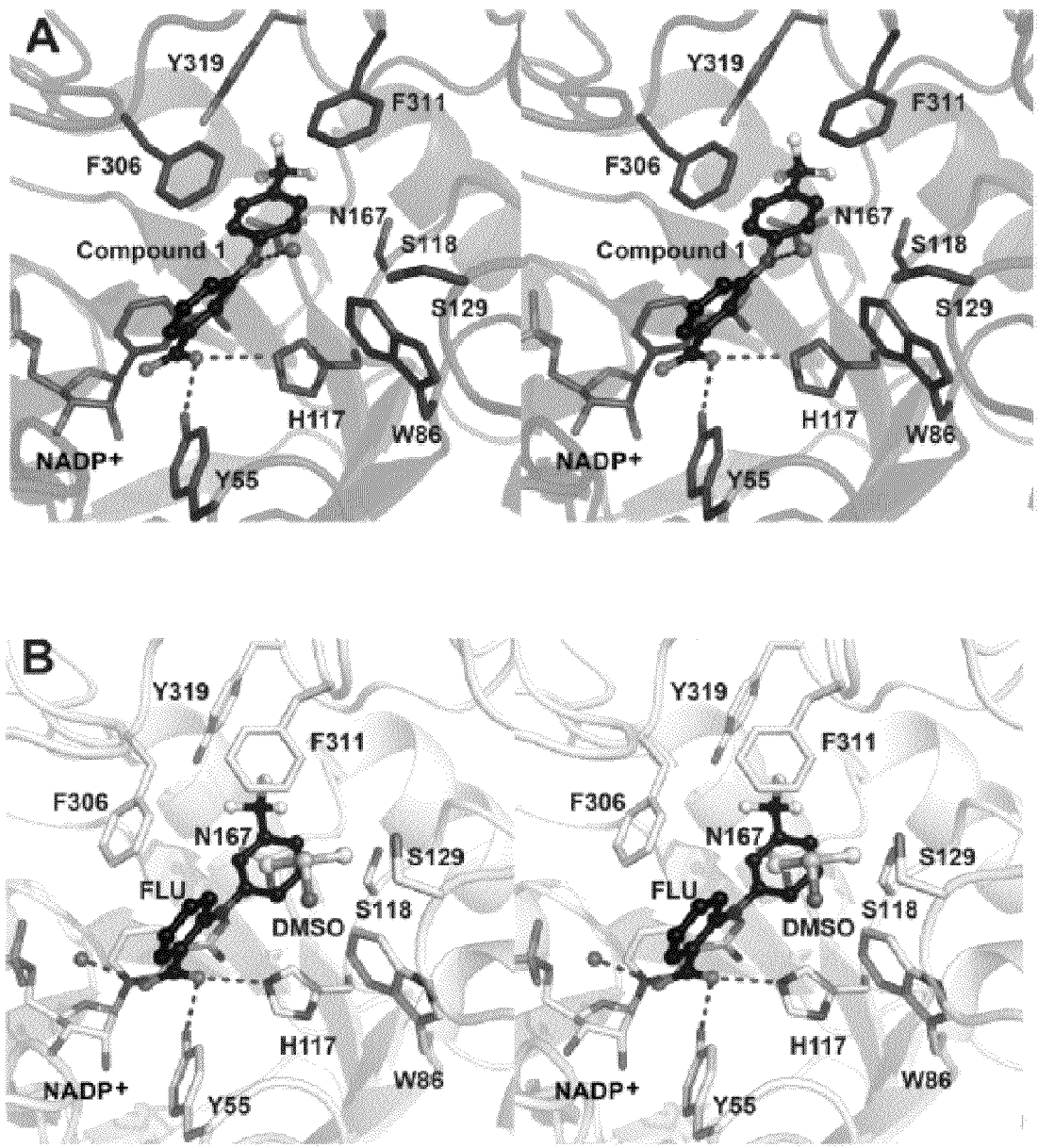
FIGS. 39A-39C, illustrates wall-eyed stereoviews of compound 7 (FIG. 34A), compound 1 (FIG. 34B), and compound 13 (FIG. 34C) in AKR1C3 active site. Inhibitors are shown in ball-and-stick representation. Significant movement of Phe306 and Phe311 was seen in the three structures to accommodate different inhibitors. Water molecules were shown as spheres. Hydrogen bonds were indicated by red dashes. Not all active site residues were shown. The hydrogen bonds that exist between the Compound 1 bridge amine and the carbonyl group on the cofactor nicotinamide head and between the second molecule of Compound 13 and N167 in FIG. 34B are blocked in the view shown.
Figure 39C:
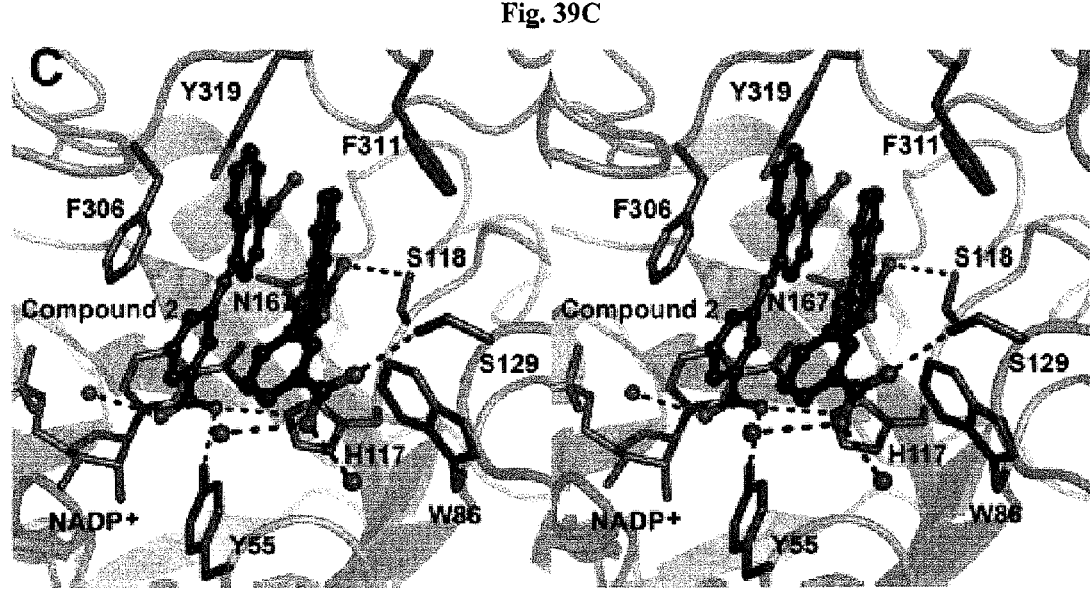

The structure of each complex was solved by molecular replacement performed with PHASER (McCoy et al., 2007, J. Appl. Crust. 40:658) from the CCP4 suite using the coordinates of the AKR1C3.NADP$^+$.indomethacin complex (PDB: 1S2A; Di Constanzo et al., 2008, J. Biol. Chem. 283: 16830) less ligand and solvent molecules as a search model. The programs CNS (Brunger et al., 1998, Acta Cryst. 54:905), PHENIX (Adams et al., 2010, Acta Cryst. Section D 66:213), and COOT (Emsley et al., 2004, Acta Crystallogr. 60:2126) were used for refinement and model fitting. NADP$^+$, compound 7, and compound 13 were built into the electron density map at the final stage of refinement. The correct modeling of the ligands was confirmed by simulated annealing omit maps. The quality of the models were verified with Molprobity and PROCHECK. The refinement statistics are reported in FIG. 37.

Example 1

General Procedure A

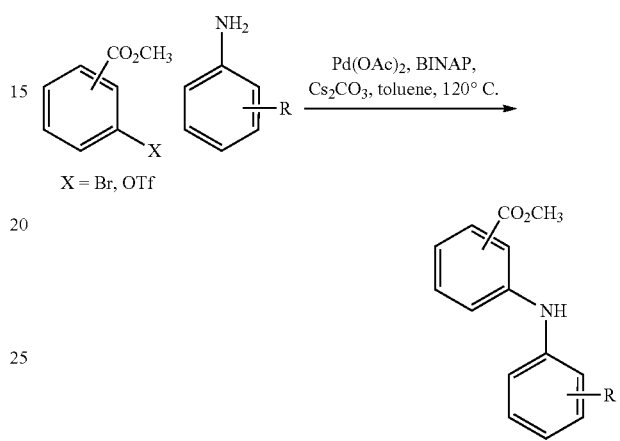

To a solution of bromide (or triflate) (1 equiv) in toluene (0.1 M) was added aniline (1.2 equiv), Cs$_2$CO$_3$ (1.4 equiv) BINAP (0.08 equiv), and Pd(OAc)$_2$ (0.05 equiv) at room temperature. The reaction mixture was allowed to stir at 120° C. for 4-48 h. Once the reaction appeared to be complete by consumption of the bromide (or triflate) by TLC analysis, the mixture was allowed to cool to room temperature, diluted with EtOAc, washed with 2M aq HCl (2×), brine, and dried over sodium sulfate. The solution was concentrated, loaded on silica gel, and purified by silica gel chromatography.

Example 2

General Procedure B

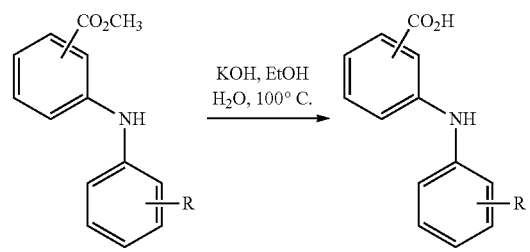

To a solution of the methyl ester (1 equiv) in EtOH (0.2 M) was added KOH (2 equiv per ester) in water (0.2 M) at room temperature. The reaction mixture was allowed to stir at 100° C. for 1-6 h. Once the reaction appeared complete by TLC analysis, EtOH was evaporated from the reaction mixture, the resultant solution was cooled to 0° C. and acidified to pH 2 w

Example 3

N-(3-Trifluoromethylphenyl)anthranilic acid methyl ester

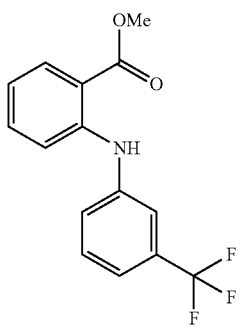 [SMILES: COC(=O)c1ccccc1Nc1cccc(C(F)(F)F)c1]

Reaction of methyl 2-(trifluoromethanesulfonyloxy)benzoate with 3-aminobenzotrifluoride according to general procedure A provided flufenamic acid methyl ester as a yellow oil (71% yield). $^1$H NMR (CDCl$_3$, 500 MHz): δ=9.60 (s, 1H), 8.01 (dd, J=8.0, 1.7 Hz, 1H), 7.50 (s, 1H), 7.35-7.47 (m, 3H), 7.27-7.34 (m, 2H), 6.83 (t, J=7.1 Hz, 1H), 3.93 (s, 3H). $^{13}$C NMR (CDCl$_3$, 125 MHz): δ=169.1, 147.0, 141.9, 134.5, 132.0, 130.1, 124.8, 119.8, 118.6, 118.3, 114.6, 113.3, 52.1.

Example 4

Flufenamic Acid (Compound 1)

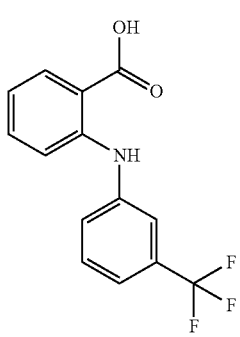 [SMILES: O=C(O)c1ccccc1Nc1cccc(C(F)(F)F)c1]

Reaction of flufenamic acid methyl ester according to general procedure B provided flufenamic acid (Compound 1) as a white solid (55% yield). $^1$H NMR (DMSO, 500 MHz): δ=13.14 (bs, 1H), 9.66 (s, 1H), 7.93 (d, J=7.9 Hz, 1H), 7.40-7.60 (m, 4H), 7.25-7.36 (m, 2H), 6.89 (t, J=7.5 Hz, 1H). $^{13}$C NMR (DMSO, 125 MHz): δ=169.5, 145.4, 142.0, 134.1, 131.9, 130.5, 123.7, 118.9, 118.5, 116.3, 114.9, 114.5. HRMS (ES) Calcd. for C$_{14}$H$_{10}$F$_3$NO$_2$: 280.0585 (M-H$^-$). found 280.0590 (M-H$^-$).

Example 5

N-Phenylanthranilic acid methyl ester

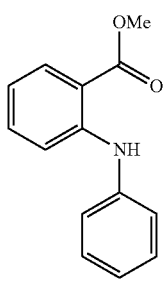

Reaction of methyl 2-(trifluoromethanesulfonyloxy)benzoate with aniline according to general procedure A provided methyl ester of 2 as a yellow oil (99% yield). $^1$H NMR (CDCl$_3$, 500 MHz): δ=9.48 (s, 1H), 7.97 (d, J=8.0 Hz, 1H), 7.22-7.40 (m, 6H), 7.10 (t, J=7.3 Hz, 1H), 6.74 (t, J=7.5 Hz, 1H), 3.91 (s, 3H). $^{13}$C NMR (CDCl$_3$, 125 MHz): δ=169.1, 148.2, 141.0, 134.3, 131.8, 129.6, 123.8, 122.8, 117.3, 114.3, 112.2, 51.9.

Example 6

N-Phenylanthranilic acid (Compound 2)

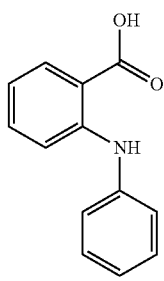 [SMILES: O=C(O)c1ccccc1Nc1ccccc1]

Reaction of methyl ester of Compound 2 according to general procedure B provided Compound 2 as a white solid (57% yield). $^1$H NMR (DMSO, 500 MHz): δ=13.03 (bs, 1H), 9.63 (bs, 1H), 7.91 (d, J=7.9 Hz, 1H), 7.30-7.45 (m, 3H), 7.17-7.27 (m, 3H), 7.07 (t, J=7.3 Hz, 1H), 6.78 (t, J=7.5 Hz, 1H). $^{13}$C NMR (DMSO, 125 MHz): δ=169.9, 147.0, 140.5, 134.1, 131.8, 129.4, 123.0, 121.3, 117.4, 113.7, 112.6. HRMS (ES) Calcd. for C$_{13}$K$_1$NO$_2$: 212.0712 (M-H$^-$). found 212.0709 (M-H$^-$).

Example 7

3-Phenylamino benzoic acid methyl ester

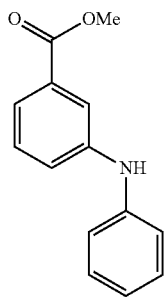 [SMILES: COC(=O)c1cccc(Nc2ccccc2)c1]

Reaction of methyl 3-bromobenzoate with aniline according to general procedure A provided methyl ester of Compound 3 as a yellow oil (94% yield). $^1$H NMR (CDCl$_3$, 500 MHz): δ=7.73 (s, 1H), 7.56 (d, J=7.6 Hz, 1H), 7.22-7.35 (m, 4H), 7.10 (d, J=8.5 Hz, 2H), 7.00 (t, J=7.4 Hz, 1H), 5.81 (s, 1H), 3.91 (s, 3H). $^{13}$C NMR (CDCl$_3$, 125 MHz): δ=167.3, 143.9, 142.6, 131.6, 129.7, 129.6, 122.0, 121.9, 121.7, 118.7, 118.4, 52.3.

Example 8

3-Phenylamino benzoic acid (Compound 3)

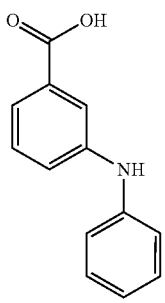 [SMILES: O=C(O)c1cccc(Nc2ccccc2)c1]

Reaction of methyl ester of Compound 3 according to general procedure B provided Compound 3 as a white solid (74% yield). $^1$H NMR (DMSO, 500 MHz): δ=12.79 (bs, 1H), 8.33 (s, 1H), 7.65 (s, 1H), 7.24-7.38 (m, 5H), 7.10 (d, J=8.5 Hz, 2H), 6.88 (t, J=7.3 Hz, 1H). $^{13}$C NMR (DMSO, 125 MHz): δ=167.4, 143.9, 142.7, 131.7, 129.3, 129.2, 120.4, 120.2, 120.1, 117.5, 116.5. HRMS (ES) Calcd. for $C_{13}K_{11}NO_2$: 212.0712 (M-H$^-$). found 212.0712 (M-H$^-$).

Example 9

4-Phenylamino benzoic acid methyl ester

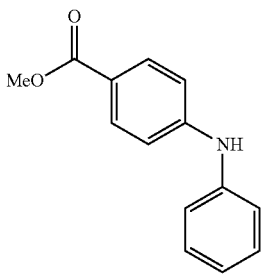 [SMILES: COC(=O)c1ccc(Nc2ccccc2)cc1]

Reaction of methyl 4-bromobenzoate with aniline according to general procedure A provided methyl ester of Compound 4 as a yellow oil (84% yield). $^1$H NMR (CDCl$_3$, 500 MHz): δ=7.92 (d, J=8.8 Hz, 2H), 7.32-7.38 (m, 2H), 7.18 (d, J=7.5 Hz, 2H), 7.09 (m, 1H), 6.99 (d, J=8.8 Hz, 2H), 6.02 (s, 1H), 3.89 (s, 3H). $^{13}$C NMR (CDCl$_3$, 125 MHz): δ=167.2, 148.3, 141.1, 131.7, 129.7, 123.4, 121.5, 120.7, 114.9, 51.9.

Example 10

4-Phenylamino benzoic acid (Compound 4)

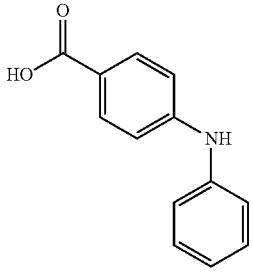 [SMILES: O=C(O)c1ccc(Nc2ccccc2)cc1]

Reaction of methyl ester of Compound 4 according to general procedure B provided 4 as a white solid (81% yield). $^1$H NMR (DMSO, 500 MHz): δ=8.69 (s, 1H), 7.78 (d, J=8.7 Hz, 2H), 7.31 (t, J=7.9 Hz, 2H), 7.17 (d, J=7.6 Hz, 2H), 7.05 (d, J=8.7 Hz, 2H), 6.96 (t, J=7.3 Hz, 1H). $^{13}$C NMR (DMSO, 125 MHz): δ=167.2, 148.0, 141.5, 131.1, 129.3, 121.6, 120.6, 119.1, 114.0. HRMS (ES) Calcd. for $C_{13}K_1NO_2$: 212.0712 (M-H$^-$). found 212.0717 (M-H$^-$).

Example 11

3-[N-(4-Nitrophenyl)amino]benzoic acid methyl ester

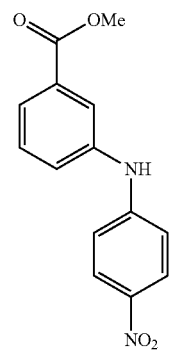 [SMILES: COC(=O)c1cccc(Nc2ccc([N+](=O)[O-])cc2)c1]

Reaction of methyl 3-bromobenzoate with 4-nitroaniline according to general procedure A provided methyl ester of Compound 5 as an orange solid (59% yield). $^1$H NMR (CDCl$_3$, 500 MHz): δ=8.16 (d, J=9.1 Hz, 2H), 7.89 (s, 1H), 7.83 (d, J=7.6 Hz, 1H), 7.47 (t, J=7.8 Hz, 1H), 7.41 (m, 1H), 6.98 (d, J=9.1 Hz, 2H), 6.31 (s, 1H), 3.94 (s, 3H). $^{13}$C NMR (CDCl$_3$, 125 MHz): δ=166.7, 149.7, 140.7, 140.3, 132.2, 130.1, 126.5, 125.9, 125.7, 122.6, 114.4, 52.6.

Example 12

3-[N-(4-nitrophenyl)amino]benzoic acid (Compound 5)

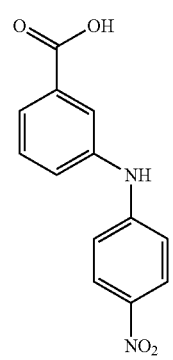 [SMILES: O=C(O)c1cccc(Nc2ccc([N+](=O)[O-])cc2)c1]

Reaction of methyl ester of Compound 5 according to general procedure B provided 5 as an orange solid (30% yield). $^1$H NMR (DMSO, 500 MHz): δ=13.00 (bs, 1H), 9.41 (s, 1H), 8.12 (d, J=9.2 Hz, 2H), 7.78 (s, 1H), 7.64 (m, 1H), 7.46-7.54 (m, 2H), 7.10 (d, J=9.2 Hz, 2H). $^{13}$C NMR (DMSO, 125 MHz): δ=166.9, 150.1, 140.6, 138.5, 132.1, 129.8, 126.1, 124.3, 123.8, 120.7, 113.8. HRMS (ES) Calcd. for $C_{13}H_{10}N_2O_4$: 257.0562 (M-H$^-$). found 257.0556 (M-H$^-$).

Example 13

3-[N-(4-Acetylphenyl)amino]benzoic acid methyl ester

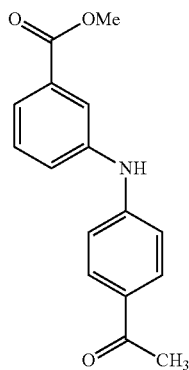 [SMILES: COC(=O)c1cccc(Nc2ccc(C(C)=O)cc2)c1]

Reaction of methyl 3-bromobenzoate with 4'-aminoacetophenone according to general procedure A provided methyl ester of 6 as a white solid (84% yield). $^1$H NMR (CDCl$_3$, 500 MHz): δ=7.89 (d, J=8.7 Hz, 2H), 7.85 (s, 1H), 7.73 (m, 1H), 7.36-7.42 (m, 2H), 7.03 (d, J=8.5 Hz, 2H), 6.31 (s, 1H), 3.92 (s, 3H), 2.55 (s, 3H). $^{13}$C NMR (CDCl$_3$, 125 MHz): δ=196.7, 167.0, 147.9, 141.3, 131.8, 130.9, 129.9, 129.8, 124.6, 124.2, 121.2, 115.1, 52.5, 26.4.

Example 14

3-[N-(4-Acetylphenyl)amino]benzoic acid (Compound 6)

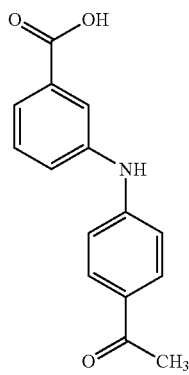 [SMILES: CC(=O)c1ccc(Nc2cccc(C(=O)O)c2)cc1]

Reaction of methyl ester of 6 according to general procedure B provided Compound 6 as a yellow solid (43% yield). $^1$H NMR (DMSO, 500 MHz): δ=8.98 (s, 1H), 7.85 (d, J=8.2 Hz, 2H), 7.75 (s, 1H), 7.54 (m, 1H), 7.40-7.46 (m, 2H), 7.09 (d, J=8.3 Hz, 2H), 2.47 (s, 3H). $^{13}$C NMR (DMSO, 125 MHz): δ=195.6, 167.2, 147.9, 141.8, 131.9, 130.5, 129.7, 128.3, 122.9, 122.4, 119.3, 114.5, 26.2. HRMS (ES) Calcd. for $C_{15}H_{13}NO_3$: 278.0793 (M+Na$^+$). found 278.0800 (M+Na$^+$).

Example 15

3-[N-(4-Trifluoromethylphenyl)amino]benzoic acid methyl ester

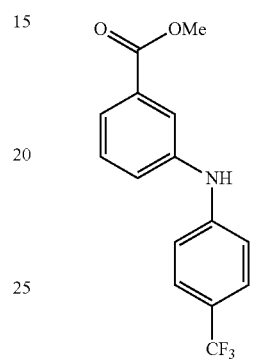

Reaction of methyl 3-bromobenzoate with 4-aminobenzotrifluoride according to general procedure A provided methyl ester of Compound 7 as a white solid (86% yield). $^1$H NMR (CDCl$_3$, 500 MHz): δ=7.82 (s, 1H), 7.71 (d, J=7.6 Hz, 1H), 7.50 (d, J=8.4 Hz, 2H), 7.40 (t, J=7.8 Hz, 1H), 7.33 (m, 1H), 7.08 (d, J=8.5 Hz, 2H), 6.11 (bs, 1H), 3.93 (s, 3H). $^{13}$C NMR (CDCl$_3$, 125 MHz): δ=167.0, 146.3, 141.9, 131.8, 129.8, 127.0, 123.9, 120.5, 116.1, 52.5.

Example 16

3-[N-(4-Trifluoromethylphenyl)amino]benzoic acid (Compound 7)

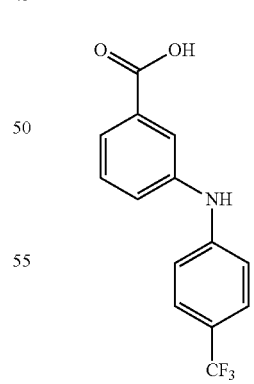

Reaction of methyl ester of Compound 7 according to general procedure B provided 7 as a white solid (90% yield). $^1$H NMR (DMSO, 500 MHz): δ=12.91 (bs, 1H), 8.91 (s, 1H), 7.73 (s, 1H), 7.55 (d, J=8.6 Hz, 2H), 7.52 (m, 1H), 7.40-7.43 (m, 2H), 7.18 (d, J=8.6 Hz, 2H), 2.47 (s, 3H). $^{13}$C NMR (DMSO, 125 MHz): δ=167.2, 146.9, 142.0, 132.0, 129.6, 126.6, 122.5, 122.2, 118.9, 115.2. HRMS (ES) Calcd. for C$_{14}$H$_{10}$F$_3$NO$_2$: 280.0585 (M-H$^-$). found 280.0577 (M-H$^-$).

Example 17

3-[N-(4-Chlorophenyl)amino]benzoic acid methyl ester

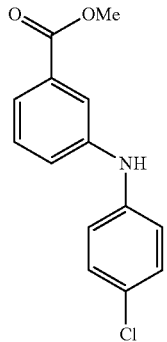 [SMILES: COC(=O)c1cccc(Nc2ccc(Cl)cc2)c1]

Reaction of methyl 3-bromobenzoate with 4-chloroaniline according to general procedure A provided methyl ester of Compound 8 as a yellow oil (52% yield). $^1$H NMR (CDCl$_3$, 500 MHz): δ=7.70 (s, 1H), 7.61 (d, J=7.6 Hz, 1H), 7.33 (t, J=7.9 Hz, 1H), 7.21-7.27 (m, 3H), 7.01 (d, J=8.8 Hz, 2H), 5.78 (s, 1H), 3.91 (s, 3H). $^{13}$C NMR (CDCl$_3$, 125 MHz): δ=167.2, 143.4, 141.4, 131.7, 129.7, 126.7, 122.5, 122.0, 119.8, 118.7, 52.4.

Example 18

3-[N-(4-Chlorophenyl)amino]benzoic acid (Compound 8)

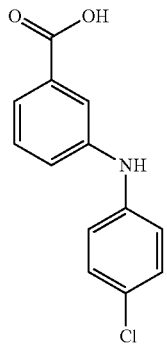 [SMILES: O=C(O)c1cccc(Nc2ccc(Cl)cc2)c1]

Reaction of methyl ester of 8 according to general procedure B provided Compound 8 as a white solid (81% yield). $^1$H NMR (DMSO, 500 MHz): δ=12.83 (bs, 1H), 8.47 (s, 1H), 7.63 (s, 1H), 7.41 (d, J=7.7 Hz, 1H), 7.35 (t, J=7.8 Hz, 1H), 7.26-7.30 (m, 3H), 7.08 (d, J=8.8 Hz, 2H). $^{13}$C NMR (DMSO, 125 MHz): δ=167.3, 143.3, 141.9, 131.8, 129.4, 129.0, 123.4, 120.7, 120.6, 118.5, 117.0. HRMS (ES) Calcd. for C$_{13}$H$_{10}$ClNO$_2$: 246.0322 (M-H$^-$). found 246.0321 (M-H$^-$).

Example 19

3-[N-(4-Bromophenyl)amino]benzoic acid methyl ester

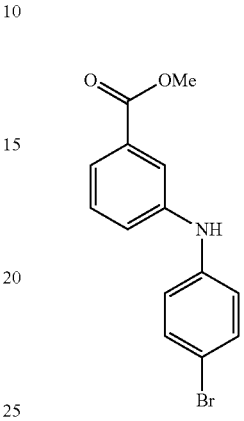

Reaction of methyl 3-bromobenzoate with 4-bromoaniline according to general procedure A provided methyl ester of Compound 9 as a green oil (46% yield). $^1$H NMR (CDCl$_3$, 500 MHz): δ=7.71 (s, 1H), 7.61 (d, J=7.7 Hz, 1H), 7.38 (d, J=8.6 Hz, 2H), 7.34 (t, J=7.9 Hz, 1H), 7.23 (d, J=8.1 Hz, 1H), 6.96 (d, J=8.7 Hz, 2H), 5.81 (s, 1H), 3.91 (s, 3H). $^{13}$C NMR (CDCl$_3$, 125 MHz): δ=167.2, 143.1, 141.9, 132.6, 131.7, 129.7, 122.6, 122.1, 119.9, 118.8, 113.8, 52.4.

Example 20

3-[N-(4-Bromophenyl)amino]benzoic acid (Compound 9)

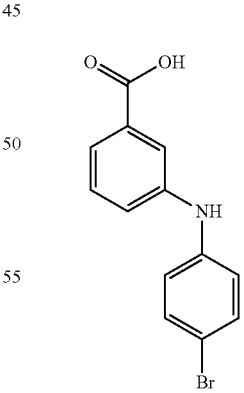

Reaction of methyl ester of Compound 9 according to general procedure B provided Compound 9 as a green solid (57% yield). $^1$H NMR (DMSO, 500 MHz): δ=12.85 (bs, 1H), 8.48 (s, 1H), 7.64 (s, 1H), 7.37-7.45 (m, 3H), 7.35 (t, J=7.8 Hz, 1H), 7.29 (d, J=8.0 Hz, 1H), 7.03 (d, J=8.9 Hz, 2H). $^{13}$C NMR (DMSO, 125 MHz): δ=167.3, 143.2, 142.3, 131.9, 131.8, 129.4, 120.9, 120.8, 118.8, 117.2, 111.0. HRMS (ES) Calcd. for $C_{13}H_{10}BrNO_2$: 289.9817 (M-H⁻). found 289.9817 (M-H⁻).

Example 21

3-[N-(4-tert-Butylphenyl)amino]benzoic acid methyl ester

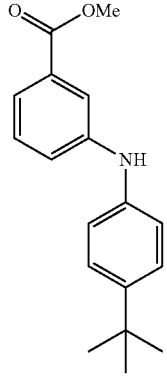 [SMILES: COC(=O)c1cccc(Nc2ccc(C(C)(C)C)cc2)c1]

Reaction of methyl 3-bromobenzoate with 4-tert-butylaniline according to general procedure A provided methyl ester of Compound 10 as a yellow oil (81% yield). ¹H NMR (CDCl₃, 500 MHz): δ=7.73 (s, 1H), 7.57 (d, J=7.6 Hz, 1H), 7.21-7.42 (m, 4H), 7.06-7.13 (m, 2H), 5.85 (s, 1H), 3.92 (s, 3H), 1.36 (s, 9H). ¹³C NMR (CDCl₃, 125 MHz): δ=167.4, 145.1, 144.3, 139.8, 131.4, 129.4, 126.4, 121.3, 120.9, 118.9, 117.7, 52.3, 34.4, 31.6.

Example 22

3-[N-(4-tert-Butylphenyl)amino]benzoic acid (Compound 10)

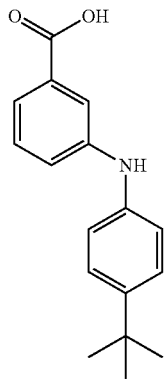 [SMILES: CC(C)(C)c1ccc(Nc2cccc(C(=O)O)c2)cc1]

Reaction of methyl ester of Compound 10 according to general procedure B provided Compound 10 as a white solid (91% yield). ¹H NMR (DMSO, 500 MHz): δ=8.17 (s, 1H), 7.62 (s, 1H), 6.95-7.40 (m, 7H), 1.26 (s, 9H). ¹³C NMR (DMSO, 125 MHz): δ=168.0, 144.1, 142.7, 140.3, 128.9, 125.8, 119.8, 118.9, 117.5, 116.2, 116.1, 33.8, 31.3. HRMS (ES) Calcd. for $C_{17}H_{19}NO_2$: 268.1338 (M-H⁻). found 268.1355 (M-H⁻).

Example 23

3-[N-(4-Methoxyphenyl)amino]benzoic acid methyl ester

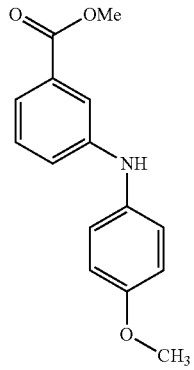 [SMILES: COC(=O)c1cccc(Nc2ccc(OC)cc2)c1]

Reaction of methyl 3-bromobenzoate with p-anisidine according to general procedure A provided methyl ester of Compound 11 as a yellow oil (93% yield). ¹H NMR (CDCl₃, 500 MHz): δ=7.57 (s, 1H), 7.50 (d, J=7.6 Hz, 1H), 7.28 (m, 1H), 7.07-7.12 (m, 3H), 6.90 (d, J=8.8 Hz, 2H), 5.62 (s, 1H), 3.90 (s, 3H), 3.83 (s, 3H). ¹³C NMR (CDCl₃, 125 MHz): δ=167.5, 156.0, 145.8, 135.2, 131.5, 129.5, 123.1, 120.7, 119.7, 116.4, 115.0, 55.8, 52.2.

Example 24

3-[N-(4-Methoxyphenyl)amino]benzoic acid (Compound 11)

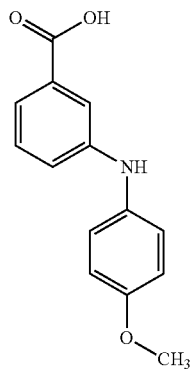 [SMILES: COc1ccc(Nc2cccc(C(=O)O)c2)cc1]

Reaction of methyl ester of Compound 11 according to general procedure B provided Compound 11 as a white solid (76% yield). ¹H NMR (DMSO, 500 MHz): δ=12.69 (bs, 1H), 8.01 (s, 1H), 7.49 (s, 1H), 7.22-7.30 (m, 2H), 7.05-7.11 (m, 3H), 6.90 (d, J=8.8 Hz, 2H), 3.73 (s, 3H). ¹³C NMR (DMSO, 125 MHz): δ=167.5, 154.4, 145.7, 135.3, 131.6, 129.2, 121.4, 118.8, 118.5, 114.7, 114.6, 55.2. HRMS (ES) Calcd. for C$_{14}$H$_{13}$NO$_3$: 242.0817 (M-H$^-$). found 242.0822 (M-H$^-$).

Example 25

3-[N-(4-Methylphenyl)amino]benzoic acid methyl ester

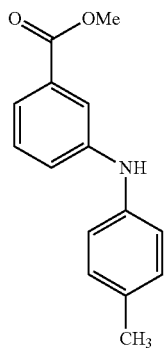 [SMILES: COC(=O)c1cccc(Nc2ccc(C)cc2)c1]

Reaction of methyl 3-bromobenzoate with p-toluidine according to general procedure A provided methyl ester of Compound 12 as a yellow oil (69% yield). $^1$H NMR (CDCl$_3$, 500 MHz): δ=7.68 (s, 1H), 7.55 (d, J=7.6 Hz, 1H), 7.29 (t, J=7.7 Hz, 1H), 7.19 (m, 1H), 7.13 (d, J=8.0 Hz, 2H), 7.03 (d, J=8.3 Hz, 2H), 5.77 (s, 1H), 3.91 (s, 3H), 2.34 (s, 3H). $^{13}$C NMR (CDCl$_3$, 125 MHz): δ=167.4, 144.6, 139.8, 131.9, 131.5, 130.2, 129.5, 121.3, 120.8, 119.7, 117.5, 52.2, 20.9.

Example 26

3-[N-(4-Methylphenyl)amino]benzoic acid (Compound 12)

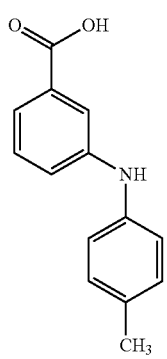 [SMILES: Cc1ccc(Nc2cccc(C(=O)O)c2)cc1]

Reaction of methyl ester of Compound 12 according to general procedure B provided Compound 12 as a white solid (70% yield). $^1$H NMR (DMSO, 360 MHz): δ=8.17 (s, 1H), 7.58 (s, 1H), 7.16-7.36 (m, 3H), 7.08 (d, J=8.2 Hz, 2H), 7.00 (d, J=8.0 Hz, 2H), 2.24 (s, 3H). $^{13}$C NMR (DMSO, 90 MHz): δ=167.5, 144.6, 140.0, 131.7, 129.6, 129.2, 119.5, 119.4, 118.4, 115.8, 20.5. HRMS (ES) Calcd. for C$_{14}$H$_{13}$NO$_2$: 226.0868 (M-H$^-$). found 226.0861 (M-H$^-$).

Example 27

General Procedure B: Synthetic Scheme for (Napthalenylamino)Benzoic Acids

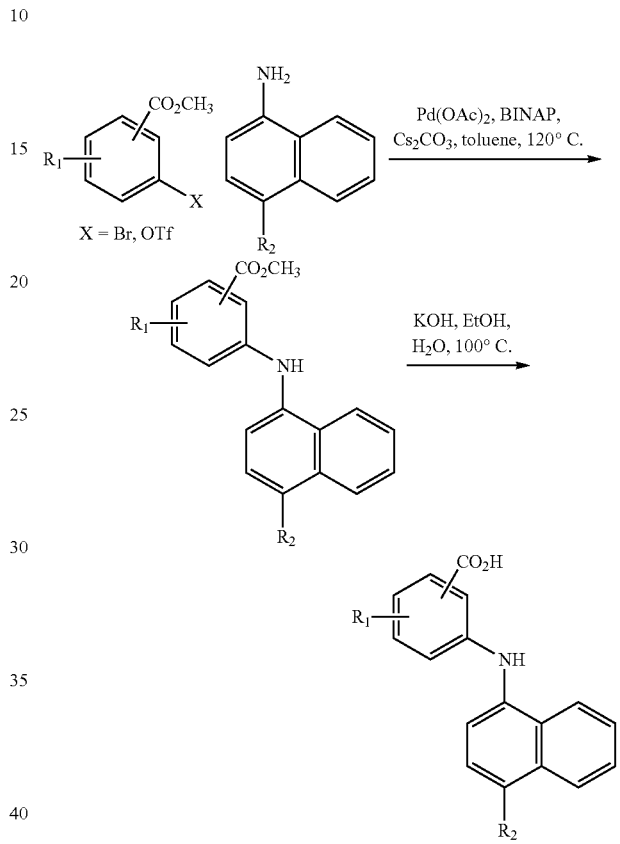

Example 28

Synthesis and physicochemical characterization of 3-((4-nitronaphthalen-1-yl)amino)benzoic acid (Compound 13)

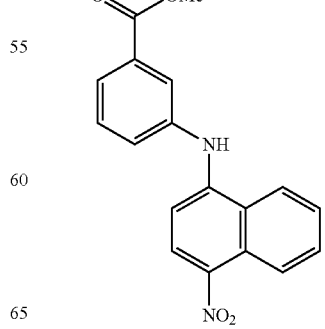

(3-((4-nitronaphthalen-1-yl)amino)benzoic acid methyl ester

4-Nitro-1-naphthylamine (1.2 equiv), $Cs_2CO_3$ (1.4 equiv), BINAP (0.08 equiv), and $Pd(OAc)_2$ (0.05 equiv) were added to a solution of methyl 3-bromobenzoate (1 equiv) in toluene (0.1 M) at 25° C. The reaction mixture was allowed to stir at 120° C. for 48 h. Once the reaction appeared to be complete by consumption of the bromide (or triflate) by TLC analysis, the mixture was allowed to cool to 25° C., diluted with EtOAc, washed with 2 M aq HCl (2x), brine, and dried over sodium sulfate. The solution was concentrated, loaded on silica gel, and purified by silica gel chromatography to give the methyl ester of compound 13 as an orange solid (22% yield). $^1$H NMR (CDCl$_3$, 500 MHz): δ=8.94 (d, J=8.8 Hz, 1H), 8.35 (d, J=8.7 Hz, 1H), 8.08 (d, J=8.4 Hz, 1H), 7.95 (s, 1H), 7.86 (d, J=7.2 Hz, 1H), 7.78 (t, J=7.8 Hz, 1H), 7.64 (t, J=7.7 Hz, 1H), 7.45-7.54 (m, 2H), 7.15 (d, J=8.7 Hz, 1H), 6.75 (s, 1H), 3.94 (s, 3H). $^{13}$C NMR (CDCl$_3$, 125 MHz): δ=166.7, 146.3, 141.0, 138.9, 132.2, 130.2, 130.1, 127.8, 127.7, 127.0, 126.3, 125.7, 125.0, 124.6, 123.1, 120.9, 107.3, 52.6. HRMS (ES) Calcd. for $C_{18}H_{14}N_2O_4$: 321.0875 (M-H$^-$). found 321.0872 (M-H$^-$).

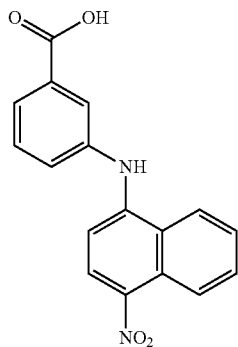 [SMILES: O=C(O)c1cccc(Nc2ccc([N+](=O)[O-])c3ccccc23)c1]

3-((4-nitronaphthalen-1-yl)amino)benzoic acid

KOH (2 equiv) in water (0.2 M) was added to the purified methyl ester of compound 2 (1 equiv) in EtOH (0.2 M) at 25° C. The reaction mixture was stirred at 100° C. for 6 h and monitored by TLC analysis. EtOH was evaporated from the reaction mixture upon completion; the resultant solution was cooled to 0° C. and acidified to pH 2 with 2 M aq HCl. The product crystallized out of the aqueous medium upon acidification allowing the product (orange solid, 83% yield) to be collected by a simple vacuum filtration. $^1$H NMR (DMSO, 500 MHz): =13.00 (bs, 1H), 9.45 (s, 1H), 8.79 (d, J=8.6 Hz, 1H), 8.53 (d, J=8.3 Hz, 1H), 8.38 (d, J=8.9 Hz, 1H), 7.93 (s, 1H), 7.84 (m, 1H), 7.68-7.76 (m, 2H), 7.63 (m, 1H), 7.55 (m, 1H), 7.13 (d, J=8.8 Hz, 1H). $^{13}$C NMR (DMSO, 125 MHz): δ=166.9, 147.7, 141.0, 136.1, 132.1, 130.2, 129.8, 128.5, 127.0, 126.3, 126.1, 124.6, 123.7, 123.3, 123.2, 122.8, 105.9. HRMS (ES) Calcd. for $C_{17}H_{12}N_2O_4$: 307.0719 (M-H$^-$). found 307.0709 (M-H$^-$).

Example 29

Design and Evaluation of Compounds

Non-steroidal anti-inflammatory drugs (NSAIDs), such as those based on N-phenylanthranilic acids (N-PA) in particular, are known to be inhibitors of the AKR1C enzymes (Bauman et al., 2005, Mol. Pharmacol. 67:60). Developing N-PA based AKR1C3 inhibitors that are devoid of cyclooxygenase (COX) or other AKR1C enzyme inhibitory activity is desirable since much is known about the absorption, distribution, metabolism, excretion and toxicity (ADMET) of this class of drugs.

Based on known structure-activity relationships for COX isozymes, substitution on the A-ring of an N-PA, or movement of the carboxylic acid from the ortho-position should eliminate COX inhibition. Furthermore, the X-ray crystal structure of the AKR1C3-NADP$^+$-flufenamic acid complex (PDB ID: 1S2C) provides insights on how the prototypical N-PA, flufenamic acid is bound. Its carboxylic acid group is anchored via hydrogen bond interaction at the oxyanion hole of the active site, which is formed by the cofactor and catalytic tetrad. The secondary amine of the drug also forms hydrogen bond interactions with the carboxamide oxygen of the nicotinamide ring of the cofactor, while the B-ring containing the meta-trifluoromethyl group substituent is bound in a distinct sub-pocket. Analysis of this sub-pocket in AKR1C3 showed that it was larger, different in shape and lined by polar amino acids (S118, S308 and Y319) relative to either AKR1C1 or AKR1C2, where the corresponding residues are F118, L308, and F319. This suggested that appropriate substitution on the B-ring may provide the needed AKR1C3 selectivity.

The effect of the movement of the carboxylic acid on the A-ring of an N-PA was systematically examined, and the effect of substituents on the B-ring was concurrently measured. This led to a series of 3-(phenylamino)benzoic acid derivatives that are potent and selective inhibitors for AKR1C3 over AKR1C1 and AKR1C2 (FIGS. 7 and 8).

Figure 7:
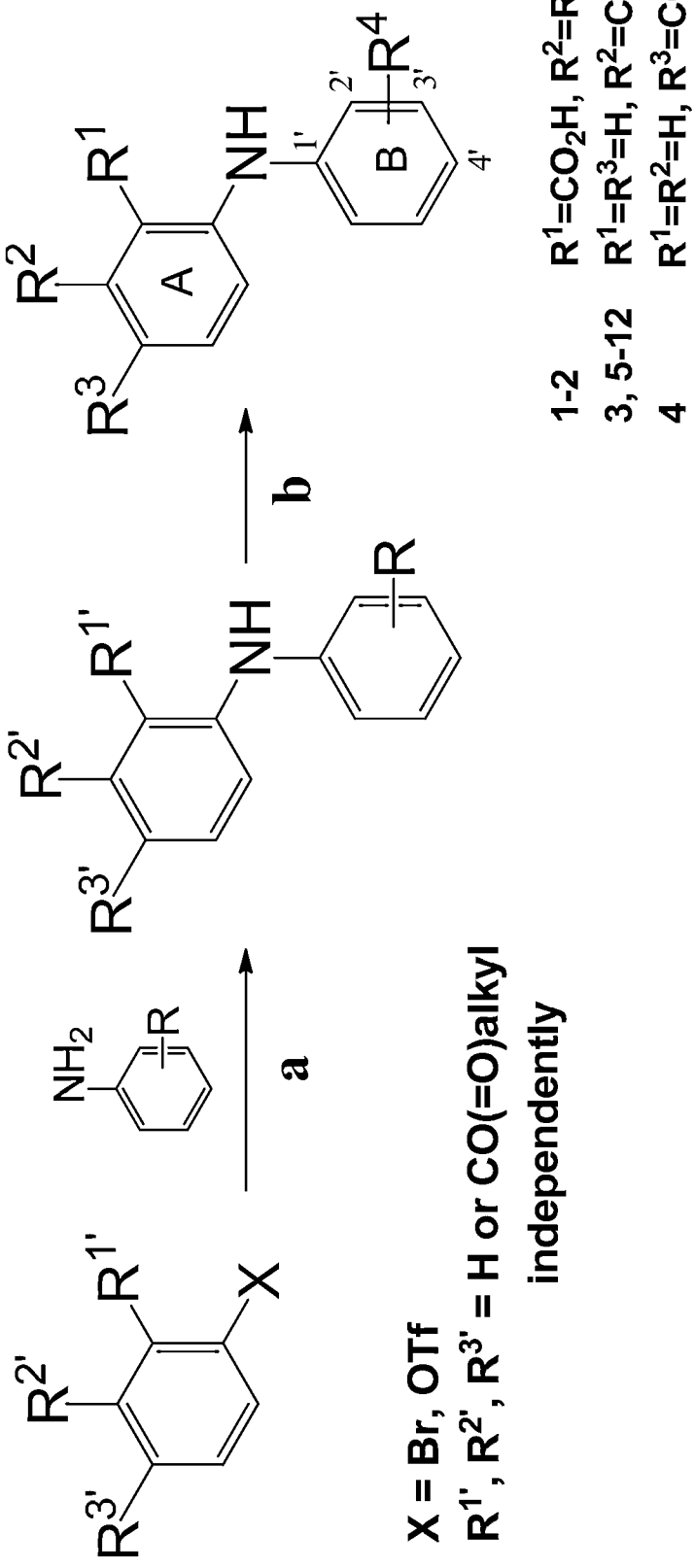
FIG. 7 illustrates the synthetic scheme for 2-, 3-, and 4-(phenylamino)benzoic acid analogs, Compounds 1-12 (see FIGS. 8A-8B). Reaction conditions: (a) Pd(OAc)$_2$, 2,2'-bis(diphenylphosphino)-1,1'-binaphthyl (BINAP), Cs$_2$CO$_3$, toluene, 120° C.; (b) KOH, EtOH, H$_2$O, 100° C.

Compounds were synthesized according to the scheme in FIG. 7. The reaction involved a Buchwald-Hartwig C—N coupling followed by methyl ester saponification. In most cases, the product crystallized out of the aqueous medium upon acidification allowing the product to be collected by a simple vacuum filtration. Compounds were characterized by NMR analysis and high resolution mass spectrometry.

AKR1C1 and AKR1C2 share 98% sequence identity and differ in only one amino acid at their respective active sites (Burczynski et al., 1998, Biochemistry 37:6781; Jin et al., 2001, Biochemistry 40:10161). It is therefore likely that an inhibitor of AKR1C2 also inhibits AKR1C1. Based on this assumption, the screening strategy adopted was to determine the inhibitory potency of each compound against AKR1C2 and AKR1C3 and use the ratio of IC$_{50}$ value for AKR1C2:IC$_{50}$ value for AKR1C3 as an index of compound selectivity for AKR1C3. The inhibitory potency of compounds on AKR1C2 and AKR1C3 was determined by measuring the inhibition of the NADP$^+$ dependent oxidation of S-tetralol. All assays were performed at the K$_M$ of the respective AKR1C isoforms, so that IC$_{50}$ values were directly comparable.

The lead compound was the prototypic N-PA, flufenamic acid (o-CO$_2$H, 3'-CF$_3$) or Compound 1, which gave an IC$_{50}$ value of 50 nM for AKR1C3 and showed a modest seven-fold selectivity for the inhibition of AKR1C3 over AKR1C2 (FIG. 8). Compounds 2-4 were synthesized to evaluate the effect of changing the position of the carboxylic acid group on the A-ring on the inhibitory potency and selectivity for AKR1C3. The B-ring unsubstituted compounds were initially selected to preclude substituent effects. Movement of the CO$_2$H group had no remarkable effect on the inhibitory potency for AKR1C3, thus, ortho-, meta- and para-carboxylate gave IC$_{50}$ values of 1.5 µM, 0.94 µM and 2.8 µM for Compounds 2, 3, and 4, respectively. These compounds offered two important clues to further inhibitor development. First, Compound 3 showed a 14-fold selectivity for the inhibition of AKR1C3 over AKR1C2, indicating a 48-fold increase in AKR1C3 selectivity with movement of the carboxylic acid from o- to m-position (compare $IC_{50}$ value ratios for compounds 2 and 3), suggesting that the m-$CO_2H$ may be important for selectivity. Second, Compound 2, the B-ring unsubstituted analog of Compound 1 was 30-fold less potent as an AKR1C3 inhibitor than 1, suggesting that B-ring substitution was important for potency. This loss of potency is expected given the greater distance and consequently, reduced interactions between the B-ring and the sub-pocket in the absence of a substituent on the B-ring. Using compound 3 as the new lead (m-$CO_2H$ on the A-ring), eight B-ring para substituted analogs of Compound 3 (Compounds 5-12) were synthesized and evaluated to assess the effects of different substituents on AKR1C3 potency and selectivity. The p-substituents were selected since they should project furthest into the sub-pocket, increasing the potential for interaction with the relevant amino acid residues.

As illustrated in FIG. 8, the lowest $IC_{50}$ values for AKR1C3 inhibition were obtained with an electron withdrawing group (EWG) as the B-ring substituent, such as Compound 5 (p-$NO_2$) which gave a value of 36 nM. Compound 6 (p-Ac) and Compound 7 (p-CF3) were the two most selective inhibitors and gave $IC_{50}$ values that were 360 and 250-fold selective for AKR1C3 over AKR1C2, respectively. However, all the B-ring para substituted analogs (both EWG and EDG) exhibited significantly better inhibitory potency for AKR1C3 and were also more selective for AKR1C3 relative to AKR1C2 than the parent Compound 3. Interestingly, analogs with EWG, that is, Compounds 5-9, displayed relatively similar AKR1C3 inhibitory potency with flufenamic acid, Compound 1, while those with electron donating substituents (EDG), Compounds 10-12 displayed weaker AKR1C3 inhibitory activity than 1. In contrast, all B-ring para-substituted compounds bearing an A-ring m-$CO_2H$ display significantly higher $IC_{50}$ values than flufenamic acid for AKR1C2, regardless of the electronic properties of the substituent. The increase in $IC_{50}$ values for AKR1C2 due to the presence of the m-$CO_2H$ group results in increased AKR1C3 selectivity.

Figure 9:
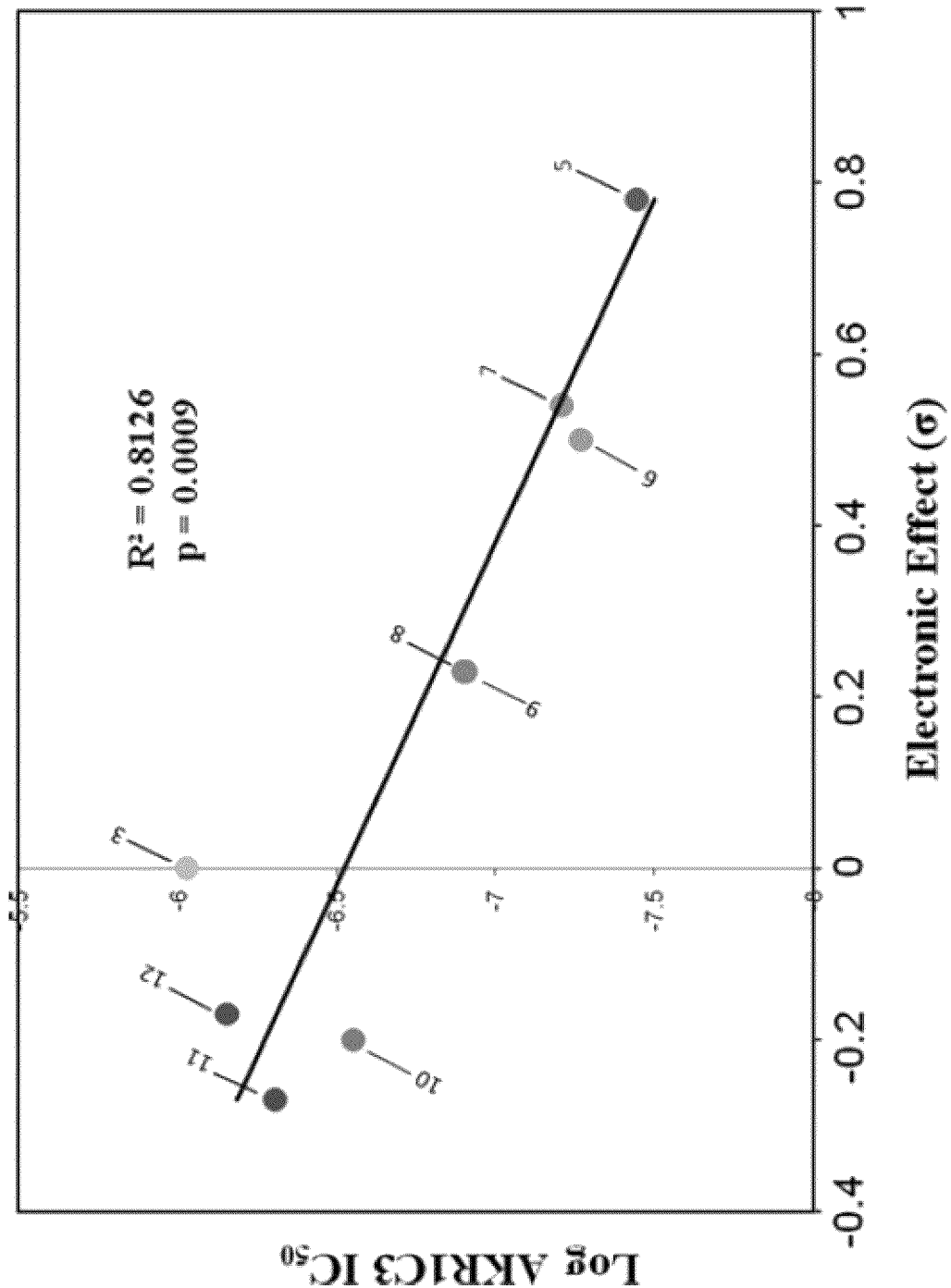
FIG. 9 is a graph illustrating the correlation of AKR1C3 inhibitory potency and electronic effect (r) of substituents.

A regression analysis of the electronic effect of the varied substituent at the para-position and the inhibitory potency for AKR1C2 and AKR1C3 was then performed. The plot (as illustrated in FIG. 9) revealed a significant correlation between the electronic effect and AKR1C3 potency for the para-substituted 3-(phenylamino)benzoic acid analogs ($R^2$=0.81, p=0.0009). However, no significant correlation between the electronic effect and inhibitory potency for AKR1C2 ($R^2$=0.37, p=0.084) was noted for these compounds. Further analysis showed there was also a significant correlation between the AKR1C3 potency and the calculated $pK_a$ of the carboxylic acid group ($R^2$=0.80, p=0.0012) and the $pK_a$ of the secondary amine ($R^2$=0.79, p=0.0014), both of which are related to the electronic effect of the B ring substituents. The data on the electronic effects seen with the AKR1C3 inhibitors is consistent with these compounds forming hydrogen bonds with AKR1C3 at the active site. EWG or EDG on the B-ring that alter the acidity of the carboxylic acid and basicity of the secondary amine group in particular would be expected to affect the inhibitory potency of the compounds. The electronic effect observed for AKR1C3 inhibition could also be as a result of discrete interactions between residues lining the sub-pocket and the B-ring substituents.

Hydrogen bond formation at the active site is also expected in AKR1C2 but the lack of correlation between inhibitory potency and the electronic effect suggests other factors might be more relevant for inhibitor binding. Most of the B-ring substituted compounds have relatively similar inhibitory potency on AKR1C2 and gave $IC_{50}$ values which were in the low micromolar range, it is likely that with A-ring m-$CO_2H$ analogs, the B-ring is precluded from binding in the expected sub-pocket in this isoform, presumably as a result of the smaller size of this pocket. In one aspect, it may be likely that the B-ring of these inhibitors is forced to occupy the larger vacant steroid binding site in AKR1C2. Further X-ray crystallographic studies may determine the precise mechanism by which these compounds interact with the two enzymes and account for the selectivity seen with m-COOH analogs.

Several AKR1C3 inhibitors of varied structural classes have been reported in the literature. However, selectivity for AKR1C3 over AKR1C1-2 is often low or not indicated. The 3-(phenylamino)benzoic acid analogs disclosed herein are potent inhibitors of AKR1C3 with orders of magnitude selectivity for AKR1C3. These compounds highlight structural modifications on N-PA that are essential for AKR1C3 inhibition and confer selectivity over AKR1C1 and AKR1C2. In one aspect, a meta arrangement of the carboxylic acid and secondary amine moieties, as well as a strong electron withdrawing group at the para position of the B-ring, confers selectivity for AKR1C3 over AKR1C2. Without wishing to be limited by theory, the selective inhibition of AKR1C3 conferred by the presence of the meta-carboxylic acid group and an electron-withdrawing group on the para-position of the B-ring may be explained by the x-ray crystal structure of the AKR1C3.NADP+. 3-[N-4-trifluoromethylphenyl)amino] benzoic acid complex (PDB: 4DBU) (FIG. 26). FIG. 26 suggests that the carboxylic acid is anchored at the oxyanion as anticipated, but as a consequence the change in the position of the bridge amine from the ortho- to the meta-position allows the B-ring with its electron withdrawing group to penetrate more deeply into the SP-1 pocket (Chen et al., 2012, Bioorg. Med. Chem. Lett., in press).

N-PA are known to be competitive inhibitors of AKR1C3. The compounds in this disclosure were also found to inhibit AKR1C3 in a competitive manner (data not shown). Also, they are predicted to have little or no inhibitory activity on COX enzymes since the ortho arrangement of the —$CO_2H$ and —$NH_2$ on the A-ring has been shown to be critical for COX activity (Lombardino, Nonsteroidal Antiinflammatory Drugs; Wiley Interscience: New York, N.Y., 1985; Scherrer, Antiinflammatory Agents: Chemistry and Pharmacology; Academic Press: New York, N.Y., 1974; Selinsky et al., 2001, Biochemistry 40:5172).

The success of abiraterone acetate, in clinical trials for management of CRPC makes the discovery of these AKR1C3 selective inhibitors promising. Because of the position of AKR1C3 in the androgen biosynthetic pathway in the prostate, these compounds are likely to be more specific and have less undesirable side effects as seen with CYP17 inhibitors.

The inhibitors disclose herein have nanomolar potency for AKR1C3 and significant selectivity for AKR1C3 over other AKR1C enzymes. They may be used as probes to elucidate the role of AKR1C3 in cell culture models. More importantly, these compounds may serve as useful therapeutic leads in the treatment and/or prevention of CRPC as well as other androgen/estrogen dependent malignancies.

Example 30

Screening Strategy

Figure 1:
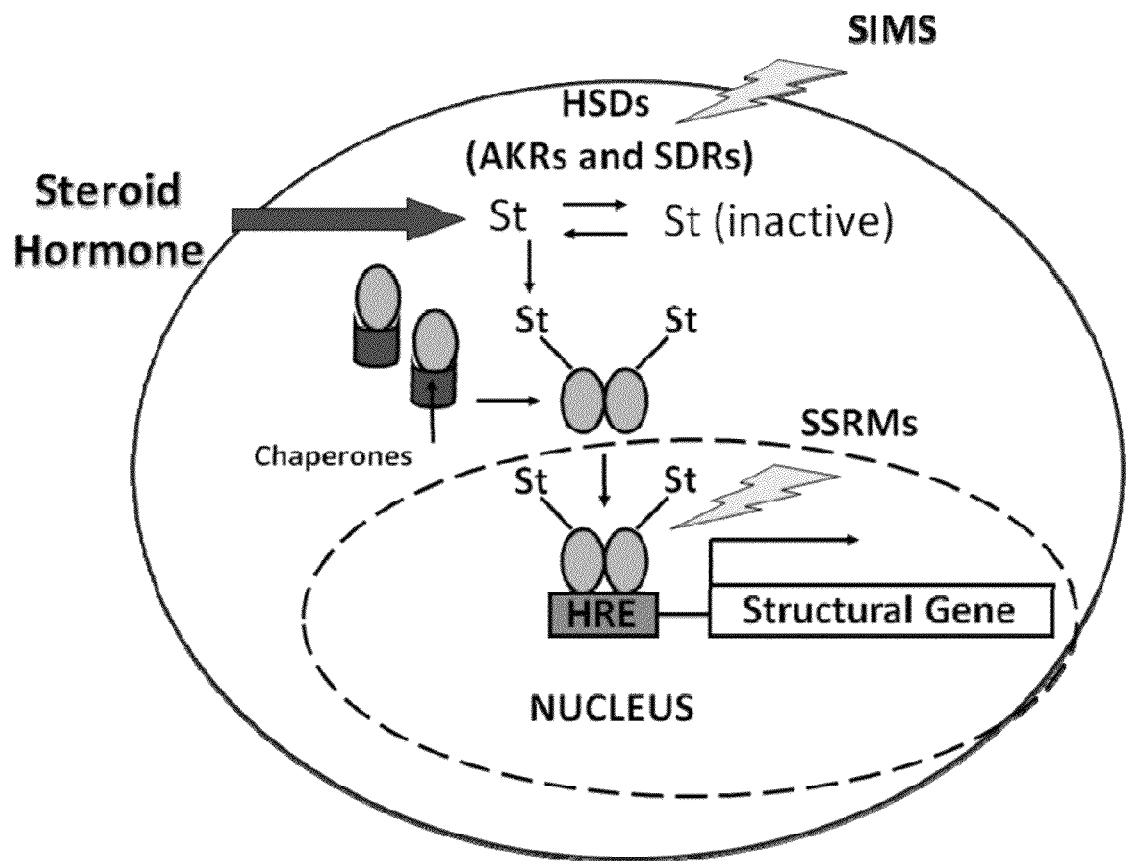
FIG. 1 illustrates the pre-receptor regulation of nuclear receptors by HSDs (hydroxysteroid dehydrogenases). In target tissues levels of steroid hormones are regulated by HSDs prior to binding to their cognate receptors. Sites of SIM (selective intracrine modulators) and SSRM (selective steroid receptor modulators) action are illustrated.
Figure 3:
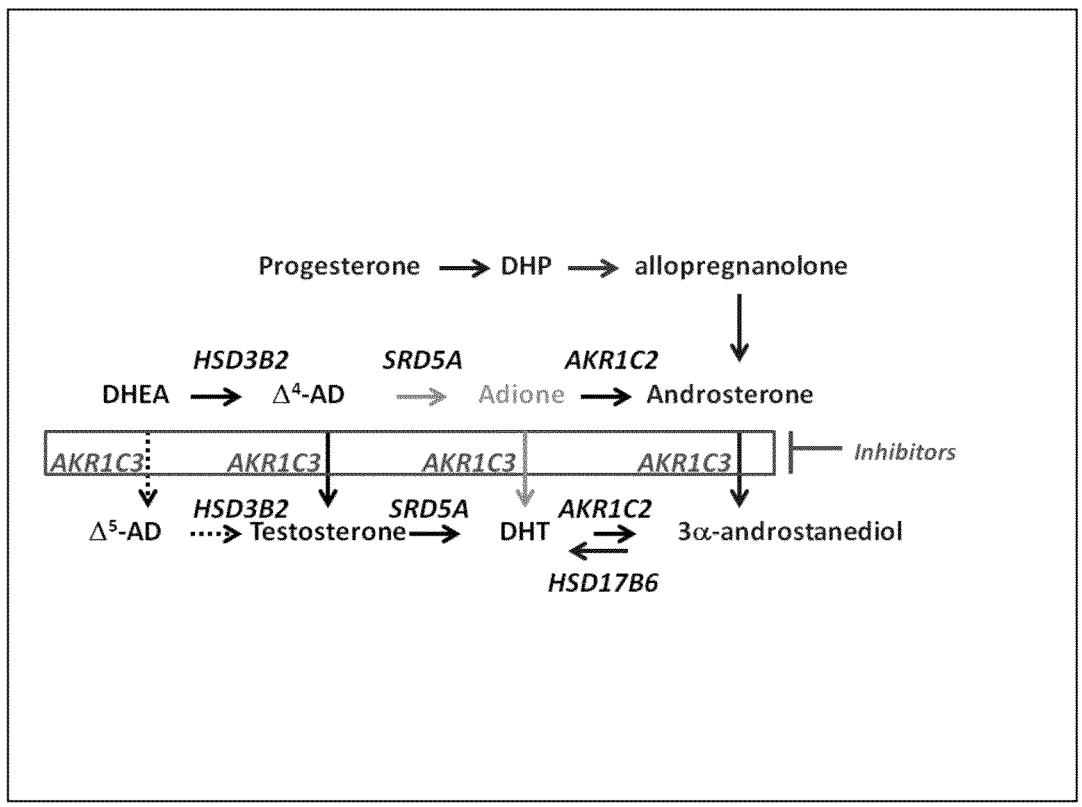
FIG. 3 illustrates the central role that AKR1C3 plays in the formation of testosterone and 5α-DHT (DHT) in the prostate. All three pathways to DHT proceed through AKR1C3, the classical pathway (black); the alternative pathway in (green); and the backdoor pathway (blue). DHE=dehydroepiandrosterone; $\Delta^4$-AD=$\Delta^4$-androstene-3,17-dione; Adione=5α-androstane-3,17-dione; DHP=5α-dihydroprogesterone; HSD3B2=3β-hydroxysteroid dehydrogenase/ketosteroid isomerase type 2; SRD5A=steroid 5α-reductase types 1 &2; HSD17B6=17b-hydroxysteroid dehydrogenase type 6.
Figure 5:
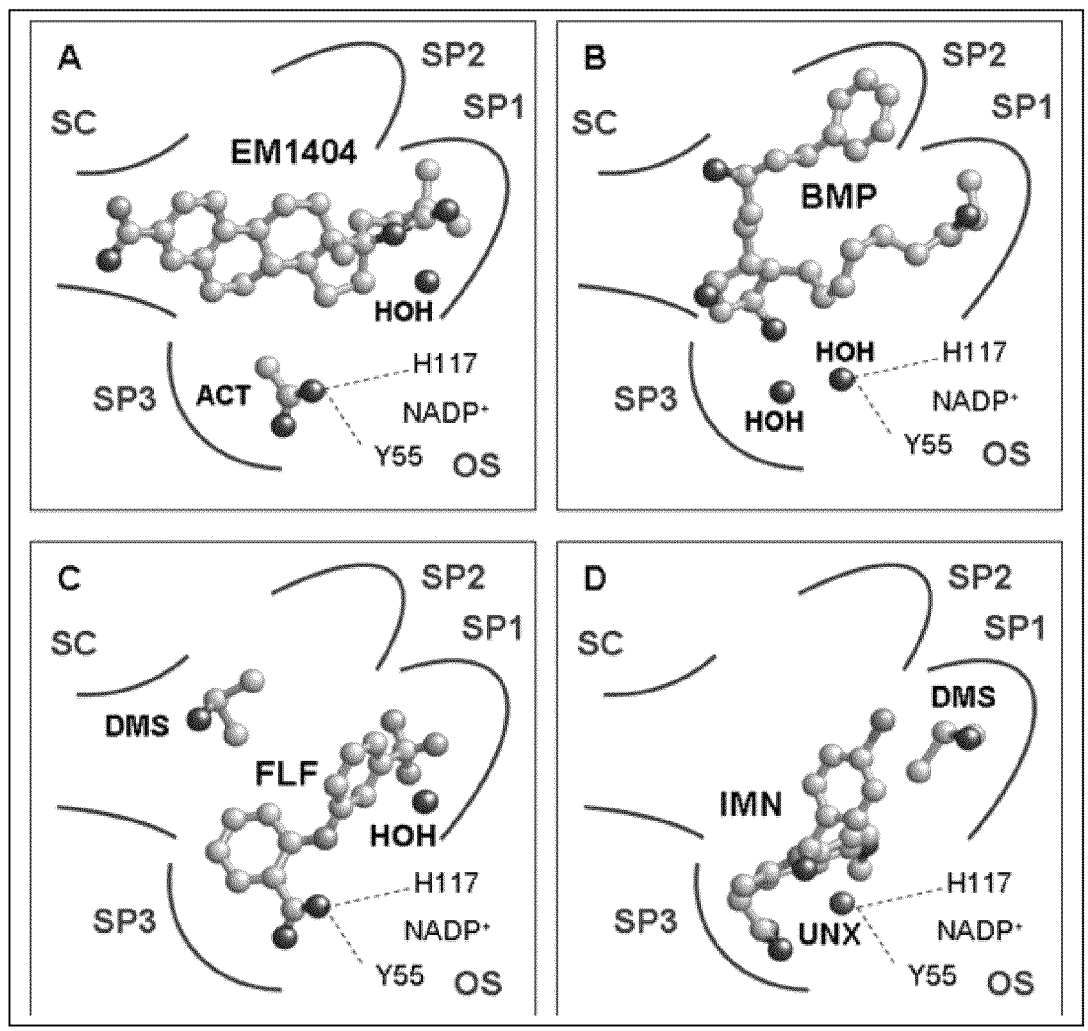
FIG. 5, comprising
Figure 6:
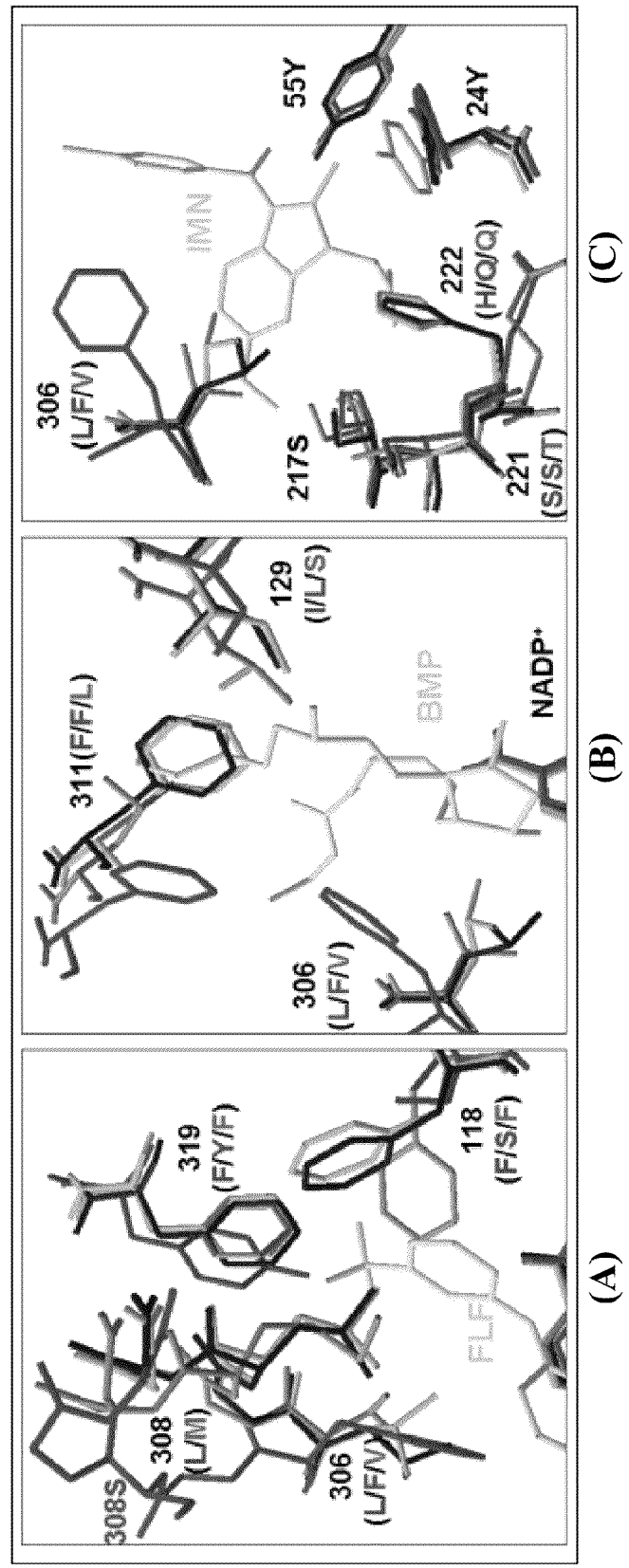
FIG. 6, comprising
Figure 16:
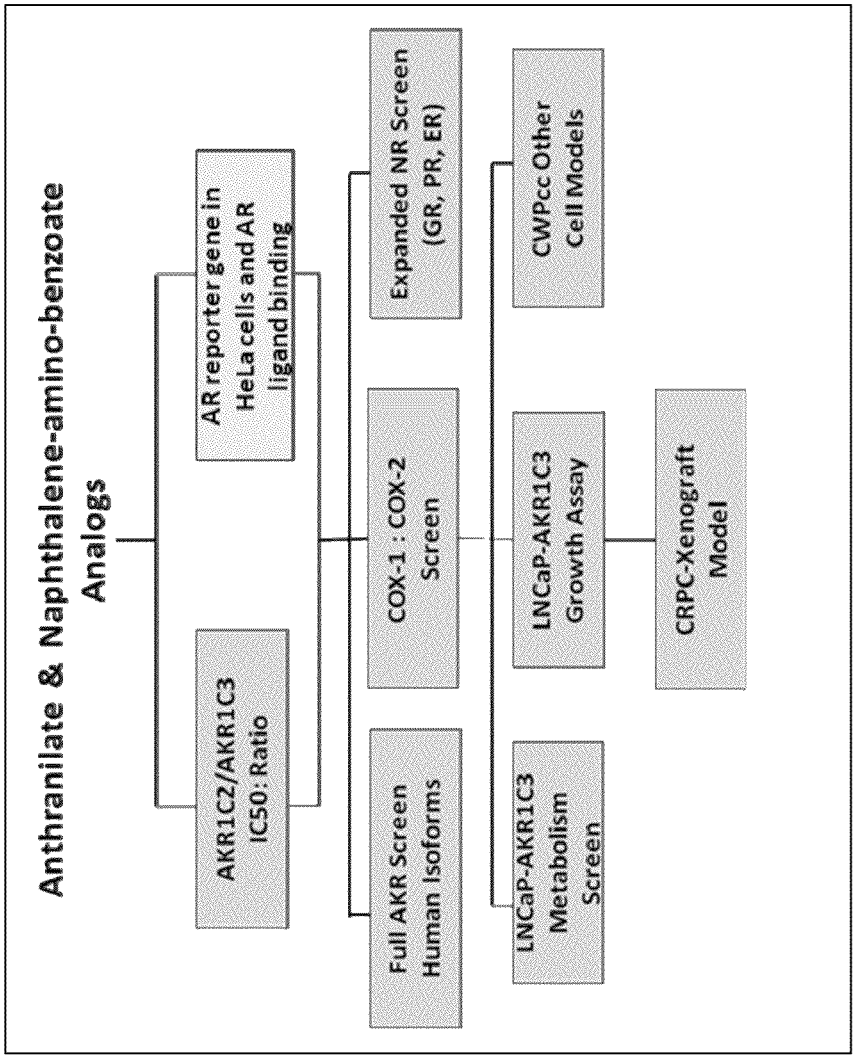
FIG. 16 is a scheme illustrating the screening strategy disclosed herein.
Figure 19:
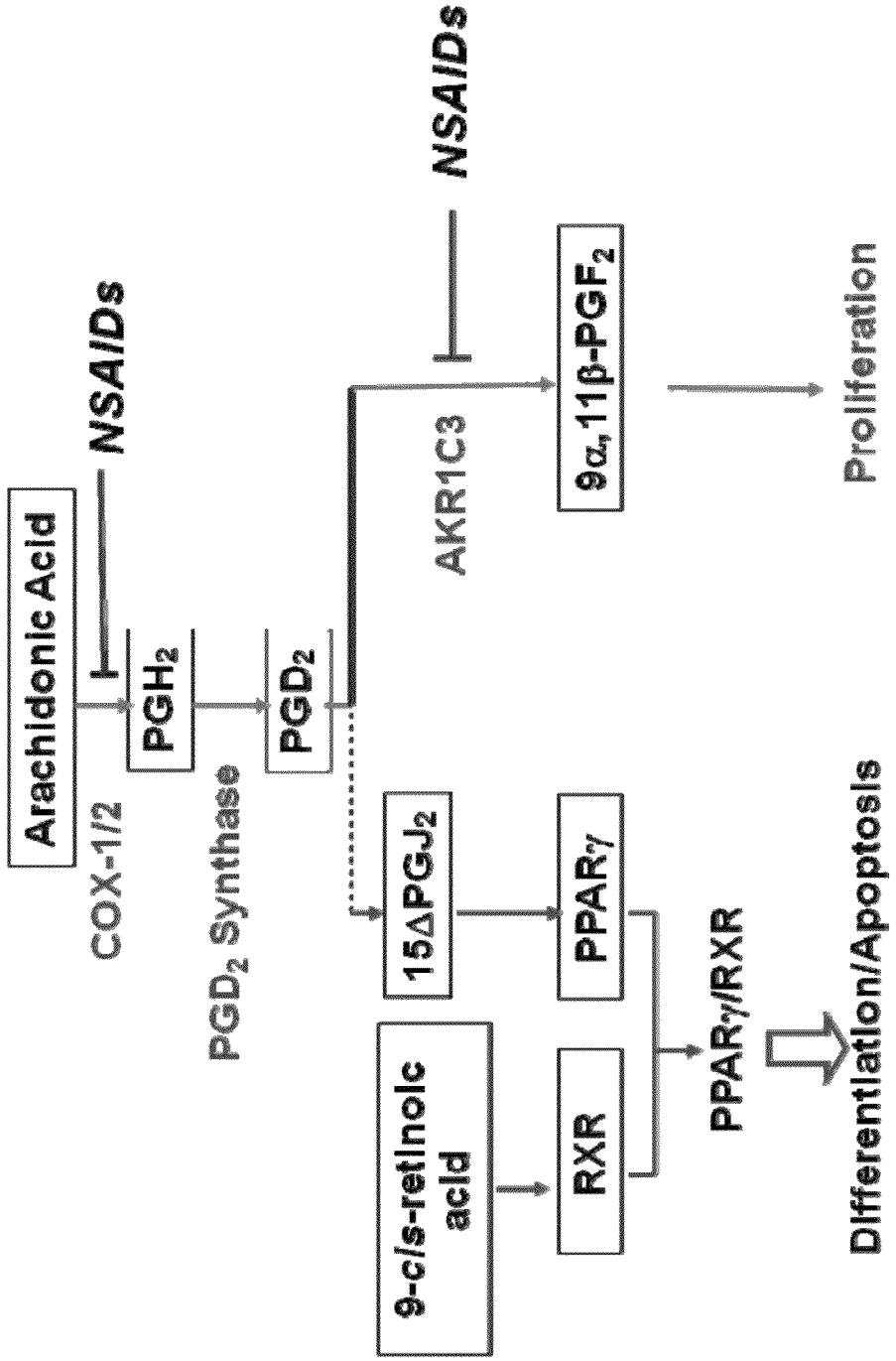
FIG. 19 is a flux diagram illustrating AKR1C3 and regulation of PPARγ.
Figure 20:
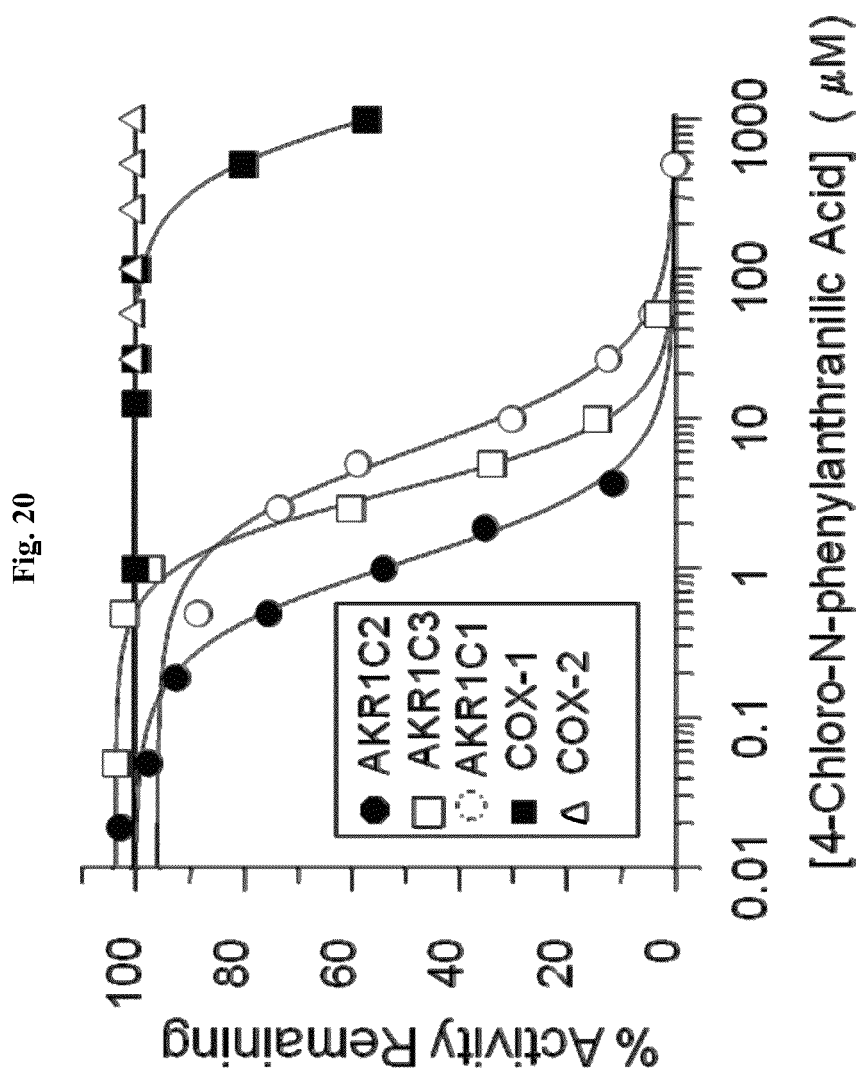
FIG. 20 is a set of graphs illustrating the finding that 4-chloro-N-phenylanthranilate inhibits AKR1C enzymes but not COX-1 or COX-2.
Figure 21:
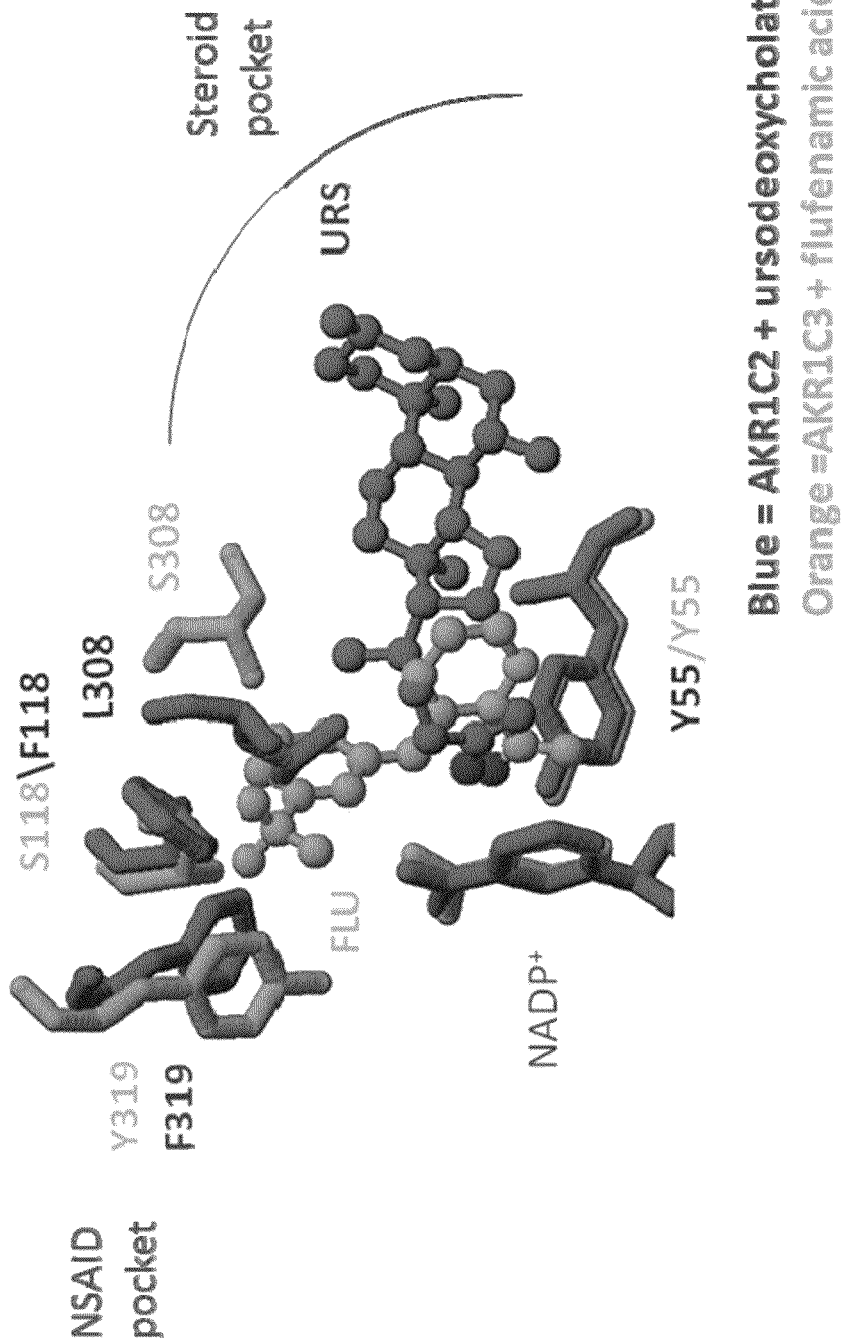
FIG. 21 is a figure illustrating the structural basis of inhibitor selectivity for AKR1C isoforms. The positions of ursodeoxycholate (URS) in AKR1C2 and flufenamic acid in AKR1C3 are illustrated.
Figure 22:
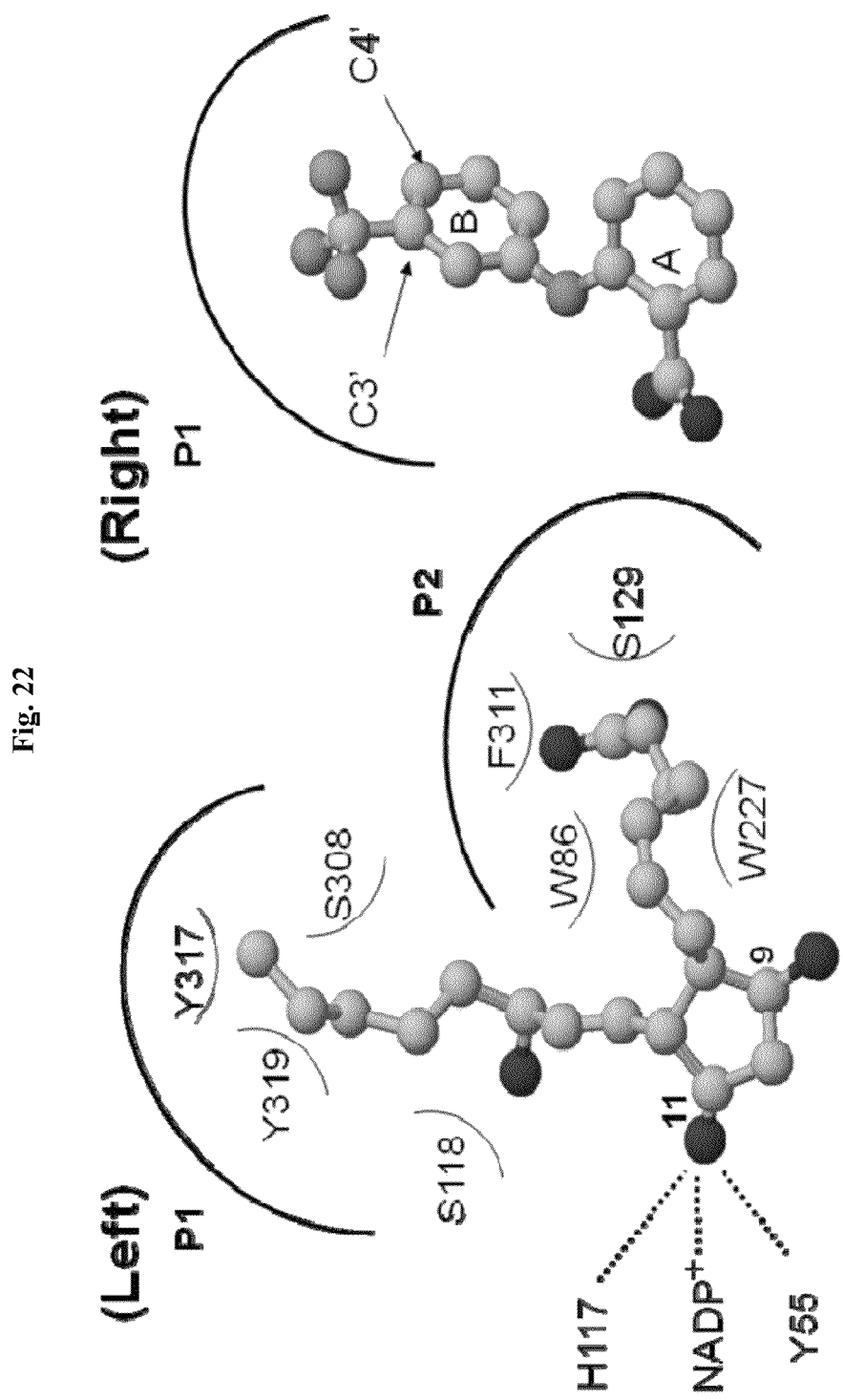
FIG. 22 is a figure illustrating the rational design of AKR1C3 inhibitors. On the left: RASMOL display of the binding of PGD$_2$ into the SP1 and SP2 pockets of the AKR1C3 active site. On the right: RASMOL display of the orientation of flufenamic acid in the SP1 pocket.

The screening strategy for monofunctional agents (AKR1C3 inhibitors) and bifunctional agents (AKR1C3 inhibitors and AR modulators) disclosed herein is illustrated in FIG. 16. The primary screen was against homogeneous recombinant AKR1C3 and the AR. AKR1C3 was screened against its highly related enzyme AKR1C2 to generate full dose-response curves and $IC_{50}$ values. Inhibitors of AKR1C2 are also likely to inhibit AKR1C1, since these two enzymes differ by only one amino acid at the active site. Inhibitors of AKR1C1 and AKR1C2 are undesirable in the context of prostate cancer (FIG. 1). AKR1C1 converts 5α-dihydrotestosterone (5α-DHT: a potent androgen) to 3β-androstanediol (a pro-apoptotic ligand for estrogen receptor β) and AKR1C2 converts 5α-DHT to 3α-androstanediol (a weak androgen). Inhibition of either AKR1C1 or AKR1C2 in the prostate would be predicted to promote proliferation.

Compounds 5-10 showed 100- to 1000 fold selectivity for the inhibition of AKR1C3 over the related AKR1C1, AKR1C2 and AKR1C4 isoforms (FIG. 30). Compound 13 (3-((4-nitronaphthalen-1-yl)amino)benzoic acid) showed an $IC_{50}$ value of 75 nM for AKR1C3, and shows 147-fold, 156-fold, and 109-fold selectivity for inhibition of AKR1C3 over AKR1C1, AKR1C2, and AKR1C4, respectively, FIG. 23. As compound 13 is no longer a N-phenylaminobenzoate its inhibition pattern was shown to be competitive against S-tetralol and $Δ^4$-androstene-3,17-dione, FIG. 24A, B; its selectivity to inhibit steroid transformation catalyzed by AKR1C3 versus AKR1C2 was also confirmed, FIG. 25. A primary screen was also performed against the AR using a HeLa-cell AR-reporter gene assay. Compound 13 also acted as an AR antagonist in the AR reporter gene assay with an $IC_{50}$ value of 4.9 μM and 11.1 μM in the presence of 0.1 nM 5α-DHT and 0.5 nM R1881, respectively, FIG. 27A, B.

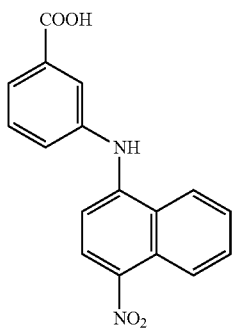 [SMILES: O=C(O)c1cccc(Nc2ccc([N+](=O)[O-])c3ccccc23)c1]

Compound 13

Bicalutamide, the major AR receptor antagonist in clinical use for prostate cancer, had an $IC_{50}$ value of 430 nM, and MDV3100 a second generation AR receptor antagonist had an $IC_{50}$ value of 660 nM in the same competitive binding assay using [3H]-R1881 as ligand, FIG. 28. Thus, Compound 13 and its congeners are expected to define AR antagonists with similar potency to current therapeutics.

Secondary Screens

Secondary screens of the compounds of interest include: (a) a full-screen against all nine human recombinant AKR enzymes to ensure there are no-intended off-target effects (in this context AKR1B10 (retinal reductase; SEQ ID NO:5) has been shown to be potently inhibited by N-phenylanthranilates) (Endo et al., 2010, Biol. Pharm. Bull. 33:886-90); (b) a screen against COX-1 and COX-2 to reaffirm that compounds do not act as NSAIDs; and (c) an expanded screen against other nuclear receptors (especially other steroid hormone receptors). Compounds 5-10 and 13 failed to inhibit aldose reductase (AKR1B1), retinal reductase (AKR1B10) or COX-1 or COX-2 (FIGS. 30 and 31).

Tertiary Screens

Tertiary screens of the compounds of interest include: (a) inhibition of the conversion of $Δ^4$-AD to testosterone in LNCaP (AR dependent prostate cancer) cells stably transfected with AKR1C3; (b) inhibition of $Δ^4$-AD mediated cell proliferation in LNCaP cells stably transfected with AKR1C3; and (c) inhibition of growth of castrate resistant prostate cancer cells in culture. Compounds 8 and 13 completely blocked the conversion of $Δ^4$-AD to testosterone in LNCaP-AKR1C3 transfected cells at concentrations of 10 μM (FIG. 26).

Additional Tertiary Screens

Figure 32:
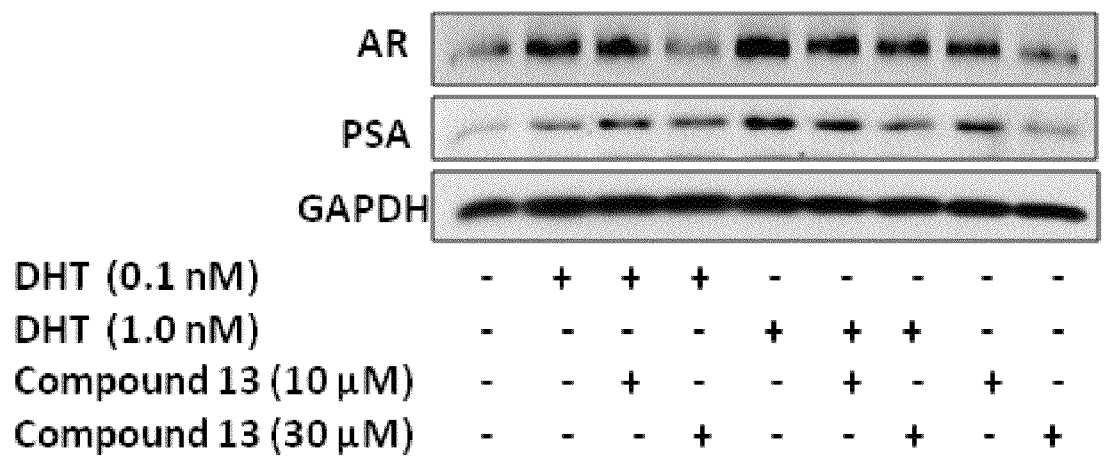
FIG. 32 is the detail of a gel illustrating the ability of the bifunctional agent (compound 13) to inhibit the expression of the androgen regulated gene, prostatic specific antigen in LNCaP cells following treatment with 5α-DHT. AR=androgen receptor, PSA=prostatic specific actigen, GAPDH=glyceraldehyde-3-phosphate dehydrogenase.

The ability of lead compounds to block AR regulated prostatic specific antigen (PSA) gene expression in LNCaP cells was also examined Compound 13 (10-30 μM) was shown to block the expression of PSA in the presence and absence of 5α-DHT (0.1-1.0 nM) (FIG. 32).

Figure 33:
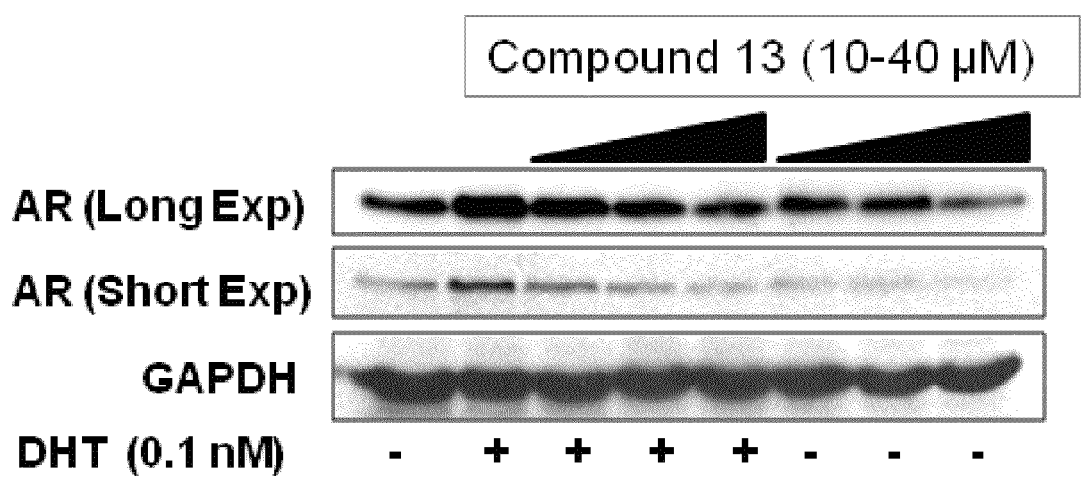
FIG. 33 is the detail of a gel illustrating the ability of the bifunctional agent (compound 13) to degrade the androgen receptor in the presence and absence of 5α-DHT. AR=androgen receptor, GAPDH=glyceraldehyde-3-phosphate dehydrogenase.

The ability of lead compounds to decrease the stability of the AR was also examined Compound 13 (10-40 μM) caused a dose-dependent degradation of the AR in the presence and absence of 0.1 nM 5α-DHT in Hela cells (FIG. 33).

The ability of lead compounds to reduce levels of the mutated AR and PSA expression in the presence of the AR ligand 5α-DHT and the AKR1C3 substrate $Δ^4$-AD was also examined Compound 13 caused a decrease in the expression the mutated AR and PSA in the presence of either 1.0 nM 5α-DHT or 100 nM $Δ^4$-AD.

Figure 35:
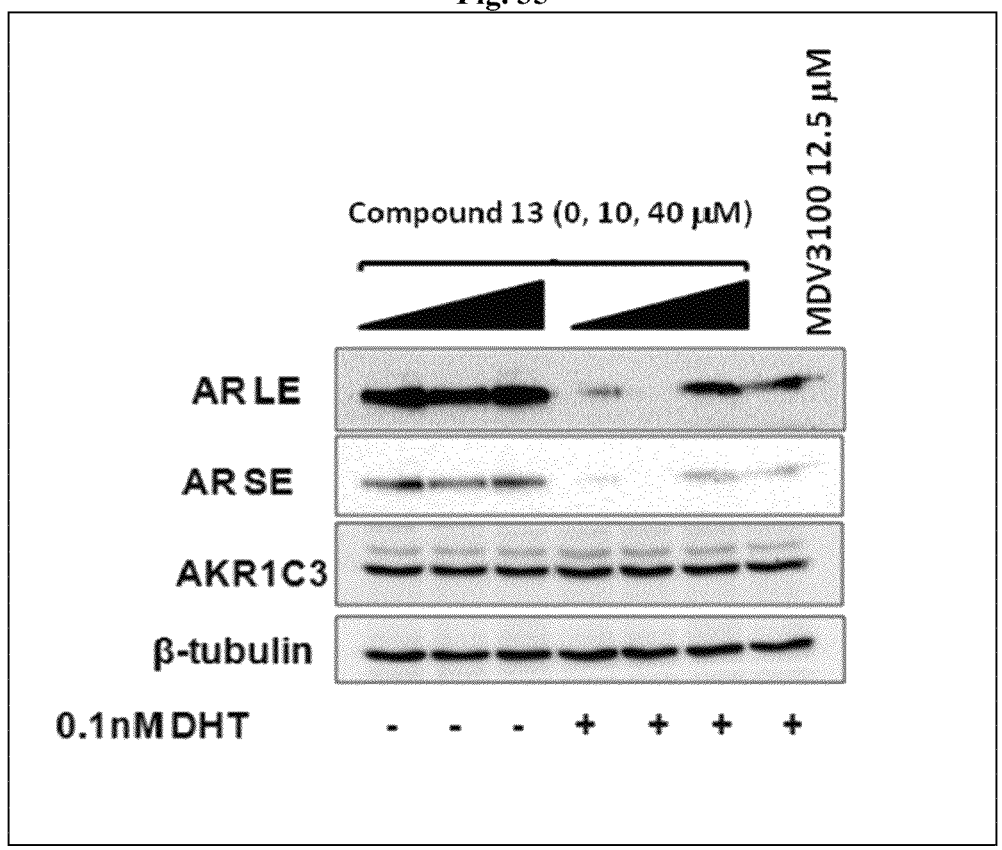
FIG. 35 is the detail of a gel illustrating the ability of the bifunctional agent (compound 13) to prevent AR nuclear translocation from the cytosol upon agonist binding in HeLa 13 cells. The experiment is replicated in the presence of 12.5 µM MDV3100. AR LE and AR SE=long and short exposure to detect cytoplasmic AR. β-tubulin was used as a loading control.

The ability of lead compounds to prevent nuclear localization of the AR in the presence and absence of the AR ligand 5α-DHT was also examined. Compound 13 caused a dose dependent increase in cytoplasmic AR in the presence of DHT and a similar response was observed with MDV3100, FIG. 35.

Quaternary Screens

A final screen may involve inhibition of tumor growth in a murine xenograft model of CRPC. The efficacy of compounds in xenograft models of CRPC and their ADMET properties may be determined to complete their preclinical evaluation. Scale up of synthesis is required under GLP conditions for an IND application to the FDA.

Example 31

Structure-Based Drug Design

Along with the twenty-two crystal structures of AKR1C3 deposited in the PDB, the x-ray crystal structure of the AKR1C3.NADP$^+$. 3-[N-4-trifluoromethylphenyl)amino] benzoic acid complex (PDB: 4DBU) and AKR1C3.NADP$^+$ .3'-[4-nitronaphthalen-1-yl)amino]benzoic acid (PDB: 4DBS) were analyzed. The former structure contained a representative monofunctional AKR1C3 inhibitor (compound 8) and suggested that AKR1C3 selectivity was achieved by the deep penetration of the ligand into the SP1 pocket.

Figure 36:
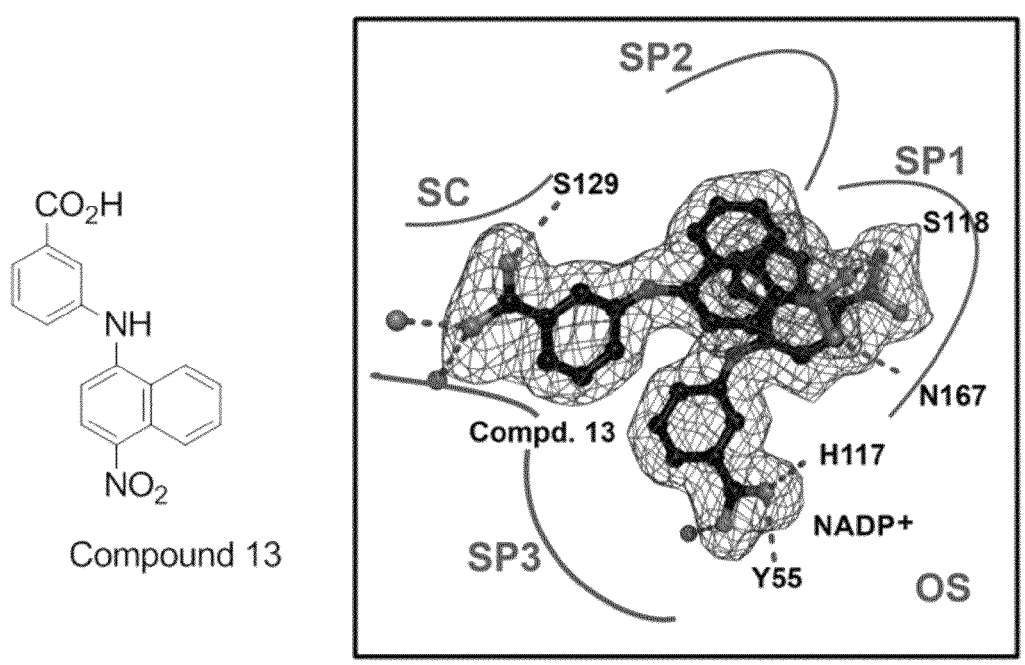
FIG. 36 is a schematic representation of how the bifunctional agent compound 13 binds to AKR1C3 based on the x-ray crystal structure of AKR1C3.NADP$^+$.3'-[(4-nitronaphthalen-1-yl)amino]benzoic acid (PDB: 4DBS).

The latter structure contained compound 13, which is a bifunctional AKR1C3 inhibitor and AR antagonist. In the structure, two molecules of the inhibitor were bound to give a double-decker structure (FIG. 36). In the first molecule of compound 13, the carboxylic acid was anchored in the oxyanion hole while the 4-nitronaphthalene ring penetrated the SP1 pocket. However, the nitro-naphthyl ring of compound 13 bound perpendicular to the phenyl ring of compound 8. This binding pose allowed space for the naphthyl ring of the second inhibitor molecule to fit inside the SP1 pocket forming a double-decker arrangement. The double decker binding of inhibitors has been reported previously for other aldo-keto reductases. In the complex of Alrestatin bound to aldose-reductase (AKR1B1), two molecules of Alrestatin occupy the active site forming face-to-face π-π stacking.

The inhibition dose-response curve of compound 13 also supported the multisite binding of the inhibitor to AKR1C3, showing a slope factor of approximately two, which indicated that the second molecule of compound 13 bound tightly to the enzyme and may play an important role in AKR1C3 inhibition. The Alrestatin double-decker structure has been suggested to confer the inhibitory selectivity for aldose-reductase over aldehyde reductase (AKR1A1) by specific hydrogen bonding between the second molecule of Alrestatin and the C-terminal loop of AKR1B1. In the present structure, two AKR1C3-specific hydrogen bonds between the second molecule of compound 13 and Ser118 and Ser129 (Phe118 and Ile/Leu129 in the other AKR1C isoforms) likely contributed to inhibitor selectivity. In one embodiment, occupancy of the SP1 pocket by ligands and interactions with Ser 118 and Ser 129 are key features that inform inhibitor design.

Example 32

Assessment of Drug Activity in Preclinical Xenograft Models of CRPC

Advantage may be taken of available xenograft models that progress from androgen dependent PC to CRPC, wherein the molecular basis for progression in each model may be assessed. Appropriate models are then used for preclinical studies of novel single agents or combinations therapies that may suppress intratumoral androgen synthesis or suppress AR activity by other mechanisms. Novel agents that are currently available for testing include a combined CYP17-hydroxylase/17,20-lyase inhibitor/AR antagonist, c-Src inhibitors, a cyclin dependent kinase (Cdk) inhibitor (Seliciclib), and any of the AKR1C3 inhibitors disclosed herein.

Overall, the objectives of these studies are: (a) establish the molecular efficacy (and mechanisms of failure) for the most promising pharmacological agents targeting the AR/ligand pathway; (b) identify and optimize combinatorial approaches to maximally inhibit AR signaling and ligand metabolism; (c) identify features of prostate tumors predicting response to particular AR/ligand targets; (d) identify the "final common pathway" of androgen-targeted resistance, and determine cell survival mechanisms that could/should be targeted (outside of the AR pathway), and (e) develop biomarkers (tissue/serum) that identify states of androgen pathway activity.

Assessment of the Activity of Novel Drugs and Combination Therapies Targeting AR in Preclinical Xenograft Models Representing a Spectrum of Castrate Sensitive Prostate Cancer (CSPC) and CRPC 1. Prostate Cancer Xenograft Models Encompassing a Spectrum of Castration Sensitive and Castration Resistant Phenotypes To facilitate preclinical studies of novel agents and combinations targeting the AR pathway, a collection of PC xenograft models that represent the clinical and molecular phenotypes/genotypes that could exhibit sensitivity and resistance to these targeted approaches was assembled. Twelve xenografts that reflect a framework of AR sensitivity states in human prostate cancer were selected: Endocrine Ligand Sensitive/AR Sensitive (LuCAP35; CWR22; LNCaP, VCaP, LAPC4); Intracrine Ligand Sensitive/AR Sensitive (LuCAP35V; LAPC4AI; LuCaP23.1); Ligand Insensitive/ AR Sensitive (LNCaP-Abl; C4-2); Ligand Insensitive/AR Insensitive (MDAPca118b (provided by Nora Navone); LuCaP49).

The AR-pathway status of each model is first characterized. Mice bearing each xenograft are castrated, and subsets of each are supplemented with 90-day release DHEA or androstenedione pellets (to obtain serum levels that are comparable to castrated men). Tumor and serum samples are taken just prior to castration, at 1 week after castration, and at the time of progression. Tumor and serum are analyzed for hormone levels. Expression of genes mediating androgen metabolism, and expression of AR and AR regulated genes (ligand-dependent versus ligand-independent M-phase target genes, ERG in VCaP) are also be analyzed by qRT-PCR and IHC. Finally, additional proteins (p160 coactivators, ErbB2, c-Src, etc.) and pathways (Ras-Raf-MAP kinase, PI3 kinase-Akt, etc.) implicated in progression to CRPC are assessed. A component of these studies also centers on further evaluating the expression of genes representing ligand-independent AR targets. For example, ChIP and shRNA approaches are used to confirm AR-mediated expression of UBE2C and other novel AR regulated M-phase genes in CRPC xenografts and derived cell lines. shRNA approaches are then used to assess whether UBE2C or other ligand independent AR regulated genes are critical for growth, and are therefore novel therapeutic targets. VCaP xenografts that relapsed after castration had upregulated androgen synthetic enzymes and reactivated TMPRSS2:ERG fusion gene expression, providing an excellent model for CRPC in patients.

2. Preclinical Xenograft Models

The panel of characterized xenografts is used to test agents (alone or in combination) targeting key cellular pathways that appear to contribute to CRPC. For example, lapatinib may enhance responses to castration in xenografts that adapt with increased EGFR1ErbB2 (reported previously for LAPC4) and sorafenib may enhance castration efficacy in tumors with Ras-Raf-MAP kinase activation, as shown for CWR22 after castration (Yuan et al., 2006, Am. J. Pathol. 169:682-96). A Cdk inhibitor, Seliciclib, is also tested based on the existing data showing that Cdk1 stabilizes AR in CRPC (Chen et al., 2006, Proc. Natl. Acad. Sci. USA 103:15969-74). Additional agents that may be tested are illustrated in FIG. 17.

3. Develop Novel Agents Targeting Androgen Synthesis and AR

The increased expression of AKR1C3, which mediates the reduction of $\Delta^4$-AD to testosterone and the reduction of 5α-androstane-3,17-dione to DHT in prostate (Penning et al., 2000, Biochem. J. 351:67-77), appears to be the key mechanism responsible for enhanced intratumoral androgen synthesis in CRPC. All AKR1C isoforms involved in the transformation of steroid hormones are potently inhibited by nonsteroidal anti-inflammatory drugs (NSAIDs), but AKR1C3 is uniquely inhibited by indomethacin. An agent shown to have marked activity in vivo in suppressing testosterone or 5α-DHT synthesis in appropriate CRPC xenografts (expressing increased AKR1 C3) may be advanced directly to a proof-of-principal clinical trial (possibly in combination with ketoconazole, hydrocortisone and dutasteride).

Androgen deprivation therapy is highly effective in the majority of prostate cancer patients, but the tumors cells adapt and eventually relapse as cancers that have been termed castration resistant prostate cancer (CRPC). Remarkably, despite castrate levels of androgens (testosterone and 5α-DHT) in the blood, it appears that these tumors are still being stimulated by androgens. Research has shown that these CRPC cells have enhanced their ability to synthesize androgens, so that levels of potent androgens in the tumors remain elevated. The compounds and methods disclosed herein may prove useful in the identification of an effective treatment therapy that targets such resistant tumors.

Example 33

X-Ray Studies

Figure 34:
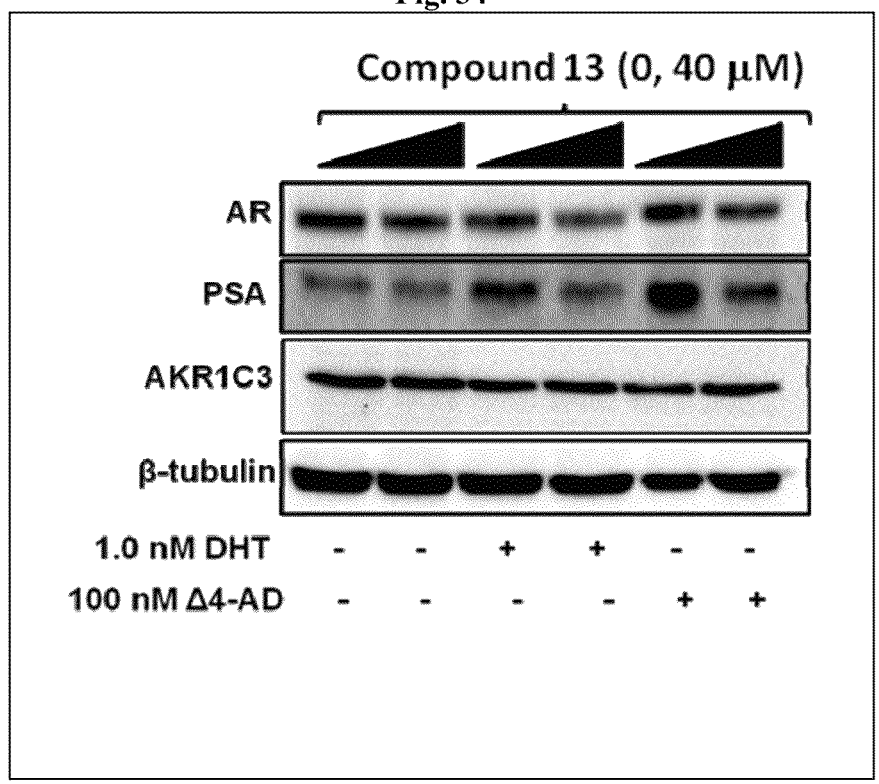
FIG. 34 is the detail of a gel illustrating the ability of the bifunctional agent (compound 13) to reduce mutated AR levels and PSA expression in LNCaP-AKR1C3 cells in the presence of the AR ligand DHT and the AKR1C3 substrate $\Delta^4$-AD.

To determine whether the bifunctional analog compound 13 targets the same binding subpocket as compound 7 to achieve AKR1C3 selectivity, compound 13 was co-crystallized in complex with AKR1C3 (FIG. 32). Two molecules of compound 13 were found per active site of AKR1C3. The first molecule of compound 13 was tethered to the oxyanion site similarly to compound 7, but its naphthyl ring was inserted into the SP1 subpocket perpendicular to the phenylamino ring of compound 7. This binding pose allowed space for the naphthyl ring of the second inhibitor molecule to fit inside the SP1 pocket forming a double decker arrangement. The unexpected arrangement allowed Phe306 to swing back to its original position in the AKR1C3.NADP+.Compound 1 complex (FIG. 34). However, to accommodate the second molecule of compound 13, Phe311 was pushed even further away from the SP1 pocket leading to a 90° rotation of its phenyl ring. The inhibition dose-response curve of compound 13 also supported the multisite binding of the inhibitor to AKR1C3 by showing a slope factor of approximately two, indicating that the second molecule of compound 13 bound tightly to the enzyme and may play an important role in the inhibition. In the AKR1C3.NADP+.Compound 13 complex, two AKR1C3 specific hydrogen bonds between the second compound 13 molecule and Ser118 and Ser129 (Phe118 and Ile/Leu129 in the other AKR1C isoforms) likely contributed to inhibitor selectivity.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating or ameliorating cancer in a subject in need thereof, said method comprising administering to said subject a therapeutically effective amount of at least one compound selected from the group consisting of:

(i) a compound of Formula (I):

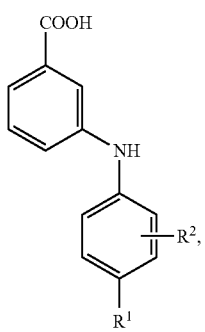

(I)

wherein in Formula (I):
$R^1$ is selected from the group consisting of $C_1$-$C_6$ alkyl, haloalkyl, halo, nitro, —CN, $C_1$-$C_6$ alkoxy, —C(=O)H, —C(=O)OH, —C(=O)—($C_1$-$C_6$ alkyl), and —SO$_3$H; and, each occurrence of $R^2$ is independently selected from the group consisting of H, $C_1$-$C_6$ alkyl, haloalkyl, halo, nitro, —CN, $C_1$-$C_6$ alkoxy, —C(=O)H, —C(=O)OH, —C(=O)—($C_1$-$C_6$ alkyl), and —SO$_3$H; and, (ii) a compound of Formula (II) where the naphthyl ring can be alpha or beta substituted:

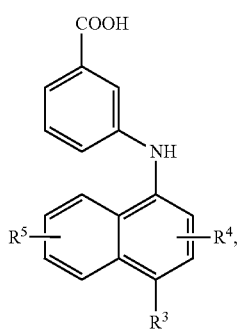

(II)

wherein in Formula (II):
$R^3$ is selected from the group consisting of $C_1$-$C_6$ alkyl, haloalkyl, halo, nitro, —CN, $C_1$-$C_6$ alkoxy, —C(=O)H, —C(=O)OH, —C(=O)—($C_1$-$C_6$ alkyl), and —SO$_3$H; and, each occurrence of $R^4$ and $R^5$ is independently selected from the group consisting of H, $C_1$-$C_6$ alkyl, haloalkyl, halo, nitro, —CN, $C_1$-$C_6$ alkoxy, —C(=O)H, —C(=O)OH, —C(=O)—($C_1$-$C_6$ alkyl), and —SO$_3$H; mixtures thereof and salts thereof, whereby said administering treats or ameliorates said cancer in said subject, wherein said cancer has upregulated AKR1C3 expression and is selected from the group consisting of prostate cancer, breast cancer, endometrial cancer, acute myelogenous leukemia, and combinations thereof.

2. The method of claim 1, wherein said prostate cancer comprises castrate resistant prostate cancer.

3. The method of claim 1, wherein said cancer is androgen dependent.

4. The method of claim 1, wherein said compound of Formula (I) is selected from the group consisting of 3-[N-(4-nitrophenyl)amino]benzoic acid, 3-[N-(4-acetylphenyl)amino]benzoic acid, 3-[N-(4-trifluoromethylphenyl)amino]benzoic acid, 3-[N-(4-chlorophenyl)amino]benzoic acid, 3-[N-(4-bromophenyl)amino]benzoic acid, 3-[N-(4-tert-butylphenyl)amino]benzoic acid, 3-[N-(4-methoxyphenyl)amino]-benzoic acid, 3-[N-(4-methylphenyl)amino]benzoic acid, mixtures thereof and salts thereof.

5. The method of claim 1, wherein said compound of Formula (II) is 3-((4-nitronaphthalen-1-yl)amino)benzoic acid or a salt thereof.

6. The method of claim 1, wherein said cancer is prostate cancer and wherein said method further comprises administering to said subject at least one therapeutic agent selected from the group consisting of indomethacin, desatinib, selegiline, seliciclib, TOK-001, SAHA, docetaxel, bevacizumab, taxotere, thalidomide, prednisone, Sipuleucel-T, cabazitaxel, MDV3100, ARN-509, abiraterone, temozolomide, mixtures thereof and salts thereof.

7. The method of claim 6, wherein said composition and said at least one therapeutic agent are administered concomitantly to said subject.

8. The method of claim 7, wherein said composition and said at least one therapeutic agent are co-formulated.

9. The method of claim 7, wherein said cancer is breast cancer and wherein said method further comprises administering to said subject at least one therapeutic agent selected from the group consisting of tamoxifen, anastrozole, letrozole, vorozole, exemestane, fadrozole, formestane, raloxifene, mixtures thereof and salts thereof.

10. The method of claim 9, wherein said composition and said at least one therapeutic agent are administered concomitantly to said subject.

11. The method of claim 10, wherein said composition and said at least one therapeutic agent are co-formulated.

12. The method of claim 1, wherein said subject is a human.

* * * * *

UNITED STATES PATENT AND TRADEMARK OFFICE
CERTIFICATE OF CORRECTION

PATENT NO.          : 9,271,961 B2                        Page 1 of 1
APPLICATION NO.     : 14/050937
DATED               : March 1, 2016
INVENTOR(S)         : Trevor M. Penning et al.

It is certified that error appears in the above-identified patent and that said Letters Patent is hereby corrected as shown below:

On the title page item (72), Inventors: "Michael C. Burns" should be changed to --Michael C. Byrns--.

Signed and Sealed this
Twenty-third Day of August, 2016

Michelle K. Lee
*Director of the United States Patent and Trademark Office*